United States Patent
Okado et al.

(10) Patent No.: US 6,194,166 B1
(45) Date of Patent: *Feb. 27, 2001

(54) GENE REGULATING AUREOBASIDIN SENSITIVITY

(75) Inventors: Takashi Okado, Soraku-gun; Kazutoh Takesako, Otsu; Ikunoshin Kato, Uji, all of (JP)

(73) Assignee: Takara Shuzo Co., Ltd., Kyoto-Fu (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/716,873

(22) Filed: Sep. 20, 1996

Related U.S. Application Data

(63) Continuation-in-part of application No. 08/492,459, filed on Jun. 29, 1995, now Pat. No. 6,015,689, which is a continuation-in-part of application No. 08/243,403, filed on May 16, 1994, now abandoned.

(30) Foreign Application Priority Data

| May 24, 1993 | (JP) | 5-142523 |
| Dec. 28, 1993 | (JP) | 5-348893 |
| Jun. 29, 1994 | (JP) | 6-168611 |
| Mar. 30, 1995 | (JP) | 7-95831 |
| Mar. 30, 1995 | (JP) | 7-95955 |
| May 17, 1995 | (JP) | 7-141393 |
| Oct. 4, 1995 | (JP) | 7-279921 |

(51) Int. Cl.$^7$ .................................... C12N 15/00

(52) U.S. Cl. ................. 435/69.1; 435/252.3; 435/320.1; 435/254.1; 435/254.3; 435/6; 536/23.1; 536/23.74; 536/23.7; 935/52; 935/55; 935/56

(58) Field of Search ............... 435/69.1, 252.3, 435/320.1, 254.1, 254.3, 6; 536/23.1, 23.74, 23.7; 935/52, 55, 56

(56) References Cited

FOREIGN PATENT DOCUMENTS

| 0 644 262 A2 | 3/1995 | (EP) . |
| 0 692 534 A2 | 1/1996 | (EP) . |

OTHER PUBLICATIONS

S. Heidler et al., "The AUR1 Gene in *Saccharomyces cerevisiae* Encodes Dominant Resistance to the Antifungal Agent Aureobasidin A (LY295337)", Antimicrobial Agents and Chemotherapy, vol. 39, No. 12, pp. 2765–2769, Dec. 1995.

R. Dickson et al., "Synthesis of Mannose–(inositol–P)$_2$–ceramide, the Major Sphingolipid in *Saccharomyces cerevisiae*, Requires the IPT1 (YDRO72c) Gene", The Journal of Biological Chemistry, vol. 272, No. 47, pp. 29620–29625, Nov. 21, 1997.

T. Hashida–Okado et al., "Cloning and Characterization of a Gene Conferring Resistance to the Antifungal Antibiotic Aureobasidin A(R106–I) in Yeast", Faseb Journal, vol. 9, No. 6, p. A1371, Apr. 24, 1995 * abstract *.

Boyer et al. (1994) Accession Number Z28004 EMBL/GenBank/DDBJ Databases. *S. cerevisiae* Chromosome XI reading frame ORF YKL004w.*

* cited by examiner

*Primary Examiner*—Robert A. Wax
*Assistant Examiner*—Enrique D. Longton
(74) *Attorney, Agent, or Firm*—Wenderoth, Lind & Ponack, L.L.P.

(57) ABSTRACT

The invention is directed to isolated DNAs having nucleic acid sequences which encode proteins which regulate aureobasidin sensitivity. Also disclosed are recombinant plasmids containing the DNAs, transformants containing the plasmids, and methods of producing the proteins.

32 Claims, 14 Drawing Sheets

FIG. 18

```
                                              Box-1
150  AIWVRVLPAL ENILYGANIS NILSAHQNVV |LDVLAWLPYG| ICHYGAPFVC
150  AIWVRVLPAL ENILYGANIS NILSAHQNVV |LDVLAWLPYG| ICHYGAPFVC
115  PITVKVLPAV ETILYGDNLS DILATSTNSF |LDILAWLPYG| LFHFGAPFVV
115  PIWVRVLPTL ENILYGSNLS SLLSKTTHSI |LDILAWVPYG| VMHYSAPFII
128  AITVKVLPAM ETILYGDNLS NVLATITTGV |LDILAWLPYG| IIHFSFPFVL

SLIMFIFGPP GTVPLFARTF GYISMTAVTI QLFFPCSPPW YENRYGLAPA
     SAIMFIFGPP GTVPLFARTF GYISMAAVTI QLFFPCSPPW YENLYGLAPA
     AAILFVFGPP TVLQGYAFAF GYMNLFGVIM QNVFPAAPPW YKILYGLQSA
     SFILFIFAPP GTLPVWARTF GYMNLFGVLI QMAFPCSPPW YENMYGLEPA
     AAIIFLFGPP TALRSFGFAF GYMNLLGVLI QMAFPAAPPW YKNLHGLEPA

Box-1
     DYSIQGDPAG LARIDKLFGI DLYTSGFHQS PVV|FGAFPSL H|AADSTLAAL
     DYSMPGNPAG LARIDELFGI DLYTSGFRQS PVV|FGAFPSL H|AADSTLAAL
     NYDMHGSPGG LARIDKLLGI NMYTTAFSNS SVI|FGAFPSL H|SGCATMEAL
     TYAVRGSPGG LARIDALFGT SIYTDGFSNS PVV|FGAFPSL H|AGWAMLEAL
     NYSMHGSPGG LGRIDKLLGV DMYTTGFSNS SII|FGAFPSL H|SGCCIMEVL

Box-3
     FMSHVFPRMK PVFVTYTLWM WWA|TMYLSHH YAVDL|VAGGL LAAIAFYFAK  349
     FMSQVFPRLK PLFVIYTLWM WWA|TMYLSHH YAVDL|VGGGL LATVAFYFAK  349
     FFCYCFPKLK PLFIAYVCWL WWS|TMYLTHH YFVDL|MAGSV LSYVIFQYTK  314
     FLSHVFPRYR FCFYGYVLWL CWC|TMYLTHH YFVDL|VGGMC LAIICFVFAQ  314
     FLCWLFPRFK FVWVTYASWL WWS|TMYLTHH YFVDL|IGGAM LSLTVFEFTK  327
```

GENE REGULATING AUREOBASIDIN SENSITIVITY

This application is a continuation in part of application Ser. No. 08/492,459 filed Jun. 29, 1995 now U.S. Pat. No. 6,015,689 which is a continuation in part of application Ser. No. 08/243,403, filed May 16, 1994, now abandoned.

FIELD OF THE INVENTION

This invention relates to a protein regulating a sensitivity to an antimycotic aureobasidin, a gene encoding this protein and to uses of the protein and gene.

DESCRIPTION OF RELATED ART

Systemic mycoses including candidiasis have increased with an increase in immunocompromised patients in recent years due to, for example, the extended use of immunosuppressive drugs and acquired immunodeficiency syndrome (AIDS), and as opportunistic infection due to microbial substitution caused by the frequent use of widespectrum antibacterial antibiotics. Although drugs for treating mycoses such as amphotericin B, flucytosine and azole drugs (for example, fluconazole and miconazole) are now used to cope with this situation, none of them can achieve a satisfactory effect. Also, known diagnostic drugs are insufficient. For candidiasis, in particular, although there have been known several diagnostic drugs (for example, CAND-TEC for detection of candida antigen and LABOFIT for detection of D-arabinitol), none of them gives any satisfactory results in specificity or sensitivity.

The reasons for the delay in the development of remedies and diagnostic drugs for mycoses as described above are that fungi causing the mycoses are eukaryotic organisms similar to the host (i.e., man) and thus are not largely different from man and that knowledges of fungi, in particular, pathogenic fungi are insufficient. Therefore it is difficult to distinguish fungi from man or to selectively kill fungi, which is responsible for the delay in the development of drugs for mycoses.

Recently, the application of genetic engineering techniques such as antisense or PCR to the treatment and diagnosis of mycoses has been expected. However known genes which are applicable thereto and/or proteins coded for by these genes are rare (PCT Pamphlet WO92/03455). Regarding pathogenic fungi, there have been cloned in recent years an acid protease gene, which has been assumed to participate in the pathogenicity of Candida albicans (hereinafter referred to simply as C. albicans) and Candida tropicalis (hereinafter referred to as C. tropicalis) causing candidiasis [B. Hube et al., J. Med. Vet. Mycol., 29, 129–132 (1991); Japanese Patent Laid-Open No. 49476/1993; and G. Togni et al., FEBS Letters, 286, 181–185 (1991)], a calmodulin gene of C. albicans [S. M. Saporito et al., Gene, 106, 43–49 (1991)] and a glycolytic pathway enzyme enolase gene of C. albicans [P. Sundstrom et al., J. Bacteriology, 174, 6789–6799 (1991)]. However, each of these genes and proteins coded for thereby is either indistinguishable from nonpathogenic fungi and eukaryotic organisms other than fungi or, if distinguishable therefrom, cannot serve as a definite action point for exhibiting any selective toxicity.

Aureobasidin [Japanese Patent Laid-Open No. 138296/1990, No. 22995/1991, No. 220199/1991, No. 279384/1993, and No. 65291/1994; J. Antibiotics, 44 (9), 919–924, ibid., 44 (9), 925–933, ibid., 44 (11), 1187–1198 (1991)] is a cyclic depsipeptide obtained as a fermentation product of a strain Aureobasidium pullulans No. R106. It is completely different in structure from other antimycotics. As Tables 1 and 2 show below, aureobasidin A, which is a typical aureobasidin compound, exerts a potent antimycotic activity on various yeasts of the genus Candida including C. albicans which is a pathogenic fungus, Cryptococcus neoformans, Histoplasma capsulatum, Blastomyces dermatitidis and fungi of the genus Aspergillus and Penicillium (Japanese Patent Laid-Open No. 138296/1990) but has an extremely low toxicity in mammal. Thus this compound is expected to be useful as an antimycotic being excellent in selective toxicity.

Hereinafter, Candida, Cryptococcus and Aspergillus will be abbreviated respectively as C, Cr. and A.

TABLE 1

| Test Strain | TIMM No. | MIC($\mu$g/ml) |
| --- | --- | --- |
| C. albicans | 0136 | $\leq$0.04 |
| C. albicans var. stellatoidea | 1308 | $\leq$0.04 |
| C. tropicalis | 0312 | 0.08 |
| C. kefyr | 0298 | 0.16 |
| C. parapsilosis | 0287 | 0.16 |
| C. krusei | 0270 | $\leq$0.04 |
| C. guilliermondii | 0257 | 0.08 |
| C. glabrata | 1062 | <0.04 |
| Cr. neoformans | 0354 | 0.63 |
| Cr. terreus | 0424 | 0.31 |
| Rhodotorula rubra | 0923 | 0.63 |
| A. fumigatus | 0063 | 20 |
| A. clavatus | 0056 | 0.16 |

TABLE 2

| Test Strain | TIMM No. | MIC($\mu$g/ml) |
| --- | --- | --- |
| A. nidulans | 0112 | 0.16 |
| A. terreus | 0120 | 5 |
| Penicillium commune | 1331 | 1.25 |
| Trichophyton mentagrophytes | 1189 | 10 |
| Epidermophyton floccosum | 0431 | 2.5 |
| Fonsecaea pedrosoi | 0482 | 0.31 |
| Exophiala werneckii | 1334 | 1.25 |
| Cladosporium bantianum | 0343 | 0.63 |
| Histoplasma capsulatum | 0713 | 0.16 |
| Paracoccidioides brasiliensis | 0880 | 0.31 |
| Geotrichum candidum | 0694 | 0.63 |
| Blastomyces dermatitidis | 0126 | 0.31 |

Each of the existing antimycotics with a low toxicity shows only a fungistatic action, which causes a clinical problem. In contrast, aureobasidin exerts a germicidal action. Although it has been required to clarify the mechanism of the selective toxicity of aureobasidin from these viewpoints, this mechanism still remains completely unknown.

As described in Canadian Patent Laid-Open No. 2124034, the present inventors have previously found out that Saccharomyces cerevisiae (hereinafter referred to simply as S. cerevisiae) and Schizosaccharomyces pombe (hereinafter referred to simply as Schizo. pombe) are sensitive to aureobasidin. We have further mutated sensitive cells of S. cerevisiae or Schizo. pombe into resistant cells and successfully isolated a gene capable of imparting a resistance to aureobasidin (a resistant gene) therefrom. We have furthermore successfully isolated a gene capable of imparting aureobasidin sensitivity (a sensitive gene) from the corresponding sensitive cells.

We have also isolated a gene regulating aureobasidin sensitivity from C. albicans with the use of the gene regulating aureobasidin sensitivity or a part thereof as a probe. However no gene regulating aureobasidin sensitivity has been found in molds including those belonging to the genus Aspergillus.

There have been known techniques for introducing useful genes into monoploid fungal cells to be used in a laboratory, for example, Saccharomyces cerevisiae (hereinafter referred to simply as S. cerevisiae), Schizosaccharomyces pombe (hereinafter referred to simply as Schizo. pombe) and Aspergillus nidulans (hereinafter referred to simply as A. nidulans). Since the incorporation and fixation of plasmid DNAs into fungal cells are relatively scarcely successful, it is required to use selective markers in the identification of transformants. In the most common case, selection can be achieved by introducing an auxotrophic mutation into host cells. Examples of the mutation generally employed in, for example, S. cerevisiae include ura3, leu2, trp1 and his3. A plasmid carries a wild type copy of one of these genes. Since the wild type copy on the plasmid is dominant over the chromosomal allele of the host, cells having the plasmid introduced thereinto can be screened in a minimal medium which contains no nutrient required by the auxotrophic host cells. Also there have been published some reports, though in a small number, relating to the use of drug resistance in the screening of transformants. Namely, there have been reported replication vectors and chromosome integration vectors containing genes which are resistant against antibiotics such as a neomycin homologue G418, hygromycin and cerulenin. A replication vector has a DNA replication origin acting in a cell. This plasmid is held outside the chromosome as a cyclic episome and continuously reduced at a ratio of several percent with the proliferation of the cells. An integration vector is inserted into the chromosome of a host cell and thus held in a stable state. In this case, therefore, it is unnecessary to further add a drug to the medium in order to exert the selection function for maintaining the sequence of the vector.

In the case of industrial fungi, it is required to sustain the useful character, which has been imparted thereto, in a stable state. A chromosome integration vector is useful for this purpose.

Fungi have been widely applied to the production of liquors such as sake, beer and wine and fermented foods such as miso (fermented soy bean paste) and soy sauce. For breeding these fungi to be used for industrial purposes, genetic engineering techniques are also highly effective in order to impart useful characteristics thereto. Thus there have been required selective markers which are usable in efficiently screening transformants. Industrial yeasts are usually di- or polyploid cells. It is therefore difficult to introduce an auxotrophic marker, which is effective in monoploid cells of, for example, yeasts to be used in a laboratory, into these industrial yeasts. In addition, since there is a high possibility that a mutagenesis induces mutation in other genes, accordingly, it is highly difficult to create a mutant having the desired auxotrophic mutation alone introduced thereinto. The use of a drug resistance makes it possible to screen a stable transformant of an arbitrary yeast regardless of the number of chromosomes or the occurrence of specific mutation. However many of these industrial fungi are insensitive to antibiotics such as G-418 and hygromycin, which makes it impossible to use genes resistant against these antibiotics therefor. Moreover, these resistant genes are genes or proteins derived from bacteria which are procaryotes, and none of them corresponding to these genes is present in fungi such as yeasts. The use of fungal cells having these foreign genes integrated therein is seriously restricted. A cerulenin resistant gene (PDR4) originating in S. cerevisiae is usable in the transformation of S. cerevisiae including brewing yeast. However it also conferred resistances against drugs other than cerulenin, which might bring about some problems in the practical use. Therefore PDR4 cannot fully satisfy the requirements for breeding industrial fungi including S. cerevisiae having improved characters in the future. Thus it has been required to develop drug resistant markers with the use of genes which are inherently carried by fungi.

There are a number of molds such as the ones of the genera Aspergillus and Penicillium. Some of these molds have been applied to food manufacturing (for example, brewing of liquors, soy sauce and miso, ripening of cheese, etc.) for a long time, while a number of them are important in the production of enzyme preparations or antibiotics. However, molds include not only these useful ones as described above but also harmful ones such as those inducing plant diseases and those causing serious human diseases such as deep-seated mycosis. The recent development in genetic engineering techniques has made it possible not only to breed useful strains but also to apply molds to novel purposes, for example, the production of a heterogenic protein. Also, analyses of vital phenomena of molds are under way.

An object of the present invention is to find a gene, which encodes a protein regulating aureobasidin sensitivity and which is useful in genetic engineering techniques and in analyses of vital phenomena of molds from molds including those belonging to the genus Aspergillus and its functional derivative. That is to say, the present invention aims at revealing a gene which encodes a protein regulating aureobasidin sensitivity or its functional derivative; providing a method for cloning this gene and a protein regulating aureobasidin sensitivity encoded by this gene or its functional derivative; providing the antisense DNA and the antisense RNA of this gene; providing a nucleic acid probe hybridizable with this gene and a method for detecting this gene by using this nucleic acid probe; and providing a process for producing a protein regulating aureobasidin sensitivity or its functional derivative by using this gene.

Under these circumstances, the present invention further aims at finding a novel protein regulating aureobasidin sensitivity through the clarification of the mechanism of the selective toxicity to fungi of aureobasidin. Accordingly, the present invention aims at finding a gene coding for a protein regulating aureobasidin sensitivity, providing a process for cloning this gene and the protein regulating aureobasidin sensitivity which is encoded by this gene, further providing an antisense DNA and an antisense RNA of this gene, providing a nucleic acid probe being hybridizable with this gene, providing a process for detecting this gene with the use of the nucleic acid probe, providing a process for producing the protein regulating aureobasidin sensitivity by using this gene and providing an antibody against the protein regulating aureobasidin sensitivity, and a process for detecting the protein regulating aureobasidin sensitivity by using this antibody.

In addition, the present invention aims at providing a novel chromosome integration vector capable of imparting a novel selective marker of a drug resistance to a fungal transformant, and a transformant transformed by this vector.

The present invention further aims at providing a protein capable of imparting the aureobasidin resistance and acting as a selective marker which is usable in genetic engineering of fungi, and a DNA coding for this protein.

SUMMARY OF THE INVENTION

The present invention may be summarized as follows. Namely, the first invention of the present invention relates to an isolated gene coding for a protein regulating aureobasidin sensitivity, that is, a gene regulating aureobasidin sensitivity. The second invention relates to a process for cloning a gene regulating aureobasidin sensitivity which is characterized by using the gene regulating aureobasidin sensitivity of the first invention or a part thereof as a probe. The third invention relates to a nucleic acid probe which is hybridizable with a gene regulating aureobasidin sensitivity and comprises a sequence consisting of 15 or more bases. The fourth invention relates to an antisense DNA of a gene regulating aureobasidin sensitivity. The fifth invention relates to an antisense RNA of a gene regulating aureobasidin sensitivity. The sixth invention relates to a recombinant plasmid having a gene regulating aureobasidin sensitivity contained therein. The seventh invention relates to a transformant having the above-mentioned plasmid introduced thereinto. The eighth invention relates to a process for producing a protein regulating aureobasidin sensitivity by using the above-mentioned transformant. The ninth invention relates to an isolated protein regulating aureobasidin sensitivity. The tenth invention relates to an antibody against a protein regulating aureobasidin sensitivity. The eleventh invention relates to a process for detecting a protein regulating aureobasidin sensitivity by using the above-mentioned antibody. The twelfth invention relates to a process for detecting a gene regulating aureobasidin sensitivity by the hybridization which is characterized by using the nucleic acid probe of the third invention of the present invention. The thirteenth invention relates to a process for screening an antimycotic by using the above-mentioned transformant or a protein regulating aureobasidin sensitivity. The fourteenth invention of the present invention relates to a chromosome integration vector for a host fungus which is characterized by containing an aureobasidin resistant gene. This chromosome integration vector sometimes contains a foreign gene. The fifteenth invention relates to a process for producing an aureobasidin resistant transformant characterized by comprising:

(1) the step of obtaining a replication vector which contains an aureobasidin resistant gene,
(2) the step of cleaving the aureobasidin resistant gene in the replication vector obtained in the above step at one site to give a chromosome integration vector for a host fungus;
(3) the step of integrating the chromosome integration vector for a host fungus obtained in the above step into the chromosome of the host fungus; and
(4) the step of selecting a host which has been transformed into an aureobasidin resistant one in the presence of aureobasidin.

In this process for producing an aureobasidin resistant transformant, the replication vector sometimes contains a foreign gene. The sixteenth invention relates to a transformant characterized by being one obtained by the process of the fifteenth invention.

The seventeenth invention relates to a protein capable of imparting aureobasidin resistance, wherein at least the 240th amino acid residue Ala in the protein capable of imparting aureobasidin sensitivity represented by SEQ ID No. 22 in the Sequence Listing has been replaced by another amino acid residue, or another protein capable of imparting aureobasidin resistance which has an amino acid sequence obtained by subjecting the above-mentioned protein to at least one modification selected from replacement, insertion and deletion of amino acid residue(s) and shows a biological activity comparable to that of the above-mentioned protein. The eighteenth invention relates to a DNA which codes for the protein capable of imparting the aureobasidin resistance of the seventeenth invention.

The nineteenth invention relates to a gene originating in a mold which encodes a protein regulating aureobasidin sensitivity or its functional derivative. Namely, it relates to a gene regulating aureobasidin sensitivity obtained from a mold or a functional derivative thereof. The twentieth invention relates to a method for cloning a gene regulating aureobasidin sensitivity and originating in a mold or its functional derivative wherein the gene regulating aureobasidin sensitivity of the nineteenth invention or its functional derivative is employed as a probe either as the whole or a part thereof. The twenty-first invention relates to a nucleic acid probe comprising a sequence consisting of at least 15 bases which is hybridizable with a gene regulating aureobasidin sensitivity and originating in a mold or its functional derivative. The twenty-second invention relates to the antisense DNA of a gene regulating aureobasidin sensitivity and originating in a mold or its functional derivative. The twenty-third invention relates to the antisense RNA of a gene regulating aureobasidin sensitivity and originating in a mold or its functional derivative. The twenty-fourth invention relates to a recombinant plasmid which contains a gene regulating aureobasidin sensitivity and originating in a mold or its functional derivative. The twenty-fifth invention relates to a transformant which has the plasmid of the twenty-fourth invention introduced thereinto. The twenty-sixth invention relates to a process for producing a protein regulating aureobasidin sensitivity or its functional derivative with the use of the above-mentioned transformant. The twenty-seventh invention relates to a protein regulating aureobasidin sensitivity and originating in a mold or its functional derivative. The twenty-eighth invention relates to a protein capable of imparting the resistance to aureobasidin, wherein at least the amino acid Gly at the position 275 of the protein imparting aureobasidin sensitivity represented by SEQ ID NO. 4 in the Sequence Listing has been replaced by another amino acid, or its functional derivative. The twenty-ninth invention relates to a DNA which encodes the protein of the twenty-eighth invention capable of imparting the resistance to aureobasidin. The thirtieth invention relates to a method for detecting a gene regulating aureobasidin sensitivity by hybridization with the use of the nucleic acid probe of the twenty-first invention.

As described in Japanese Patent Application No. 106158/1994, the present inventors have previously found out that fungi such as Schizo. pombe and S. cerevisiae and, further, mammalian cells such as mouse lymphoma EL-4 cells, are sensitive to aureobasidin, as Table 3 shows.

TABLE 3

| Test Strain or Cell | MIC(μg/ml) |
|---|---|
| Schizo. pombe | 0.08 |
| S. cerevisiae | 0.31 |
| mouse lymphoma EL-4 | 10 |
| mouse lymphoma L5178Y | 100 |
| NRK-49F | 12.5 |

The present inventors have mutagenized a wild-type strain of Schizo. pombe or S. cerevisiae, sensitive to aureobasidin, to thereby give resistant mutants. We have further successfully isolated a gene capable of confering aureobasidin resistance (a resistant gene) from these resistant mutants and another gene capable of imparting aureobasidin sensitivity (a sensitive gene) from the corresponding sensitive cells. Furthermore, we have disclosed the existence of a protein encoded by each of these genes. By culturing cells which have been transformed by introducing the above-mentioned gene, we have succeeded in the expression of this gene. Furthermore, we have successfully found out a novel gene regulating aureobasidin sensitivity from another fungus being sensitive to aureobasidin by using a DNA fragment of the above-mentioned gene as a probe. In addition, we have clarified that the gene regulating aureobasidin sensitivity is essentially required for the growth of the cells and found out that the detection of this gene or a protein which is a gene product thereof with an antibody enables the diagnosis of diseases caused by these cells, for example, mycoses induced by fungi, and that an antisense DNA or an antisense RNA, which inhibits the expression of the gene regulating aureobasidin sensitivity being characteristic to the cells, is usable as a remedy for diseases caused by these cells, for example, mycoses induced by fungi, thus completing the present invention. The present inventors have also succeeded in the expression of this gene by preparing a replication vector containing this gene and incubating cells transformed by using this vector. By using a DNA fragment of this gene as a probe, they have further successfully found a novel gene regulating the aureobasidin sensitivity from another fungus which is sensitive to aureobasidin.

The pathogenic fungi listed in Tables 1 and 2 and fungi and mammalian cells listed in Table 3, each having a sensitivity to aureobasidin; each carries a protein regulating aureobasidin sensitivity and a gene coding for this protein. The term "a protein regulating aureobasidin sensitivity" as used herein means a protein which is contained in an organism, particularly a fungus, having a sensitivity to aureobasidin. This protein is required for the expression of the sensitivity or resistance to aureobasidin. As a matter of course, a protein having 35% or more homology with the above-mentioned protein and having a similar function is also a member of the protein regulating aureobasidin sensitivity according to the present invention. Furthermore, proteins obtained by modifying these proteins by the genetic engineering procedure are members of the protein regulating aureobasidin sensitivity according to the present invention. A gene regulating aureobasidin sensitivity means a gene which codes for such a protein regulating aureobasidin sensitivity as those described above and involves both of sensitive genes and resistant genes.

The first invention of the present invention relates to a gene regulating aureobasidin sensitivity. This gene can be isolated in the following manner. First, aureobasidin sensitive cells (a wild-type strain) are mutagenized to thereby induce a resistant strain. From chromosome DNA or cDNA of this resistant strain, a DNA library is prepared and a gene capable of confering resistance (a resistant gene) is cloned from this library. Then a DNA library of a wild strain is prepared and a DNA molecule being hybridizable with the resistant gene is isolated from this library and cloned. Thus a sensitive gene can be isolated.

The mutagenesis is performed by, for example, treating with a chemical such as ethylmethane sulfonate (EMS) or N-methyl-N'-nitro-N-nitrosoguanidine (MNNG) or by ultraviolet or other radiation. The cell that has acquired the resistance can be screened by culturing the mutagenized cells in a nutritional medium containing aureobasidin at an appropriate concentration under appropriate conditions. The resistant strain thus obtained may vary depending on the method and conditions selected for the mutagenesis. Also, strains differing in the extent of resistance from each other can be separated by changing the aureobasidin concentration or a temperature-sensitive resistant strain can be isolated by changing the temperature in the step of screening. There are a number of mechanisms of resistance to aureobasidin. Accordingly, a number of resistant genes can be isolated by genetically classifying these various resistant strains. In the case of a yeast, the classification may be performed by the complementation test. Namely, resistant strains are prepared from haploid cells. Next, diploid cells can be obtained by crossing resistant strains differing in mating type from each other. Then spores formed from these diploids are examined by the tetrad analysis.

As typical examples of the genes regulating aureobasidin sensitivity (named aur) according to the present invention, aur1 and aur2 genes may be cited. Typical examples of the aur1 gene include spaur1 gene isolated from Schizo. pombe and scaur1 gene isolated from S. cerevisiae, while typical examples of the aur2 gene include scaur2 gene isolated from S. cerevisiae. Now, resistant genes (spaur1$^R$, scaur1$^R$ and scaur2$^R$) isolated from resistant mutants by the present inventors and sensitive genes (spaur1$^S$, scaur1$^S$ and scaur2$^S$) isolated from sensitive wild-type strains will be described.

FIG. 1 shows a restriction enzyme map of the genes spaur1$^R$ and spaur1$^S$ regulating aureobasidin sensitivity, FIG. 2 shows a restriction enzyme map of scaur1$^R$ and scaur1$^S$ and FIG. 3 shows a restriction enzyme map of scaur2$^R$ and scaur2$^S$.

Schizo. pombe, which is sensitive to aureobasidin, is mutagenized with EMS and a genomic library of the resistant stain thus obtained is prepared. From this library, a DNA fragment containing a resistant gene (spaur1$^R$) and having the restriction enzyme map of FIG. 1 is isolated. This gene has a nucleotide sequence represented by SEQ ID No. 15 in Sequence Listing. The amino acid sequence of a protein encoded by this gene, which is estimated on the basis of this nucleotide sequence, is the one represented by SEQ ID No. 16 in Sequence Listing. By the hybridization with the use of this resistant gene as a probe, a DNA fragment containing a sensitive gene (spaur1$^S$) and having the restriction enzyme map of FIG. 1 is isolated from a sensitive strain. This gene has a nucleotide sequence represented by SEQ ID No. 17 in Sequence Listing. The amino acid sequence of a protein encoded by this gene, which is estimated on the basis of this nucleotide sequence, is the one represented by SEQ ID No. 18 in Sequence Listing. A comparison between the sequences of SEQ ID No. 17 and SEQ ID No. 15 reveals that a mutation from G to T occurs at the base at the position 1053, while a comparison between the sequences of SEQ ID No. 18 and SEQ ID No. 16 reveals that glycine at the residue 240 is converted into cysteine at the amino acid level, thus giving rise to the resistance.

Also, S. cerevisiae, which is sensitive to aureobasidin, is mutagenized with EMS and genomic libraries of two resistant strains thus obtained are prepared. From one of these libraries, a DNA fragment containing a resistant gene (scaur1$^R$) as a dominant mutant and having the restriction enzyme map of FIG. 2 is isolated, while a DNA fragment containing a resistant gene (scaur2$^R$) and having the restriction enzyme map of FIG. 3 is isolated from another library.

The nucleotide sequence of the coding region for the protein of the scaur1$^R$ gene is the one represented by SEQ ID No. 19 in Sequence Listing. The amino acid sequence of the protein encoded by this gene, which is estimated on the basis of the above nucleotide sequence, is the one represented by SEQ ID No. 20 in Sequence Listing. By the hybridization with the use of this resistant gene scaur1$^R$ as a probe, a DNA fragment containing a sensitive gene (scaur1$^S$) and having the restriction enzyme map of FIG. 2 is isolated from a sensitive strain. This gene has a nucleotide sequence represented by SEQ ID No. 21 in Sequence Listing. The amino acid sequence of a protein encoded by this gene, which is estimated on the basis of this nucleotide sequence, is the one represented by SEQ ID No. 22 in Sequence Listing. A comparison between the sequences of SEQ ID No. 21 and SEQ ID No. 19 reveals that a mutation from T to A occurs at the base at the position 852, while a comparison between the sequences of SEQ ID No. 22 and SEQ ID No. 20 reveals that phenylalanine at the residue 158 is converted into tyrosine at the amino acid level, thus giving rise to the resistance. The spaur1 gene has a 58% homology with the scaur1 gene at the amino acid level. Thus it is obvious that they are genes coding for proteins having similar functions to each other. When genes and proteins being homologous in sequence with the spaur1 and scaur1 genes and with the proteins encoded thereby are searched from a data base, none having a homology of 35% or above is detected. Accordingly, it is clear that these genes and the proteins encoded thereby are novel molecules which have never been known hitherto.

By the hybridization with the use of the DNA fragment of the resistant gene scaur2$^R$ as a probe, a DNA fragment containing a sensitive gene (scaur2$^S$) and having the restriction enzyme map of FIG. 3 is isolated from a sensitive strain.

The nucleotide sequence of this sensitive gene is the one represented by SEQ ID No. 23 in Sequence Listing and the amino acid sequence of the protein encoded by this gene, which is estimated on the basis of this nucleotide sequence, is the one represented by SEQ ID No. 24 in Sequence Listing. As the result of the homology search with the scaur2$^S$ gene and the protein encoded thereby, it has been found out that cystic fibrosis transmembrane conductance regulator (CFTR) of mammals alone has a homology as low as 31%. Compared with this CFTR, however, the part having a high homology is limited to the region around the domain of the nucleotide binding. It is therefore obvious that the protein encoded by the scaur2$^S$ gene is a protein which is completely different from CFTR in function and has never been known hitherto.

In order to prove the importance of the aur1 gene in the growth of cells, genes for disrupting the aur1 as shown in FIG. 4 and FIG. 5, in which genes coding for orotidine-5'-phosphate decarboxylase (ura4$^+$ in the case of Schizo. pombe, while URA3 in the case of S. cerevisiae) have been introduced midway in the aur1 gene, are prepared. When these aur1 disrupted genes are introduced into Schizo. pombe and S. cerevisiae respectively, the cells having the aur1 disrupted genes cannot grow at all. Thus it has been revealed that these genes and the proteins encoded thereby are essentially required for the growth of the yeast cells.

As the above examples clearly show, a gene regulating aureobasidin sensitivity can be isolated by using a organism having sensitivity to aureobasidin as a starting material and by carrying out the cloning with the use of various mutagenesis methods and/or screening methods depending on the organisms or the methods. Also, genes being hybridizable with the above-mentioned genes are involved in the scope of the first invention of the present invention. A gene regulating aureobasidin sensitivity can be isolated by the following method. The genomic DNA library of an organism having sensitivity to aureobasidin is integrated into, for example, a high-expression vector of a yeast and transformed into the yeast. Then a clone having aureobasidin resistance is selected from the transformants and DNA is recovered from this clone. Thus the resistant gene can be obtained. As a matter of course, genes obtained by modifying some part of the gene regulating aureobasidin sensitivity thus obtained by some chemical or physical methods are involved in the scope of the first invention of the present invention.

The second invention of the present invention relates to a process for cloning a gene regulating aureobasidin sensitivity which is characterized by using the gene regulating aureobasidin sensitivity of the first invention of the present invention or a part thereof as a probe. Namely, by screening, by the hybridization method or the polymerase chain reaction (PCR) method with the use of a part (consisting of at least 15 oligonucleotides) or the whole of the gene as obtained above, a gene coding for a protein having a similar function can be isolated.

For example, a pair of primers of SEQ ID No. 25 and SEQ ID No. 26 in Sequence Listing are synthesized on the basis of the DNA nucleotide sequence of the spaur1$^R$ gene represented by SEQ ID No. 15. Then PCR is performed by using cDNA of C. albicans, which is a pathogenic fungus, as a template with the use of the above-mentioned primers. The PCR is carried out and the PCR products are electrophoresed on an agarose gel and stained with ethidium bromide. In FIG. 6, the lanes 1, 2 and 3 show the results obtained by using cDNA of C. albicans, cDNA of S. cerevisiae and cDNA of Schizo. pombe as a template, respectively. As shown in FIG. 6, a certain DNA fragment is specifically amplified.

By screening the genomic DNA library of C. albicans with the use of this DNA fragment as a probe, a DNA molecule having a gene (caaur1), which has the same function as that of the spaur1 and scaur1 genes and having the restriction enzyme map of FIG. 7 is obtained. The nucleotide sequence of this caaur1 gene is the one represented by SEQ ID No. 27 in Sequence Listing and the amino acid sequence of the protein encoded by this gene, which has been estimated on the basis of the above nucleotide sequence, is the one represented by SEQ ID No. 28 in Sequence Listing. It has a high homology with the proteins encoded by the spaur1 and scaur1 genes.

By screening the genomic DNA library of C. albicans with the use of a DNA fragment comprising the whole length or a part of the scaur2$^S$ gene represented by SEQ ID No. 23 in Sequence Listing as a probe, a DNA fragment containing gene (caaur2), which has the same function as that of the scaur2 gene, and having the restriction enzyme map of FIG. 8 is obtained. The nucleotide sequence of a part of this caaur2 gene is the one represented by SEQ ID No. 29 in Sequence Listing and the amino acid sequence of the region encoded by this gene, which has been estimated on the basis of this nucleotide sequence, is the one represented by SEQ ID No. 30 in Sequence Listing. It has a high homology with the corresponding region of the protein encoded by the scaur2 gene.

The third invention of the present invention relates to an oligonucleotide comprising 15 or more bases which serves as the above-mentioned nucleic acid probe and is hybridizable with the gene regulating aureobasidin sensitivity, for example, the DNA fragment having the restriction enzyme map as shown in FIG. 1, FIG. 2 or FIG. 3. This nucleic acid probe is usable in, for example, the hybridization in situ, the identification of a tissue wherein the above-mentioned gene can be expressed, and the confirmation of the presence of a gene or mRNA in various vital tissues. This nucleic acid probe can be prepared by ligating the above-mentioned gene or a gene fragment to an appropriate vector, introducing it into a bacterium, allowing it to replicate in the bacterium, extracting from a disrupted cell suspension, cleaving with a restriction enzyme capable of recognizing the vector-ligating site, electrophoresing and then excising from the gel. Alternatively, this nucleic acid probe can be constructed by the chemical synthesis with the use of a DNA synthesizer or gene amplification techniques by PCR on the basis of the nucleotide sequence of SEQ ID Nos. 15, 17, 19, 21, 23, 27, 29 or 35 in Sequence Listing. This nucleic acid probe can be labeled with a radioisotope or a fluorescent substance to thereby elevate the detection sensitivity during use.

The fourth invention of the present invention relates to an antisense DNA of the above-mentioned gene regulating aureobasidin sensitivity, while the fifth invention of the present invention relates to an antisense RNA thereof. The introduction of the antisense DNA or antisense RNA into cells makes it possible to control the expression of the gene regulating aureobasidin sensitivity.

As examples of the antisense DNA to be introduced, antisense DNAs corresponding to the genes regulating aureobasidin sensitivity of SEQ ID Nos. 15, 17, 19, 21, 23, 27, 29 or 35 in Sequence Listing and some parts thereof may be cited. SEQ ID No. 31 in Sequence Listing shows an example of this antisense DNA. It represents the sequence of an antisense DNA of the gene regulating aureobasidin sensitivity of SEQ ID No. 15 in Sequence Listing. A fragment obtained by appropriately cleaving some part of such an antisense DNA, and a DNA synthesized depending on such an antisense DNA sequence may be used as the antisense DNA.

As examples of the antisense RNA to be introduced, antisense RNAs corresponding to the genes regulating aureobasidin sensitivity of SEQ ID Nos. 15, 17, 19, 21, 23, 27, 29 or 35 in Sequence Listing and some parts thereof may be cited. SEQ ID No. 32 in Sequence Listing shows an example of this antisense RNA. It represents the sequence of an antisense RNA of the gene regulating aureobasidin sensitivity of SEQ ID No. 15 in Sequence Listing. A fragment obtained by appropriately cleaving some part of such an antisense RNA, an RNA synthesized depending on such an antisense RNA sequence, and an RNA prepared with RNA polymerase in an in vitro transcription system by using the DNA corresponding to the gene regulating aureobasidin sensitivity of SEQ ID No. 15 or SEQ ID No. 17 in Sequence Listing or a part thereof may be used as the antisense RNA.

These antisense DNA and antisense RNA may be chemically modified so as to prevent degradation in vivo or to facilitate passage through a cell membrane. A substance capable of inactivating mRNA, for example, ribozyme may be linked thereto. The antisense DNA and antisense RNA thus prepared are usable in the treatment of various diseases such as mycoses accompanied by an increase in the amount of mRNA coding for a protein regulating aureobasidin sensitivity.

The sixth invention of the present invention relates to a recombinant plasmid having a gene coding for a protein regulating aureobasidin sensitivity being integrated into an appropriate vector. For example, a plasmid, in which a gene regulating aureobasidin sensitivity gene has been integrated into an appropriate yeast vector, is highly useful as a selection marker gene, since a transformant can be easily selected thereby with the guidance of the chemical resistance by using aureobasidin.

Also, the recombinant plasmid can be stably carried by, for example, *Escherichia coli*. Examples of vectors which are usable in this case include pUC118, pWH5, pAU-PS, Traplex119 and pTV118. pAU-PS having the spaur1$^S$ gene integrated therein is named pSPAR1. pWH5 having the spaur1$^S$ gene integrated therein is named pSCAR1. pWHS having the scaur2$^R$ gene integrated therein is named pSCAR$^2$. Traplex119 vector having the caaur1 gene integrated therein is named pCAAR1. pTV118 vector having a part of the caaur2 gene integrated therein is named pCAAR2N. Each of these recombinant plasmids is transformed into *E. coli*. It is also possible to express these plasmids in an appropriate host. Such a gene is reduced exclusively into the open reading frame (ORF) to be translated into a protein by cleaving with an appropriate restriction enzyme, if necessary, and then bound to an appropriate vector. Thus an expression recombinant plasmid can be obtained. When *E. coli* is used as the host, plasmids such as pTV118 may be used as a vector for the expression plasmid. When a yeast is used as the host, plasmids such as pYES2 may be used as the vector. When mammalian cells are used as the host, plasmids such as pMAMneo may be used as the vector.

The seventh invention of the present invention relates to a transformant having the above-mentioned recombinant plasmid which has been introduced into an appropriate host. As the host, *E. coli*, yeasts and mammalian cells are usable. *E. coli* JM109 transformed by pSPAR1 having the spaur1$^S$ gene integrated therein has been named and designated as *Escherichia coli* JM109/pSPAR1 and deposited at National Institute of Bioscience and Human-Technology, Agency of Industrial Science and Technology (1-3, Higashi 1 chome Tsukuba-shi Ibaraki-ken 305, JAPAN), in accordance with the Budapest Treaty under the accession number FERM BP-4485. *E. coli* HB101 transformed by pSCAR1 having the scaur1$^S$ gene integrated therein has been named and designated as *Escherichia coli* HB101/pSCAR1 and deposited at National Institute of Bioscience and Human-Technology, Agency of Industrial Science and Technology in accordance with the Budapest Treaty under the accession number FERM BP-4483. *E. coli* HB101 transformed by pSCAR2 having the scaur2$^R$ gene integrated therein has been named and designated as *Escherichia coli* HB101/pSCAR2 and deposited at National Institute of Bioscience and Human-Technology, Agency of Industrial Science and Technology in accordance with the Budapest Treaty under the accession number FERM BP-4484. *E. coli* HB101 transformed by pCAAR1 having the caaur1$^S$ gene integrated therein has been named and designated as *Escherichia coli* HB101/pCAAR1 and deposited at National Institute of Bioscience and Human-Technology, Agency of Industrial Science and Technology in accordance with the Budapest Treaty under the accession number FERM BP-4482. *E. coli* HB101 transformed by pCAAR2N having a part of the caaur2 gene integrated therein has been named and designated as *Escherichia coli* HB101/pCAAR2N and deposited at National Institute of Bioscience and Human-Technology, Agency of Industrial Science and Technology in accordance with the Budapest Treaty under the accession number FERM BP-4481.

A transformant capable of expressing a protein regulating aureobasidin sensitivity can be obtained by transforming a expression recombinant plasmid into an appropriate host, as described above. For example, a yeast having a recombinant plasmid as shown in FIG. 9 introduced thereinto is usable for this purpose.

The eighth invention of the present invention relates to a process for producing a protein regulating aureobasidin sensitivity which comprises incubating a transformant according to the sixth invention of the present invention, which contains a gene coding for this protein, in an appropriate nutritional medium, allowing the expression of the protein, then recovering the protein from the cells or the medium and purifying the same. For the expression of the gene coding for this protein, *E. coli*, a yeast or mammalian cells are employed as a host. When the yeast having the recombinant plasmid of FIG. 9 is incubated in a medium containing galactose, for example, the protein regulating aureobasidin sensitivity which is encoded by the scaur1$^S$ gene can be expressed.

The ninth invention of the present invention relates to an isolated protein regulating aureobasidin sensitivity. As examples of such a protein, those encoded by the above-mentioned spaur1, scaur1, scaur2, caaur1 and caaur2 genes can be cited.

The spaur1$^S$ gene codes for a protein having an amino acid sequence represented by SEQ ID No. 18 in Sequence Listing, while the scaur1$^S$ gene codes for a protein having an amino acid sequence represented by SEQ ID No. 22 in Sequence Listing. By the northern hybridization with the use of a DNA fragment of the spaur1 gene as a probe, mRNAs are detected from a sensitive strain (FIG. 10). Thus the expression of the spaur1 gene is confirmed.

FIG. 10 is an autoradiogram showing the results of the northern hybridization wherein mRNAs obtained from cells of a sensitive strain of Schizo. pombe in the logarithmic growth phase (lane 1), cells of a resistant strain in the logarithmic growth phase (lane 2), cells of the sensitive strain in the stationary phase (lane 3) and cells of the resistant strain in the stationary phase (lane 4) are electrophoresed on a 1.2% agarose gel containing formaldehyde.

The tenth invention of the present invention relates to an antibody against the above-mentioned protein regulating aureobasidin sensitivity. For example proteins having amino acid sequences of SEQ ID Nos. 16, 18, 20, 22, 24, 28, 30 or 36 in Sequence Listing and peptides comprising some parts of these amino acid sequences may be used as an antigen. The former antigens can be prepared through the expression in a transformant followed by purification, while the latter antigens can be synthesized on, for example, a marketed synthesizer. The antibody is produced by the conventional method. For example, an animal such as a rabbit is immunized with the above-mentioned protein or a peptide fragment together with an adjuvant to thereby give a polyclonal antibody. A monoclonal antibody can be produced by fusing antibody-producing B cells, which have been obtained by immunizing with an antigen, with myeloma cells, screening hybridomas producing the target antibody, and incubating these cells. As will be described hereinafter, these antibodies are usable in the treatment and diagnosis for animal and human diseases in which the above-mentioned proteins participate, such as mycoses.

For example, a peptide corresponding to the part of the 103- to 113-positions in the amino acid sequence of SEQ ID No. 22 is synthesized on a synthesizer and then bound to a carrier protein. Then a rabbit is immunized therewith and thus a polyclonal antibody is obtained. In the present invention, keyhole limpet hemocyanin (KLH) is used as the carrier protein. Alternatively, bovine serum albumin and ovalbumin are usable therefor.

The eleventh invention of the present invention relates to a process for detecting a protein regulating aureobasidin sensitivity by using the above-mentioned antibody. The detection can be carried out by detecting the binding of the antibody to the protein or measuring the amount of binding. For example, the protein or the cells producing the same can be detected by treating with a fluorescence-labeled antibody and then observing under a fluorescence microscope. The amount of the antibody bound to the protein can be measured by various known methods. For example, S. cerevisiae cells are stained by the immunofluorescent antibody technique by using the above-mentioned antibody and a secondary antibody such as FITC-labeled anti-rabbit antibody. Thus it is clarified that the protein encoded by the scaur1 gene is distributed all over the cells. Further, a yeast having the recombinant plasmid of FIG. 9 introduced thereinto is incubated in a medium containing glucose or galactose. The cells thus obtained are disrupted with glass beads and proteins are solubilized. Then these proteins are separated by SDS-polyacrylamide gel electrophoresis (SDS-PAGE) and the western blotting is carried out in the conventional manner by using the above-mentioned polyclonal antibody and peroxidase-labeled anti-rabbit antibody. Consequently, the protein encoded by the scaur1 gene can be detected, as FIG. 11 shows.

FIG. 11 shows the results of the western blotting wherein the proteins prepared from the cells obtained by the incubation in the presence of glucose (lane 1) or galactose (lane 2) are subjected to SDS-PAGE. A main band binding to the polyclonal antibody of the present invention is detected at around 38 kDa.

The twelfth invention of the present invention relates to a process for detecting a gene regulating aureobasidin sensitivity, for example, mRNA at the expression of a protein, by using the above-mentioned oligonucleotide as a nucleic acid probe. This process is applicable to the diagnosis for various diseases, including mycoses, associated with an abnormal amount of mRNA coding for the protein. For example, nucleic acids are precipitated from disrupted cells and mRNA is hybridized with a radioisotope-labeled nucleic acid probe on a nitrocellulose membrane. The amount of binding can be measured by autoradiography (FIG. 10) or with a scintillation counter.

The thirteenth invention of the present invention relates to a process for efficient screening of a novel antimycotic by using the transformant of the seventh invention of the present invention or the protein regulating aureobasidin sensitivity of the ninth invention of the present invention. For example, a drug exerting its effect on the protein or the gene of the present invention can be efficiently found out through a comparison of the activity on a transformant containing a sensitive gene with the activity on a transformant containing a resistant gene or a comparison between the activities on transformants differing in expression level from each other. Also, the screening can be efficiently carried out by measuring the affinity for the protein of the present invention, for example, the activity of inhibiting the binding of radiolabeled-aureobasidin to the protein.

As the above-mentioned examples clearly show, a gene regulating the aureobasidin sensitivity corresponding to each organism or each method can be isolated by employing a starting material, which is an organism having the sensitivity to aureobasidin, and effecting cloning by conducting various mutagenesis and/or screening treatments in the same manner as the one described above. Moreover, genes hybridizable with these genes can be isolated. As a matter of course, it is possible to prepare modified genes by partly altering the genes regulating the aureobasidin sensitivity obtained above by chemical, physical or genetic engineering techniques.

In the present invention, an aureobasidin resistant gene refers to a gene which is capable of imparting the resistance to an antimycotic aureobasidin when integrated into a host fungus. This gene codes for a protein imparting an aureobasidin resistance.

The aureobasidin resistant gene is exemplified typically by the above-mentioned spaur1$^R$ and scaur1$^R$. Such a gene acts predominantly and the resistance conferred by this gene is selective to aureobasidin. That is to say, it does not cause any substantial change in the sensitivity to other drugs.

The aureobasidin resistant gene also involves genes which are hybridizable with spaur1$^R$ and scaur1$^R$ and impart the aureobasidin resistance to a host fungus (for example, genes prepared by partly altering the spaur1$^R$ or scaur1$^R$ gene by chemical, enzymatic, physical or genetic engineering techniques).

Furthermore, the aureobasidin resistant gene involves a gene coding for a protein, which has an amino acid sequence obtained by subjecting a protein (Aur1$^R$p) capable of imparting the aureobasidin resistance to at least one modification selected from replacement, insertion and deletion of amino acid residue(s) and shows the activity of imparting the aureobasidin resistance.

The replacement, insertion and deletion of amino acid residue(s) from Aur1$^R$p can be effected by a site-specific mutagenesis. A DNA coding for the isolated Aur1$^R$p or a DNA coding for the protein capable of imparting the aureobasidin sensitivity (Aur1$^S$p) can be easily modified by effecting at least one of the replacement, insertion and deletion of nucleotide(s) and thus a novel DNA coding for a mutant of Aur1$^R$p can be obtained. Regarding the replacement, insertion and deletion of amino acid residue(s), the conversion of the amino acid(s) is based on one which can be effected by genetic engineering techniques without deteriorating the biological activity. In order to appropriately effect the mutation on the residue at a specific site, the target codon is subjected to random mutagenesis and a mutant having the desired activity is screened from the ones thus expressed. The mutant obtained by insertion involves a fused protein wherein Aur1$^R$p or its fragment is bound to another protein or polypeptide at the amino terminal and/or the carboxyl terminal of the Aur1$^R$p or its fragment via a peptide bond. In order to delete amino acid residue(s), it is also possible to replace an arbitrary amino acid codon in the amino acid sequence with a termination codon by the gapped duplex method to thereby delete the region on the carboxyl terminal side of the replaced amino acid residue from the amino acid sequence. Alternatively, a DNA coding for a protein, from which the amino terminal and/or carboxyl terminal regions in an arbitrary length have been deleted, can be obtained by the deletion method comprising degrading the coding DNA from the region(s) corresponding to the amino terminal and/or the carboxyl terminal of the amino acid sequence [*Gene*, 33, 103–119 (1985)] or a PCR method with the use of primers containing an initiation codon and/or a termination codon. Known examples of the site-specific mutagenesis method include the gapped duplex method with the use of oligonucleotide(s) [*Methods in Enzymology*, 154, 350–367 (1987)], the uracil DNA method with the use of oligonucleotide(s) [*Methods in Enzymology*, 154, 367–382 (1987)], the nitrous acid mutation method [*Proc. Natl. Acad. Sci. USA*, 79, 7258–7262 (1982)] and the cassette mutation method [*Gene*, 34, 315–323 (1985)].

The present inventors have found out that Aur1$^S$p represented by SEQ ID No. 22 in the Sequence Listing can be converted into Aur1$^R$p by replacing the 240th residue Ala by another amino acid residue, thus completing the seventeenth and eighteenth inventions.

The Aur1$^R$p of the seventeenth invention is one wherein the 240th residue Ala of Aur1$^S$p represented by SEQ ID No. 22 in the Sequence Listing has been replaced by another amino acid residue. Other amino acid residues may be replaced, inserted or deleted by using chemical, physical or genetic engineering techniques, so long as the biological activity is not deteriorated thereby. The Aur1$^R$p of the seventeenth invention may be appropriately prepared through genetic engineering techniques by using a DNA coding for Aur1$^S$p represented by SEQ ID No. 47 in the Sequence Listing. Its biological activity can be assayed by measuring the activity of converting aureobasidin sensitive cells into resistant cells. The Aur1$^R$p of the seventeenth invention is one having an enhanced activity of converting aureobasidin sensitive cells into resistant cells compared with Aur1$^R$p represented by SEQ ID No. 20 in the Sequence Listing.

A preferable Aur1$^R$p is one having an enhanced activity of converting aureobasidin sensitive cells into resistant cells compared with Aur1$^R$p represented by SEQ ID No. 20 in the Sequence Listing. A DNA coding for this Aur1$^R$p can be appropriately used in the present invention.

In an example of particularly preferable embodiment of Aur1$^R$p, a mutant can be obtained by replacing the 240th residue Ala by Cys. The amino acid sequence of an example of such a mutant is shown in SEQ ID No. 42 in the Sequence Listing. This mutant is referred to as Aur1$^R$p (A240C). It is also possible to obtain a mutant wherein the 158th residue Phe and the 240th residue Ala of Aur1$^S$p have been replaced respectively by Tyr and Cys. The amino acid sequence of this mutant is shown in SEQ ID No. 43 in the Sequence Listing. This mutant is referred to as Aur1$^R$p (F158Y, A240C). Each of these mutants has a stronger ability to impart aureobasidin resistance than that of the protein represented by SEQ ID No. 40 in the Sequence Listing [Aur1$^R$p (F158Y)] wherein the 158th residue Phe of Aur1$^S$p has been replaced by Tyr.

The aureobasidin resistant gene to be used in the present invention is exemplified by the DNAs represented by SEQ ID Nos. 44 to 46 in the Sequence Listing. The DNA represented by SEQ ID No. 46 in the Sequence Listing is one coding for Aur1$^R$p (F158Y), the DNA represented by SEQ ID No. 44 in the Sequence Listing is one coding for Aur1$^R$p (A240C), and the DNA represented by SEQ ID No. 45 in the Sequence Listing is one coding for Aur1$^R$p (F158Y, A240C).

A replication plasmid can be prepared by integrating a gene, which coded for a protein regulating the aureobasidin sensitivity, into an appropriate vector. For example, a plasmid prepared by integrating an aureobasidin resistant gene into an appropriated yeast vector is highly useful as a selective marker gene, since a transformant can be easily selected thereby depending on the drug resistance with the use of aureobasidin. As the vector for yeasts, use can be made of ones of YR$_p$, YC$_p$, YE$_p$ and YI$_p$ types.

Also, the replication plasmid can be stably carried by, for example, *Escherichia coli,* as described above. Examples of vectors which are usable in this case include pUC118, pWH5, pAU-PS, Traplex119 and pTV118.

The integration vector containing the aureobasidin resistant gene of the present invention is a linear vector which can be usually prepared by cleaving a replication plasmid containing the aureobasidin resistant gene into a linear form. The cleavage point in the replication plasmid will be described hereinbelow.

FIG. 13 shows a process wherein an aureobasidin resistant gene in a chromosome integration vector undergoes homologous recombination with the host chromosome being homologous therewith (i.e., an aureobasidin sensitive gene) and thus aureobasidin sensitive cells are converted into aureobasidin resistant cells. A replication plasmid containing the aureobasidin resistant gene is cleaved into a linear form at one position in the aureobasidin resistant gene sequence with an appropriate restriction enzyme. The vector thus linearized undergoes homologous recombination with the aureobasidin sensitive gene in the host chromosome being homologous therewith. Thus the aureobasidin resistance is imparted to the host cells. When the replication plasmid contains a foreign gene, then the aureobasidin resistance and the foreign gene are imparted to the host cells. For example, a replication vector pAUR1aare for preparing a linear vector, which contains scaur1$^R$ and human acylamino acid releasing enzyme (AARE) described in Japanese Patent Laid-Open No. 254680/1991, is prepared. *Escherichia coli* JM109 strain having this vector introduced therein was named and indicated as *Escherichia coli* JM109/pAUR1aare and has been deposited at National Institute of Bioscience and Human-Technology, Agency of Industrial Science and Technology under the accession number FERM P-14366. To linearize a replication vector, use can be effectively made of a restriction enzyme cleavage site which exists not in the target foreign gene moiety but in the aureobasidin resistant gene. In the cases of, for example, scaur1$^R$ originating in *S. cerevisiae* and spaur1$^R$ originating in Schizo. pombe, restriction enzyme sites of StuI, etc. and BalI, etc. are usable respectively.

In a preferable form, the vector of the present invention may contain an aureobasidin resistant gene and a foreign gene and other genes originating in replication vectors may be eliminated therefrom. Promoters, terminators, etc. for expressing the aureobasidin resistant gene and the foreign gene may be selected depending on the characters of the host. As a matter of course, the promoter parts of the DNAs represented by SEQ ID Nos. 15 and 19 in the Sequence Listing can be used as a promoter for expressing the function of the aureobasidin resistant gene. In the case of *S. cerevisiae*, use can be made of, for example, promoters of alcohol dehydrogenase gene (ADH1) and glyceraldehyde-3-phosphate dehydrogenase gene (GPD) and the terminator of cytochrome C1 gene (CYC1). These promoters and terminators may be different from those for expressing the aureobasidin resistant gene.

In the present invention, the term "foreign gene" refers to a gene which is foreign to the host fungal cells, i.e., an alien gene. Examples thereof include a nonfungal gene, a modified gene, a gene of a fungal species different from the host and a self-cloned gene. More particularly, genes participating in fermentation, alcohol resistance, saccharification and the formation of taste components or aroma components fall within this category.

The fifteenth invention relates to a process for producing an aureobasidin resistant transformant. An aureobasidin resistant transformant can be created by, for example, preparing a replication vector containing the above-mentioned aureobasidin resistant gene, cleaving it at one position in the aureobasidin resistant gene in the replication vector to give a linear chromosome integration vector for a host fungus, adding this vector to aureobasidin sensitive host fungal cells under such conditions as to allow the transformation of the fungal cells, thus integrating the vector into the host chromosome, incubating the transformant in a medium suitable for the proliferation of the host cells containing the antibiotic aureobasidin, and screening the aureobasidin resistant transformant thus proliferating. The transformation may be effected in accordance with publicly known methods such as the protoplast generation procedure, the lithium acetate procedure or the electroporation procedure. The medium to be used herein is not particularly restricted, so long as it is usable in the proliferation of fungi. Examples of such a medium commonly employed include Sabouraud's dextrose medium, a YPD medium, a czapek medium and a YNBG medium. The concentration of the aureobasidin added varies depending on the host fungal cells having the sensitivity and usually ranges from 0.05 to 80 µg/ml.

The transformant of the sixteenth invention can be obtained by the process of the fifteenth invention.

As an example of the transformant according to the present invention, Sake yeast Kyokai K-701 having scaur1$^R$ and AARE gene integrated into the chromosome has been deposited at National Institute of Bioscience and Human-Technology, Agency of Industrial Science and Technology under the accession number FERM P-1437. The transformant thus obtained by using the chromosome integration vector of the present invention has an aureobasidin resistance imparted thereto and the foreign gene integrated thereinto which is held on the chromosome in a stable state. These characteristics make it highly useful in industrial uses, etc.

The Aur1$^R$p of the seventeenth invention can impart the aureobasidin resistance to monoploid yeasts and diploid yeasts, in particular, practically usable ones. Namely, it is highly useful in breeding *S. cerevisiae* which has been widely applied to liquors such as sake, shochu, beer and wine and fermented foods such as bread. Further, the Aur1$^R$p of the seventeenth invention is applicable to fungi other than *S. cerevisiae* and useful in, for example, breeding and genetic engineering application of other fungi.

For example, the Aur1$^R$p of the seventeenth invention is capable of imparting the aureobasidin resistance to *C. albicans*. A vector having the DNA coding for this Aur1$^R$p is the first vector for genetic engineering uses provided for *C. albicans*.

It is known that *C. albicans* is a fungus causative of mycosis. With the recent increase in opportunistic infection, it has been needed to conduct studies for clarifying the causes of the pathogenicity. The Aur1$^R$p of the seventeenth invention and the above-mentioned vector are highly useful in genetic studies on *C. albicans*.

The present inventors have further found out that molds such as *Aspergillus nidulans* (hereinafter referred to simply as *A. nidulans*) and *Aspergillus fumigatus* (hereinafter referred to simply as *A. fumigatus*) are sensitive to aureobasidin. Thus we have mutated sensitive cells of *A. nidulans* into resistant cells and succeeded in the isolation of a gene capable of imparting the resistance to aureobasidin (a resistant gene) from the corresponding resistant cells. Further, we have disclosed the existence of a protein encoded by this gene. We have also successfully found novel genes regulating aureobasidin sensitivity from aureobasidin sensitive *A. nidulans* and *A. fumigatus* by using a DNA fragment of the above-mentioned gene as a probe. Furthermore, we have found out that the detection of this gene enables the diagnosis of diseases caused by these cells (for example, mycosis caused by fungi) and that the antisense DNA or antisense RNA, which inhibits the expression of the gene regulating aureobasidin sensitivity characteristic of the cells, is usable as a remedy for diseases caused by these cells (for example, an antimycotic for mycosis).

The term "a protein regulating aureobasidin sensitivity" as used herein means a protein which is contained in an organism, in particlar a mold, showing a sensitivity to aureobasidin. This protein is required for achieving a sensitivity or resistance to aureobasidin. The term "a gene regulating aureobasidin sensitivity" means a gene which encodes such a protein regulating aureobasidin sensitivity and a sensitive gene and a resistant gene fall within this category. The aureobasidin sensitivity of an organism varies depending on the molecular structure or amount of such a protein or gene regulating aureobasidin sensitivity carried by the organism.

The term "a functional derivative of the protein or gene regulating aureobasidin sensitivity" as used herein means one which has a biological activity substantially comparable to that of the protein or DNA regulating aureobasidin sensitivity. It include fragments, variants, mutants, analogs, homologs and chemical derivatives. A variant means one which is substantially analogous to the whole protein or a fragment originating therein in structure and/or function. That is to say, one molecule which is essentially analogous to another in activity is regarded as a mutant, even though these two molecules are different in molecular structure or amino acid sequence from each other. The functional derivatives include proteins showing an amino acid sequence with at least one modification selected from among replacement, insertion and deletion of amino acid residue(s) and having a comparable biological activity and genes encoding these. The protein regulating aureobasidin sensitivity may be subjected to the replacement, insertion and deletion of amino acid residues by a site-specific mutagenesis. The isolated DNA encoding the protein regulating aureobasidin sensitivity can be easily subjected to at least one modification selected from among replacement, insertion and deletion of nucleotides and thus a novel DNA encoding the protein regulating aureobasidin sensitivity and its functional derivatives can be obtained.

Regarding the replacement, insertion and deletion of amino acid residues, one or more amino acids can be converted by genetic engineering techniques and those suffering from no injury to the biological activity should be selected. To properly effect a mutation on the residue at a specified site, mutagenesis is performed at random on the target codon and a mutant having the desired activity is screened from the ones thus expressed. The mutant obtained by insertion involves a fused protein wherein the protein regulating aureobasidin sensitivity or its functional derivative or a fragment thereof is bound via a peptide bond to another protein or polypeptide at the amino terminal and/or the carboxy terminal of the protein regulating aureobasidin sensitivity or its functional derivative or a fragment thereof. To delete amino acid residue(s), an arbitrary amino acid codon in the amino acid sequence may be replaced by a termination codon by the site-specific mutagenesis. Thus the region on the carboxy terminal side of the replaced amino acid residue can be deleted from the amino acid sequence. Alternatively a DNA coding for a protein, from which the amino terminal and/or carboxy terminal regions in an arbitral length have been deleted, can be obtained by the deletion method comprising degrading a coding DNA from the region(s) corresponding to the amino terminal and/or the carboxy terminal of the amino acid sequence [*Gene, 33,* 103–119 (1985)] or a PCR method with the use of primers containing an initiation codon and/or a termination codon. Known examples of the site-specific mutagenesis method include the gapped duplex method with the use of oligonucleotide(s) [*Methods in Enzymology, 154,* 350–367 (1987)], the uracil DNA method with the use of oligonucleotide(s) [*Methods in Enzymology, 154,* 367–382 (1987)], the nitrous acid mutation method [*Proc. Natl. Acad. Sci. USA, 79,* 7258–7262 (1982)] and the cassette mutation method [*Gene, 34,* 315–323 (1985)].

The nineteenth invention relates to a gene regulating aureobasidin sensitivity obtained from a mold exemplified by one belonging to the genus Aspergillus or its functional derivative. In order to isolate this gene, aureobasidin sensitive cells are first subjected to a mutagenesis to thereby derive a resistant strain therefrom. Then a DNA library is prepared from the chromosome DNAs or cDNAs of this resistant strain and a gene capable of imparting the resistance (a resistant gene) is cloned from this library. Similarly, a DNA library of a sensitive strain is prepared and DNA molecules hybridizable with the resistant gene are isolated and cloned. Thus a sensitive gene can be isolated.

The mutagenesis is performed by, for example, treating with a chemical such as ethylmethane sulfonate (EMS) or N-methyl-N'-nitro-N-nitro-soguanidine (NTG) or by ultraviolet or other radiation. A mutant that has acquired the resistance can be screened by culturing the mutagenized cells in a nutritional medium containing aureobasidin at an appropriate concentration under appropriate conditions. The resistant strain thus obtained may vary depending on the method and conditions selected for the mutagenesis. It is further possible to select strains differing in the extent of resistance by varying the aureobasidin concentration at the screening. It is also possible to select a temperature-sensitive resistant strain by varying the temperature at the screening. Since there are two or more mechanisms of the resistance to aureobasidin, two or more resistant genes can be isolated by genetically classifying these resistant strains.

The genes regulating aureobasidin sensitivity of molds belonging to the genus Aspergillus of the present invention include a gene anaurl$^R$ isolated from a resistant mutant of *A. nidulans,* a gene anaurl$^S$ isolated from a sensitive strain of *A. nidulans* and a gene afaurl$^S$ isolated from a sensitive strain of *A. fumigatus.*

The attached FIG. 15 shows the restriction enzyme map of the genomic DNA of the gene anaurl$^R$ regulating aureobasidin sensitivity and originating in a mold of Aspergillus, FIG. 16 shows the restriction enzyme map of the cDNA of the gene anaurl$^S$ and FIG. 17 shows the restriction enzyme map of the cDNA of the gene afaurl$^S$.

*A. nidulans* sensitive to aureobasidin is mutagenized by UV irradiation and a genomic library of the resistant strain thus obtained is prepared. From this library, a DNA fragment containing a resistant gene (anaurl$^R$) and having the restriction enzyme map of FIG. 15 is isolated. This gene has a DNA sequence represented by SEQ ID NO. 1 in the Sequence Listing. The amino acid sequence of a protein encoded by this gene, which is estimated on the basis of this DNA sequence, is the one represented by SEQ ID NO. 2 in the Sequence Listing. By the hybridization with the use of this resistant gene, a cDNA fragment containing a sensitive gene (anaurl$^S$) and having the restriction enzyme map of FIG. 16 is isolated from a cDNA library of a sensitive strain. This sensitive gene has a DNA sequence represented by SEQ ID NO. 3 in the Sequence Listing. The amino acid sequence of a protein encoded by this gene, which is estimated on the basis of this base sequence, is the one represented by SEQ ID NO. 4 in the Sequence Listing. A comparison between the sequences of SEQ ID NO. 3 and SEQ ID NO. 1 reveals that the genomic DNA has one intron (intervening sequence) ranging from the base at the position 1508 to the one at the position 1563 in SEQ ID NO. 1. Further, G at the position 1965 in SEQ ID NO. 1 has been mutated into T. A comparison between the sequences of SEQ ID NO. 4 and SEQ ID NO. 2 reveals that the amino acid glycine at the position 275 has been mutated into valine at the amino acid level, thus giving the resistance. The nineteenth invention also involves genes constructed by chemically or physically altering a part of the genes of the present invention which regulate aureobasidin sensitivity and originate in molds.

The twentieth invention relates to a method for cloning a gene regulating aureobasidin sensitivity and originating in a mold such as one of the genus Aspergillus or its functional derivative. This method comprises using the gene of the nineteenth invention regulating aureobasidin sensitivity and originating in a mold, its functional derivative, or a part of the same as a probe. That is to say, a gene encoding a protein having a comparable function can be isolated by the hybridization method or the polymerase chain reaction (PCR) method with the use of the whole or a part of the gene (consisting of at least 15 oligonucleotides) obtained above as a probe.

To examine a region appropriately usable as the above-mentioned probe, the present inventors have compared the amino acid sequence of the protein encoded by the gene anaur1$^S$ of the present invention (SEQ ID NO. 4 in the Sequence Listing) and the amino acid sequence of the protein encoded by the gene afaur1$^S$ of the present invention (SEQ ID NO. 5 in the Sequence Listing) with the amino acid sequence of the protein encoded by an aureobasidin sensitive gene (scaur1$^S$) originating in *S. cerevisiae* (SEQ ID NO. 6), the amino acid sequence of the protein encoded by another aureobasidin sensitive gene (spaur1$^S$ originating in *Schizo. pombe* (SEQ ID NO. 7) and the amino acid sequence of the protein encoded by a gene regulating aureobasidin sensitivity (caaur1) originating in *C. albicans* (SEQ ID NO. 8), each described in Canadian Patent No. 2124034. As a result, no homology is observed as the whole. However, it has been revealed for the first time that there is a characteristic sequence having been conserved in common in these heterogenous genes regulating aureobasidin sensitivity. This conversed sequence has been very well conserved (homology: 80% or above) and is composed of at least eight amino acid residues, which corresponds to a sufficiently long length to be used as a probe. FIG. 18 shows a comparison among the amino acid sequences represented by SEQ ID NOs. 4 to 8 wherein three sequences (Box-1 to Box-3) named "Box sequences" by the inventors correspond to the conserved sequence. Thus, a gene regulating aureobasidin sensitivity and originating in mold or its functional derivative can be cloned by using a primer or a probe constructed from the amino acid sequence of Box 1, 2 or 3 respectively represented by SEQ ID NOs. 9, 10 or 11 in the Sequence Listing.

The amino acid sequences given in five rows in FIG. 18 correspond respectively to SEQ ID NO. 4 (the top row), SEQ ID NO. 5 (the second row), SEQ ID NO. 6 (the third row), SEQ ID NO. 7 (the fourth row) and SEQ ID NO. 8 (the bottom row).

The target gene encoding the protein regulating aureobasidin sensitivity or its functional derivative may be obtained by hybridization in, for example, the following manner. First, chromosomal DNAs obtained from the target gene source or cDNAs constructed from mRNAs with the use of a reverse transcriptase are connected to a plasmid or a phage vector in accordance with the conventional method and introduced into a host to thereby prepare a library. After incubating this library on a plate, the colonies or plaques thus formed are transferred onto a nitrocellulose or nylon membrane and the DNAs are denatured and thus immobilized on the membrane. This membrane is incubated in a solution containing a probe which has been preliminarily labeled with radio isotope $^{32}$p, etc. (The probe to be used herein may be a gene encoding the amino acid sequence represented by SEQ ID NO. 4 in the Sequence Listing or a part of the same. For example, use can be made of the gene represented by SEQ ID NO. 3 in the Sequence Listing or a part of the same. It is appropriate to use therefor a base sequence which is composed of at least 15 bases and encodes one of the amino acid sequences represented by SEQ ID NOs. 9 to 11 in the Sequence Listing or a part of the same.) Thus DNA hybrids are formed between the DNAs on the membrane and the probe. For example, the membrane having the DNAs immobilized thereon is hybridized with the probe in a solution containing 6×SSC, 1% of sodium lauryl sulfate, 100 µg/ml of salmon sperm DNA and 5×Denhardt's solution (containing bovine serum albumin, polyvinylpyrolidone and Ficoll each at a concentration of 0.1%) at 65° C. for 20 hours. After the completion of the hybridization, nonspecifically adsorbed matters are washed away and clones forming hybrids with the probe are identified by autoradiography, etc. Into the clone thus obtained, a gene encoding the target protein has been included.

It is confirmed whether or not the obtained gene is the one encoding the target protein regulating aureobasidin sensitivity or its functional derivative, after the DNA sequence of the obtained gene is identified by, for example, the following method.

A clone obtained by the hybridization may be sequenced in the following manner. When the recombinant all is *Escherichia coli*, it is incubated in a test tube, etc. and the plasmid is extracted by a conventional method. Then it is cleaved with restriction enzymes and an insert thus excised therefrom is subcloned into an M13 phage vector, etc. Next, the base sequence is identified by the dideoxy method. When the recombinant is a phage, the base sequence can be identified fundamentally by the same steps. These fundamental experimental procedures to be used from the cell culture to the DNA sequencing are described in, for example, *Molecular Cloning, A Laboratory Manual,* T. Maniatis et al., Cold Spring Harbor Laboratory Press (1982).

To confirm whether or not the obtained gene is the one encoding the target protein regulating aureobasidin sensitivity or its functional derivative, the amino acid sequence thus identified is compared with the amino acid sequence represented by SEQ ID No. 4 in the Sequence Listing to thereby know the protein structure and amino acid sequence homology.

To examine whether or not the obtained gene sustains a sensitivity or resistance to aureobasidin, the obtained gene is transformed into sensitive cells and the aureobasidin sensitivity of the transformed cells thus obtained is determined to thereby reveal the activity of the gene. Alternatively, the activity can be determined by transforming the obtained gene into cells from which the activity has been eliminated by disrupting or mutating the gene regulating aureobasidin sensitivity. It is preferable that the above-mentioned gene to be transformed contains sequences required for the expression (promoter, terminator, etc.) in the upstream and/or downstream of the gene so as to enable the expression in the cells transformed.

When the obtained gene fails to contain the whole region encoding the protein regulating aureobasidin sensitivity or its functional derivative, the base sequence of the whole region encoding the protein regulating aureobasidin sensitivity or its functional derivative which is hybridizable with the gene of the present invention encoding the protein regulating aureobasidin sensitivity or its functional derivative can be obtained by preparing synthetic DNA primers on the basis of the gene thus obtained, amplifying the missing region by PCR or further screening a DNA library or a cDNA library with the use of a fragment of the obtained gene as a probe.

For example, a cDNA molecule having the restriction enzyme map of FIG. 17, which contains a gene (afaur1$^s$) of *A. fumigatus* being comparable in function to the gene anaur1$^s$, can be obtained by screening a cDNA library of a pathogenic fungus *A. fumigatus* with the use of a DNA fragment of the PstI-EcoRI fragment (921 bp) of FIG. 16 as a probe. This gene has a base sequence represented by SEQ ID NO. 12 in the Sequence Listing and the amino acid sequence of a protein encoded by this gene, which is estimated on the basis of this base sequence, is the one represented by SEQ ID NO. 5 in the Sequence Listing. When the genes anaur1$^s$ and afaur1$^s$ are compared, a homology of 87% is observed at the amino acid level. Further, genomic DNAs prepared from *Aspergillus niger* (hereinafter referred to simply as *A. niger*) and *Aspergillus oryzae* (hereinafter referred to simply as *A. oryzae*) are subjected to the Southern blotting analysis with the use of a DNA fragment of the gene anaur1$^s$ as a probe. As a result, it is revealed that genes regulating aureobasidin sensitivity occur in *A. niger* and *A. oryzae*. It is also possible to isolate genes regulating aureobasidin sensitivity from molds other than those belonging to the genus Aspergillus, for example, ones of the genus Penicillium.

The twenty-first invention relates to the above-mentioned nucleic acid probe, i.e., an oligonucleotide which is composed of at least 15 bases and hybridizable with a gene regulating aureobasidin sensitivity, for example, a DNA fragment having a restriction enzyme map of FIGS. 15, 16 or 17.

This nucleic acid probe is applicable to in situ hybridization, the confirmation of a tissue wherein the above-mentioned gene is expressed, the confirmation of the existence of a gene or mRNA in various vital tissues, etc. This nucleic acid probe can be prepared by ligating the above-mentioned gene or its fragment to an appropriate vector, introducing it into a bacterium followed by replication, extracting with phenol, etc. from a disrupted cell solution, cleaving with restriction enzymes capable of recognizing the ligation site with the vector, electrophoresing and excising from the electrophoresis gels.

Alternatively, this nucleic acid probe can be prepared by a chemical synthesis with the use of a DNA synthesizer or gene amplification techniques by PCR on the basis of each of the base sequences represented by SEQ ID NOs. 1, 3 and 12 in the Sequence Listing. Examples of sequences appropriately usable as this nucleic acid probe include base sequences which are composed of at least 15 bases and encode the amino acid sequences represented by SEQ ID NOs. 9 to 11 in the Sequence Listing or a part of the same. To elevate the detection sensitivity, the nucleic acid probe may be labeled with a radioisotope or a fluorescent substance.

The twenty-second invention relates to the antisense DNA of the above-mentioned gene regulating aureobasidin sensitivity and originating in a mold, while the twenty-third invention relates to the antisense RNA thereof. By introducing this antisense DNA or antisense RNA into cells, the expression of the gene regulating aureobasidin sensitivity can be controlled.

As the antisense DNA to be introduced, use can be made of, for example, the corresponding antisense DNAs of the genes regulating aureobasidin sensitivity represented by SEQ ID NOs. 1, 3 and 12 in the Sequence Listing or a part of the same. SEQ ID NO. 13 in the Sequence Listing shows an example of such an antisense DNA which corresponds to the sequence of the antisense DNA of the gene regulating aureobasidin sensitivity represented by SEQ ID NO. 1 in the Sequence Listing. As the antisense DNA, it is also possible to use fragments obtained by appropriately cleaving these antisense DNAs or DNAs synthesized on the basis of the sequences of these antisense DNAs.

As the antisense RNA to be introduced, use can be made of, for example, the corresponding antisense RNAs of the genes regulating aureobasidin sensitivity represented by SEQ ID NOs. 1, 3 and 12 in the Sequence Listing or a part of the same. SEQ ID No. 14 in the Sequence Listing shows an example of such an antisense RNA which corresponds to the sequence of the antisense RNA of the gene regulating aureobasidin sensitivity represented by SEQ ID NO. 1 in the Sequence Listing. As the antisense RNA, it is also possible to use fragments obtained by appropriately cleaving these antisense RNAs or RNAs synthesized on the basis of the sequences of these antisense RNAs. For example, use can be made of an RNA prepared by using the corresponding antisense RNA of the gene regulating aureobasidin sensitivity represented by SEQ ID NO. 1 or 3 in the Sequence Listing and treating it with RNA polymerases in an in vitro transcription system.

The antisense DNA and antisense RNA can be chemically modified so as to make them hardly degradable in vivo and enable them to pass through cell membrane. A substance capable of inactivating mRNA such as a ribozyme may be bound thereto. The antisense DNA and antisense RNA thus prepared are usable in the treatment of various diseases such as mycosis in association with an increase in the content of the mRNA which encodes the gene regulating aureobasidin sensitivity or its functional derivative.

The twenty-fourth invention relates to a recombinant plasmid wherein the gene of the nineteenth invention, which encode a protein regulating aureobasidin sensitivity or its functional derivative and originates in a mold, has been integrated into an appropriate vector. For example, a plasmid wherein an aureobasidin resistant gene has been integrated into an appropriate yeast vector is highly useful as a selective marker gene, since it makes it easy to select a transformant showing the drug resistance against aureobasidin.

Also, a recombinant plasmid can be stably carried by *Escherichia coli*, etc. Examples of the vector usable therefor include pUC118, pWH5, pAU-PS, Traplex119 and pTB118.

It is also possible to transform a mold by ligating the gene of the nineteenth invention which encodes a protein regulating aureobasidin sensitivity or its functional derivative and originates in a mold to an appropriate vector. When a plasmid such as pDHG25 [Gene, 98, 61–67 (1991)] is employed as the vector, the DNA introduced into the mold can be maintained therein in the state of the plasmid. When a plasmid such as pSa23 [Agricultural and Biological Chemistry, 51, 2549–2555 (1987)] is employed as a vector, the DNA can be stably maintained in the state of having been integrated into the chromosome of the mold. It is furthermore possible to give a recombinant plasmid for gene expression by reducing the gene of the present invention into the open reading frame (ORF) alone by cleaving it with appropriate restriction enzymes and by ligating it to an appropriate vector. To construct the plasmid for expression, use can be made of a plasmid such as pTV118, etc. (when *Escherichia coli* is employed as the host), pYE2, etc. (when a yeast is employed as the host), pMAMneo, etc. (when mammal cells are employed as a host) or pTAex3, etc. (when a mold is employed as the host) as the vector.

The twenty-fifth invention relates to a transformant obtained by introducing the above-mentioned recombinant plasmid into an appropriate host. As the host, use can be made of *Escherichia coli*, yeasts, molds and mammal cells. *Escherichia coli* JM109 transformed by a plasmid pANAR1 which had the gene anaur1$^s$ integrated thereinto was named *Escherichia coli* JM109/pANAR1 and has been deposited at National Institute of Bioscience and Human-Technology, Agency of Industrial Science and Technology under the accession number FERM BP-5180.

The twenty-sixth invention relates to a process for producing a protein regulating aureobasidin sensitivity or its functional derivative. This process comprises incubating a transformant having the recombinant expression plasmid of the twenty-fourth invention, which contains a gene encoding this protein or its functional derivative, in an appropriate nutritional medium, recovering and purifying the protein thus expressed from the cells or the medium. To express the gene encoding this protein, use is made of *Escherichia coli*, a yeast, a mold or mammal cells as the host.

The twenty-seventh invention relates to a protein regulating aureobasidin sensitivity or its functional derivative. Examples thereof include those encoded by the above-mentioned genes anaur1$^R$, anaur1$^s$ and afaur1$^s$ and having amino acid sequences represented respectively by SEQ ID NOs. 2, 4 and 5.

As a matter of course, these proteins may have at least one modification selected from among replacement, insertion and deletion by chemical, physical or genetic engineering techniques. It is also possible to construct an antibody against a protein regulating aureobasidin sensitivity by using the proteins having the amino acid sequences represented by SEQ ID NOs. 2, 4 and 5 or a peptide fragment of a region corresponding to a part of such an amino acid sequence as an antigen.

The twenty-eighth invention relates to a protein capable of imparting aureobasidin resistance wherein at least the amino acid Gly at the position 275 in the gene imparting aureobasidin sensitivity represented by SEQ ID NO. 4 in the Sequence Listing has been replaced by another amino acid. This invention also involves functional derivatives of the same obtained by introducing at least one modification selected from among replacement, insertion and deletion by chemical, physical or genetic engineering techniques thereinto without any injury to the biological activity thereof. The protein of the present invention capable of imparting aureobasidin resistance may be appropriately prepared genetic engineeringly by using DNAs encoding the proteins capable of imparting aureobasidin resistance represented by SEQ ID NOs. 3 and 12 in the Sequence Listing. Its biological activity can be determined by measuring the activity thereof of converting aureobasidin sensitive cells into aureobasidin resistant cells.

The twenty-ninth invention relates to a DNA encoding the protein of the twenty-eighth invention capable of imparting aureobasidin resistance. It also involves DNAs obtained by introducing at least one modification selected from among replacement, insertion and deletion of nucleotide(s) into the above-mentioned DNA. Such a modification may be easily effected by a site-specific mutagenesis. These modified DNAs are employed in order to produce mutated proteins.

The thirtieth invention relates to a method for detecting a gene regulating aureobasidin sensitivity by hybridization with the use of a nucleic acid probe. Examples of the nucleic acid probe usable herein include oligonucleotides which are composed of at least 15 bases and hybridizable selectively with the DNAs represented by SEQ ID NOs. 1, 3 and 12 in the Sequence Listing and fragments thereof. It is appropriate to use therefor base sequences which encode the amino acid sequences represented by SEQ ID NOs. 9 to 11 in the Sequence Listing or a part of the same and consist of at least 15 bases. By using such a nucleic acid probe, DNAs or RNAs extracted from the target organism are subjected to Southern hybridization or Northern hybridization to thereby give the gene of the target organism regulating aureobasidin sensitivity. The nucleic acid probe is also usable in the confirmation of a tissue wherein the above-mentioned gene can be expressed, or the confirmation of the existence of the gene or mRNA in various vital tissues by in situ hybridization.

This nucleic acid probe can be prepared by ligating the above-mentioned gene or its fragment to an appropriate vector, introducing it into a bacterium followed by replication, extracting with phenol, etc. from a disrupted cell solution, cleaving with restriction enzymes capable of recognizing the ligation site with the vector, electrophoresing and excising from the gel. Alternatively, this nucleic acid probe can be prepared by a chemical synthesis with the use of a DNA synthesizer or gene amplification techniques by PCR on the basis of each of the base sequences represented by SEQ ID NOs. 1, 3 and 12 in the Sequence Listing. To elevate the detection sensitivity in use, the nucleic acid probe may be labeled with a radioisotope or a fluorescent substance.

BRIEF DESCRIPTION OF THE FIGURES

FIG. 18 is a diagram showing a comparison among the amino acid sequences of proteins encoded by genes regulating aureobasidin sensitivity.

Figure 1:
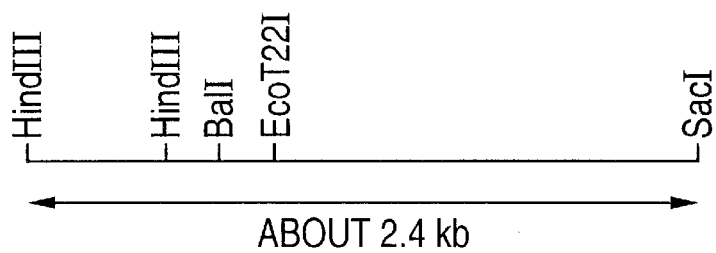
FIG. 1 is a restriction enzyme map of the genes spaur1$^R$ and spaur1$^S$ regulating aureobasidin sensitivity.

To further illustrate the present invention in greater detail, the following Examples will be given. However it is to be understood that the present invention is not restricted thereto.

EXAMPLES

Example 1

Cloning of a gene regulating aureobasidin sensitivity originating in fission yeast Schizo. pombe 1-a) Separation of aureobasidin-resistant mutant of Schizo. pombe About $1\times10^8$ cells of a Schizo. pombe haploid cell strain JY745 (mating type h⁻, genotype ade6-M210, leu1, ura4-D18) exhibiting a sensitivity to aureobasidin at a concentration of 0.08 μg/ml were suspended in 1 ml of a phosphate buffer containing 0.9% NaCl. Then the cells were mutagenized with EMS at a final concentration of 3% at 30° C. for 90 minutes. After neutralizing by adding 8 ml of 5% sodium thiosulfate, the cells thus treated were harvested by centrifugation (2500 r.p.m., 5 minutes), washed twice with 6 ml of physiological saline and then suspended in 2 ml of a YEL medium (3% of glucose, 0.5% of yeast extract). The suspension was incubated at 30° C. for 5 hours under stirring and then spreaded on a YEA plate (the YEL medium containing 1.5% of agar) containing 5 μg/ml of aureobasidin A. After incubating at 30° C. for 3 to 4 days, two or three aureobasidin-resistant colonies were formed per $1\times10^8$ cells. After carrying out the mutagenesis several times, five clone mutants, i.e., THR01, THR04, THR05, THR06 and THR07 were obtained. These mutants were resistant to more than 25 μg/ml of aureobasidin A but the same as the parent strain in the sensitivity to cycloheximide and amphotericin B. Therefore it is estimated that they are not mutants having a multiple drug resistance but ones having a resistance specific to aureobasidin.

1-b) Genetic analysis

Each of the above-mentioned resistant strains THR01, THR04, THR05, THR06 and THR07 was crossed with normal cells of Schizo. pombe LH121 strain (mating type h⁺, genotype ade6-M216, ura4-D18) differing in mating type. Diploid cells obtained were examined about the resistance to aureobasidin. Similar to the resistant strains, the five diploids formed by crossing the resistant strains with the normal one were resistant to 25 μg/ml of aureobasidin A, thus proving that these resistant mutations were dominant. To perform the tetrad analysis, the above-mentioned diploids were subsequently inoculated on an MEA medium (3% of malt extract, 2.5% of agar) for sporulation and incubated at 25° C. for 2 days. Prior to the meiosis, the diploid cells replicated DNA on the MEA medium and then underwent the meiosis to form asci each containing four ascospores of the haploid. These spores were separated with a micromanipulator and allowed to germinate on the YEA plate, followed by the formation of colonies. Then the resistance to aureobasidin of these colonies was examined. Among four spores contained in an ascus, the separation of the sensitivity versus the resistance showed 2:2. This result indicates that the aureobasidin resistant mutation was induced by a mutation in single gene. Further, the complementation test was performed in order to confirm whether the resistant genes of the above-mentioned five mutants were identical with each other or not. For example, a mutant of the mating type h⁺, which had been obtained by crossing the mutant THR01 with the LH121 strain in the above tetrad analysis, was crossed with another variant THR04 (mating type h⁻) on the MEA plate as described above and, after sporulation, the tetrad analysis was carried out. As a result, all of the colonies formed from four ascospores showed resistance to aureobasidin, which indicates that the mutational genes of THR01 and THR04 are the same with each other. Similarly, the five mutants were examined and it was thus found out that all mutations occurred on the same gene. This gene regulating aureobasidin sensitivity is named spaur1, the normal gene (sensitive gene) is named spaur1$^S$ and the mutational gene (resistant gene) is named spaur1$^R$.

1-c) Preparation of genomic library of aureobasidin resistant strain

Genomic DNA was extracted and purified from the aureobasidin resistant strain THR01 by the method of P. Philippsen et al. [Methods in Enzymology, 194, 169–175 (1991)]. The purified genomic DNA (8 μg) was partially digested by treating with 5 U of a restriction enzyme HindIII at 37° C. for 10 minutes, deproteinized with phenol/chloroform and precipitated with ethanol. The partially digested DNA was electrophoresed on a 0.8% agarose gel and DNA in the region of 3 to 15 kb was extracted. The DNA thus obtained was ligated with a yeast-E. coli shuttle vector pAU-PS (2 μg) which had been completely digested with HindIII by using a DNA ligation kit (manufactured by Takara Shuzo Co., Ltd.) and then transformed into E. coli HB101. Thus a genomic library of the aureobasidin resistant strain was formed. E. coli containing this genomic library was incubated in 50 ml of an LB medium (1% of bacto trypton, 0.5% of bacto yeast extract, 0.5% of sodium chloride) containing 100 μg/ml of ampicillin and 25 μg/ml of tetracycline at 37° C. overnight. Then a plasmid was recovered and purified from the E. coli cells.

1-d) Expression and cloning of aureobasidin resistant gene spaur1$^R$

The plasmid originating in the genomic library of the aureobasidin resistant strain as prepared above was transformed into a strain Schizo. pombe JY745 by the method of Okazaki et al. [Nucleic Acid Research, 18, 6485–6489 (1990)]. The transformed cells were spreaded on a minimum medium SD plate [0.67% of yeast nitrogen base without amino acids (manufactured by Difco), 2% of glucose, 2% of agar] containing 75 μg/ml of adenine sulfate and 50 μg/ml of leucine. After incubating at 30° C. for 3 to 4 days, the colonies thus formed were replicated onto an SD plate containing 5 μg/ml of aureobasidin A, 75 μg/ml of adenine sulfate and 50 g/ml of leucine. It is conceivable that a colony propagated on this plate may have the plasmid containing the aureobasidin resistant gene. This colony was inoculated into 5 ml of a liquid SD medium containing 75 μg/ml of adenine sulfate and 50 μg/ml of leucine. After incubating at 30° C. for 2 days, the plasmid was recovered from the propagated cells by the method of I. Hagan et al. [J. Cell Sci., 91, 587–595 (1988)]. Namely, the cells were harvested from the culture (5 ml) by centrifugation and then suspended in 1.5 ml of 50 mM citrate/phosphate buffer containing 1.2 M of sorbitol and 2 mg/ml of Zymolyase. Then the suspension was maintained at 37° C. for 60 minutes. The cells were collected by centrifuging at 3,000 r.p.m. for 30 seconds and suspended in 300 μl of a TE [10 mM of Tris-HCl, pH 8, 1 mM of EDTA] solution. After adding 35 μl of 10% SDS, the mixture was maintained at 65° C. for 5 minutes. After adding 100 μl of 5 M potassium acetate, the mixture was allowed to stand in ice for 30 minutes. Then it was centrifuged at 10,000 r.p.m. at 4° C. for 10 minutes and a plasmid DNA was purified from the supernatant by using EASYTRAP™ (manufactured by Takara Shuzo Co., Ltd.).

Figure 12:
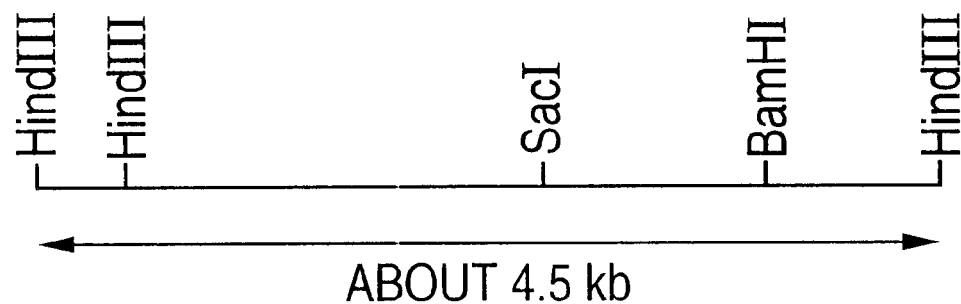
FIG. 12 is a restriction enzyme map of pAR25.
Figure 13:
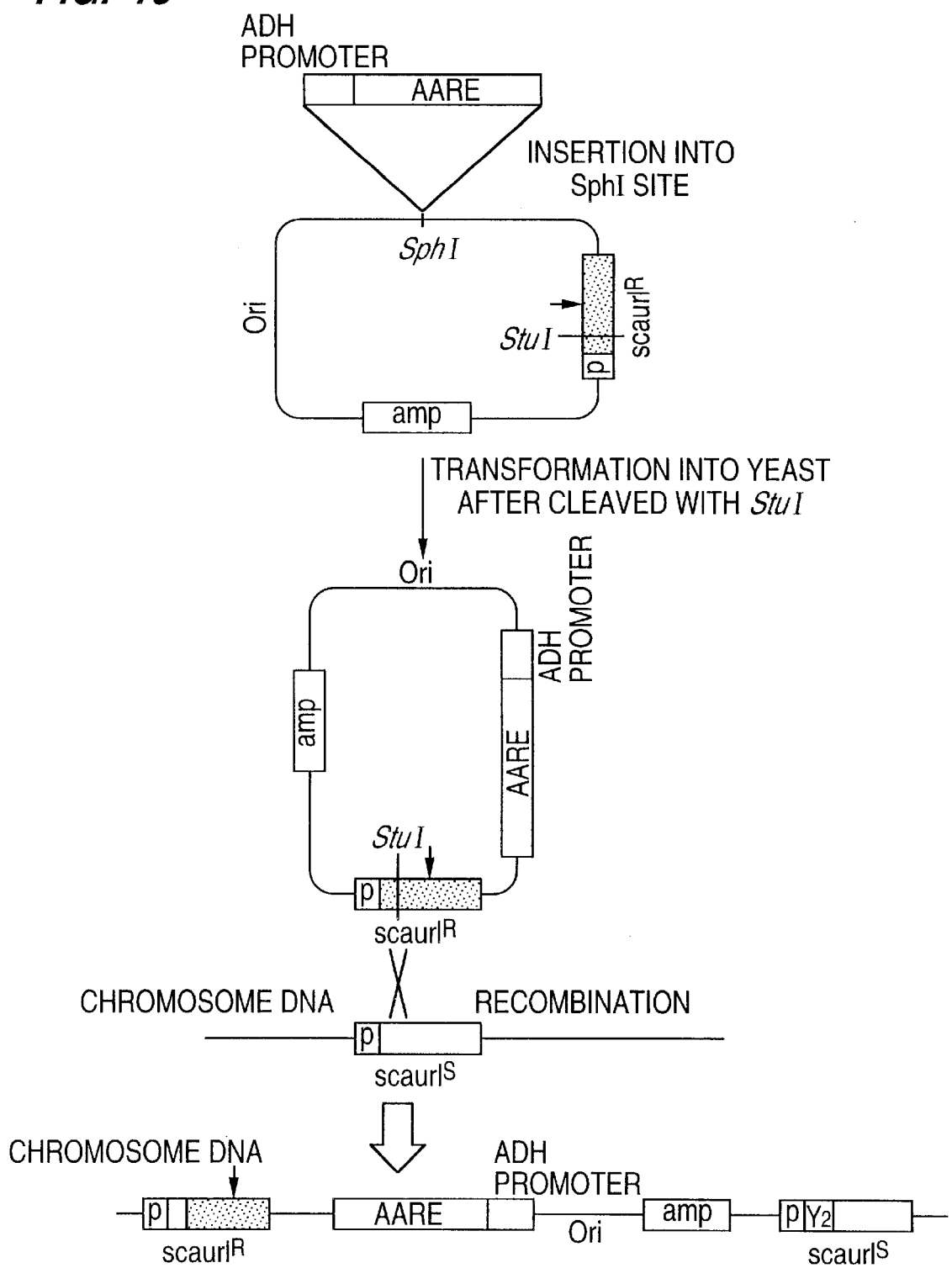
FIG. 13 shows a construction of the vector which is a example of the present invention, and integration of the vector into the chromosome.

This plasmid was transformed into E. coli HB101 and a plasmid DNA was prepared from E. coli colonies formed on an LB medium containing ampicillin and tetracycline. This plasmid, which contained a DNA of 4.5 kb, was named pAR25. FIG. 12 shows the restriction enzyme map of the DNA of 4.5 kb in pAR25. To specify the gene region, HindIII fragments or SacI fragments of various sizes were subcloned into the pAU-PS vector. These DNAs were transformed into normal JY745 cells by the above-mentioned method of Okazaki et al. and the acquisition of aureobasidin resistance was examined. As a result, it is revealed that a HindIII-SacI 2.4 kb DNA fragment contains the spaur1$^R$ gene. The restriction enzyme map of this DNA segment containing the aureobasidin resistant gene spaur1$^R$ is shown in FIG. 1. This fragment was cloned into a pUC118 vector (named pUARS2$^R$) and then the DNA nucleotide sequence was identified (SEQ ID No. 1 in Sequence Listing). From this nucleotide sequence, it is revealed that the spaur1$^R$ gene code for a protein having an amino acid sequence represented by SEQ ID No. 16 in Sequence Listing.

1-e) Cloning of aureobasidin sensitive gene spaur1$^S$

By the same method as the one employed in the above c), genomic DNA was extracted and purified from normal cells. After partially digesting with HindIII, a genomic library of the normal cells was constructed. An E. coli stock containing this library DNA was spreaded on an LB agar medium containing ampicillin and tetracycline and incubated overnight at 37° C. The colonies thus formed were transferred onto a nylon membrane (Hybond™-N, manufactured by Amersham) and the colony hybridization was performed.

As a probe, the above-mentioned DNA fragment (2.4 kb) obtained by cleaving the spaur1$^R$ gene with HindIII-SacI and labeled with [α-$^{23}$P] dCTP by using a random primer DNA labeling kit (manufactured by Takara Shuzo Co., Ltd.) was used. As the results of screening of 5×10$^4$ colonies, five clones being hybridizable with the probe were obtained. Plasmids were purified from E. coli cells of these five clones. As the result of the cleavage with restriction enzymes, it was found out that all of these clones contained the same DNA fragment of 4.5 kb (named pARN1). The restriction enzyme map of the DNA of 4.5 kb in pARN1 was identical with that of pAR25 shown in FIG. 10. Therefore, a HindIII-SacI 2.4 kb DNA fragment which was a region containing the spaur1$^S$ gene was prepared from PARN1. Then it was cloned into the pAU-PS vector and this plasmid was named pSPAR1.

By using this plasmid pSPAR1, a strain E. coli JM109 was transformed and the transformant thus obtained was named and designated as Escherichia coli JM109/pSPAR1. It has been deposited at National Institute of Bioscience and Human-Technology, Agency of Industrial Science and Technology in accordance with the Budapest Treaty under the accession number FERM BP-4485. This DNA fragment containing the aureobasidin sensitive gene spaur1$^S$ had the restriction enzyme map shown in FIG. 1 and the DNA nucleotide sequence thereof was the one represented by SEQ ID No. 17 in Sequence Listing. Based on this nucleotide sequence, it has been revealed that the spaur1$^S$ gene codes for a protein having the amino acid sequence represented by SEQ ID No. 28 in Sequence Listing and, when compared with the resistant gene spaur1$^R$, the amino acid at the residue 240 has been changed from glycine into cysteine.

Example 2

Cloning of aureobasidin sensitive genes scaur1 and scaur2 originating in budding yeast S. cerevisiae 2-a) Separation of aureobasidin resistant mutant of S. cerevisiae A strain S. cerevisiae DKD5D (mating type a, genotype leu2-3 112, trp1, his3) having a sensitivity to aureobasidin at a concentration of 0.31 μg/ml was mutagenized with EMS in the same manner as the one employed in the case of Schizo. pombe. Then resistant mutants were separated on an agar plate of a complete nutritional medium YPD (1% of yeast extract, 2% of polypeptone, 2% of glucose) containing 5 μg/ml or 1.5 μg/ml of aureobasidin A. After repeating the mutagenesis several times, 34 mutant clones were obtained. These mutants were resistant to more than 25 μg/ml of aureobasidin A and estimated as having not a multiple drug resistance mutation but a aureobasidin-specific resistance mutation.

2-b) Genetic analysis

Similar to the above-mentioned case of Schizo. pombe, the genetic analysis using the tetrad analysis and the complementation test was performed. As a result, the genes could be classified into two types. These genes regulating aureobasidin sensitivity were named scaur1 and scaur2, the resistant genes isolated from the resistant mutant were named scaur1$^R$ and scaur2R, and the sensitive genes isolated from the sensitive wild-type strain were named scaur1$^S$ and scaur2$^S$, respectively.

The R94A strain had a gene with dominant mutation (scaur1$^R$). It has been further clarified that the scaur1 gene is located in the neighborhood of the met14 gene of the eleventh chromosome.

2-c) Preparation of genomic library of aureobasidin resistant strain having aureobasidin resistant gene scaur1$^R$ Genomic DNA was extracted and purified from the aureobasidin resistant strain R94A by the above-mentioned method of P. Philippsen et al. The purified genomic DNA (8 μg) was partially digested by treating with 5 U of a restriction enzyme HindIII at 37° C. for 10 minutes, deproteinized with phenol/chloroform and precipitated with ethanol. The partially digested DNA thus obtained was electrophoresed on a 0.8% agarose gel and DNA in the region of 3 to 15 kb was extracted. The DNA thus obtained was ligated with a yeast-E. coli shuttle vector pWH5 (2 μg) which had been completely digested with HindIII by using a DNA ligation kit and then transformed into E. coli HB101. Thus a genomic library was formed. E. coli containing this genomic library was cultured in 50 ml of an LB medium containing ampicillin and tetracycline at 37° C. overnight. Then a plasmid was recovered and purified from the E. coli cells.

2-d) Expression and cloning of aureobasidin resistant gene scaur1$^R$

Figure 2:
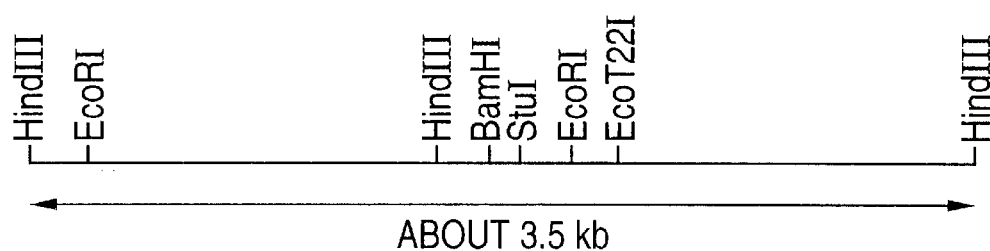
FIG. 2 is a restriction enzyme map of scaur1$^R$ and scaur1$^S$.

The above-mentioned genomic library of the R94A strain was transformed into S. cerevisiae SH3328 (mating type α, genotype ura3-52, his4, thr4, leu2-3•112) in accordance with the method of R. H. Schiestl et al. [Current Genetics, 16, 339–346 (1989)]. The transformed cells were spread on a minimum medium SD plate [0.67% of yeast nitrogen base without amino acids, 2% of glucose, 2% of agar] containing 25 μg/ml of uracil, 35 μg/ml of histidine and 500 μg/ml of threonine. After incubating at 30° C. for 3 to 4 days, the colonies thus formed were replicated onto a YPD agar plate containing 1.5 μg/ml of aureobasidin A. A colony thus formed was inoculated into 5 ml of a liquid YPD medium. After incubating at 30° C. for 2 days, a plasmid DNA was recovered from the propagated cells by the above-mentioned method of 1. Hagan et al. This plasmid was transformed into a yeast again and it was confirmed that the obtained transformant had acquired aureobasidin resistance. This plasmid, which contained a DNA of 3.5 kb, was named pWTCR3. Neither the DNA fragment of 2.0 kb nor the DNA fragment of 1.5 kb obtained by cleaving with HindIII exhibited any aureobasidin resistant activity alone. Thus it is confirmed that the gene is contained in the DNA fragment of 3.5 kb. FIG. 2 shows the restriction enzyme map of this DNA fragment of 3.5 kb containing the aureobasidin resistant gene scaur1$^R$. The HindIII fragments of 1.5 kb and 2 kb were each cloned into pUC118, followed by the determination of the DNA nucleotide sequence (SEQ ID No. 19 in Sequence Listing). From this nucleotide sequence, it has been revealed that the scaur1$^R$ gene codes for a protein having an amino acid sequence represented by SEQ ID No. 20 in Sequence Listing.

2-e) Cloning of aureobasidin sensitive gene scaur1$^S$ corresponding to aureobasidin resistant gene scaur1$^R$ By the same method as the one employed in the above Example 2-c), genomic DNA was extracted and purified from the parent strain S. cerevisiae DKD5D. After partially digesting with HindIII, the DNA was ligated with pWH5 and transformed into E. coli HB101. Thus a genomic library of the normal cells was formed. An E. coli stock containing this library DNA was spreaded on an LB agar medium containing ampicillin and tetracycline and incubated overnight at 37° C. The colonies thus formed were transferred onto a nylon membrane (Hybond™-N) and the colony hybridization was carried out. As a probe, the DNA fragment of 3.5 kb obtained in the above Example 2-d) and labeled with [α-$^{32}$P] dCTP by using a random primer DNA labeling kit (manufactured by Takara Shuzo Co., Ltd.) was used. As the results of screening of 2×10$^4$ colonies, seven clones being hybridizable with the probe were obtained. Plasmids were purified from E. coli cells of these clones. As the result of the cleavage with restriction enzymes, one of these clones contained a DNA fragment of 3.5 kb. This DNA fragment had the restriction enzyme map of FIG. 2 and thus judged as containing the scaur1$^S$ gene. The plasmid containing this DNA fragment was named pSCAR1, while E. coli HB101 having this plasmid introduced therein was named and designated as Escherichia coli HB101/pSCAR1. This strain has been deposited at National Institute of Bioscience and Human-Technology, Agency of Industrial Science and Technology in accordance with the Budapest Treaty under the accession number FERM BP-4483. The DNA fragment of 3.5 kb obtained by partially digesting pSCAR1 with HindIII was subcloned into pUC118 and the nucleotide sequence thereof was determined (SEQ ID No. 21 in Sequence Listing). A comparison with the resistant gene indicates that the base at the position 852 has been changed from T into A and, due to this replacement, the amino acid has been converted from phenylalanine into tyrosine (SEQ ID No. 22 in Sequence Listing).

2-f) Preparation of genomic library of aureobasidin resistant strain having aureobasidin resistant gene scaur2R A genomic library was prepared from an aureobasidin resistant strain L22-8B by the same method as the one described in Example 2-c). E. coli containing this genomic library was cultured in an LB medium (50 ml) containing ampicillin and tetracycline at 37° C. overnight. Then plasmids were recovered and purified from the E. coli cells.

2-g) Expression and cloning of aureobasidin resistant gene scaur2$^R$

Figure 3:
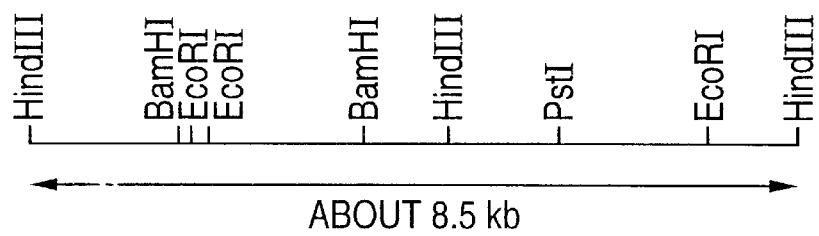
FIG. 3 is a restriction enzyme map of scaur2$^R$ and scaur2$^S$.

The above-mentioned plasmids originating in the genomic library of the L22-8B strain were transformed into S. cerevisiae SH3328 by the above-mentioned method of R. H. Schiestl. From the transformed strains, an aureobasidin resistant strain was isolated. Then a plasmid DNA containing the scaur2$^R$ gene was recovered from this transformant by the above-mentioned method of I. Hagan et al. This plasmid was transformed into a yeast again and it was confirmed that the transformant had acquired aureobasidin resistance. This plasmid, which contained a DNA of 8.5 kb, was named pSCAR2. FIG. 3 shows the restriction enzyme map of the DNA fragment of 8.5 kb containing this aureobasidin resistant gene scaur2$^R$. E. coli HB101 having this plasmid pSCAR2 introduced therein was named and designated as Escherichia coli HB101/pSCAR2. This strain has been deposited at National Institute of Bioscience and Human-Technology, Agency of Industrial Science and Technology in accordance with the Budapest Treaty under the accession number FERM BP-4484. By using BamHI, EcoRI, HindIII and PstI, DNA fragments of various sizes were prepared and cloned into the pWHS vector. These plasmids were transformed into S. cerevisiae DKD5D in accordance with the above-mentioned method of R. H. Schiestl et al. Then it was examined whether these transformants had acquired aureobasidin resistance or not. As a result, none of the transformants of the DNA fragments was a resistant one. Thus it has been clarified that the DNA fragment of the full length is necessary for the expression of the aureobasidin resistance.

2-h) Isolation of aureobasidin sensitive gene scaur2$^S$ corresponding to aureobasidin resistant gene scaur2$^R$ An E. coli stock containing the genomic library of Example 2-e) prepared from normal cells of S. cerevisiae DKD5D was spreaded on an LB agar medium containing ampicillin and tetracycline and incubated at 37° C. overnight. The colonies thus formed were transferred onto a nylon membrane (Hybond™-N) and the colony hybridization was performed. As a probe the DNA fragment of 8.5 kb obtained in the above Example 2-g) and labeled with [α-$^{32}$P] dCTP by using a random primer DNA labeling kit was used. As the results of screening of 2×10$^4$ colonies, several clones being hybridizable with the probe were obtained. Some of these clones contained a DNA fragment of 4.6 kb while others contained a DNA fragment of 3.9 kb. From the restriction enzyme maps of these DNA fragments, it was found out that these DNA fragments were each a part of the scaur2$^S$ gene shown in FIG. 3. These DNA fragments were ligated together to thereby give a scaur2$^S$ fragments shown in FIG. 3. The DNA fragment of 8.5 kb thus obtained was subcloned into pUC 118 and then the DNA nucleotide sequence was determined (SEQ ID No. 23 in Sequence Listing). Based on the nucleotide sequence of SEQ ID No. 23 in Sequence Listing, the amino acid sequence represented by SEQ ID No. 24 in Sequence Listing was estimated.

Example 3

Figure 4:
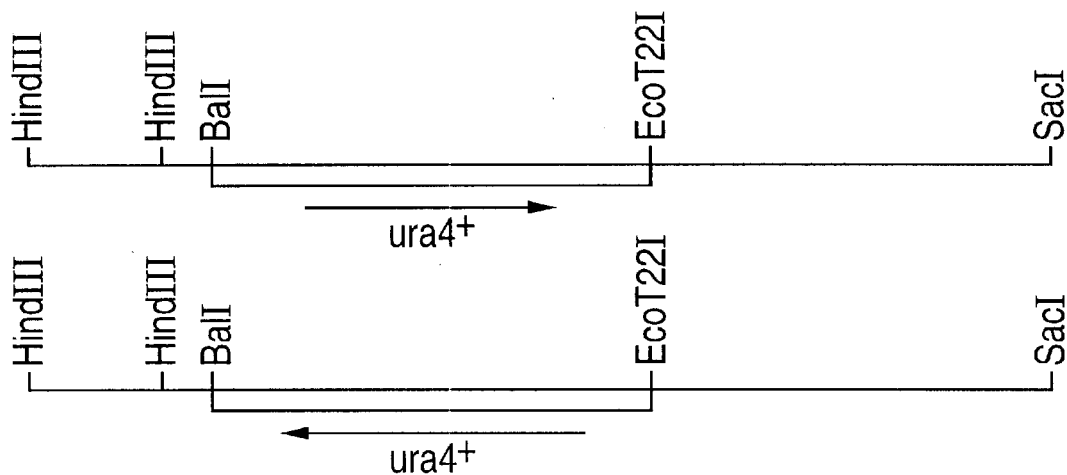
FIG. 4 shows the structure of a DNA for disrupting the *Schizo. pombe* spaur1$^S$ gene.

Gene disruption test on spaur1$^S$ and scaur1$^S$ genes 3-a) Gene disruption test on spaur1$^S$ gene In order to examine whether the aureobasidin sensitive gene spaur1$^S$ is necessary in the cell growth by the gene disruption test, the plasmid pUARS2R prepared in Example 1-d) was first cleaved with BalI and EcoT22I. After eliminating a DNA fragment of 240 bp, the residual DNA fragment was blunted by using a DNA blunting kit (manufactured by Takara Shuzo Co., Ltd.). Then this DNA was ligated with a DNA containing ura4$^+$ gene of 1.7 kb, which had been obtained by excising from a pUC8ura4 plasmid [Mol. Gen. Genet., 215, 81–86 (1988)] by cleaving with HindIII and blunting, to thereby give a plasmid pUARS2RBT22::ura4-1 and another plasmid pUARS2RBT22::ura4-6 in which the ura4 DNA had been inserted in the opposite direction. Both of these disrupted genes were excised from the vector pUC118 by cleaving with SacI and HindIII and ARS2RBT22::ura4-1 and ARS2RBT22::ura4-6 (FIG. 4), which were spaur1$^S$ DNA fragments containing ura4$^+$, were purified. The purified DNA fragments were transformed into diploid cells Schizo. pombe C525 (h$^{90}$/h$^{90}$, ura4-D18/ura4-D18, leu1/leu1, ade6-M210/ade6-M216) by the above-mentioned method of Okazaki et al. and then a transformant was screened on an SD agar plate containing leucine. In the transformant thus obtained, one of a pair of spaur1$^S$ genes on the chromosome had been is replaced by the disrupted gene ARS2RBT22::ura4-1 or ARS2RBT22::ura4-6 introduced thereinto. These cells were allowed to undergo sporulation on a sporulation medium MEA and subjected to the tetrad analysis. As a result, it was found out that two of the four ascospores formed colonies but the residual two spores formed no colony. That is to say, the spores suffering from the replacement of the normal spaur1$^S$ gene by the disrupted gene ARS2RBT22::ura4-1 were not propagated. It has been thus revealed that the spaur1$^S$ gene is essentially required for the growth of the cells.

3-b) Gene disruption test on scaur1$^S$ gene

Figure 5:
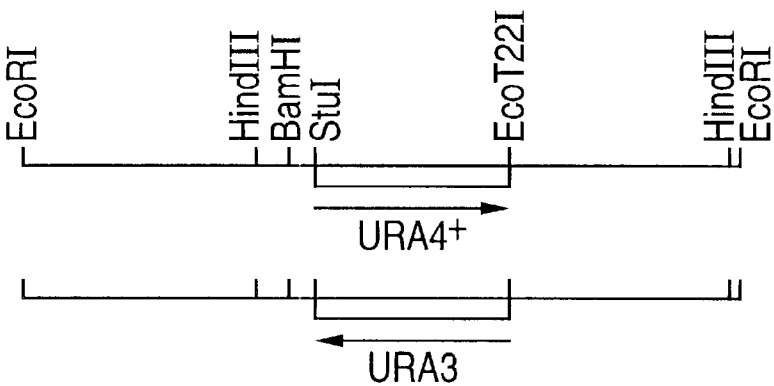
FIG. 5 shows the structure of a DNA for disrupting the *S. cerevisiae* scaur1$^S$ gene.

The plasmid pSCAR1 prepared in Example 2-e) was partially digested with HindIII to thereby give a DNA fragment of 3.5 kb shown in FIG. 2. This DNA fragment was cloned into the HindIII site of pUC119 and the obtained product was named pSCAR3. The obtained pSCAR3 was cleaved with StuI and EcoT22I. After eliminating a DNA fragment of 0.3 kb, the obtained DNA was ligated with a DNA fragment (1.1 kb) of URA3 gene which had been obtained by cleaving a plasmid pYEUra3 (manufactured by Clontech Laboratories, Inc.) with HindIII and EcoRI and blunting. Thus, a plasmid pUSCAR3.ST22::URA3$^+$ and another plasmid pUSCAR3.ST22::URA3A, in which the URA3 gene had been inserted in the opposite direction, were obtained. These disrupted genes were excised in the EcoRI site in the scaur1$^S$ gene and the EcoRI site in the pUC119 vector by cleaving with EcoRI. The scaur1$^S$ DNA fragments containing URA3, SCAR3.ST22::URA3+ and SCAR3.ST22::URA3A (FIG. 5), were purified. The purified DNA fragments were transformed into diploid cells of *S. cerevisiae* AOD1 (mating type a/α, genotype ura3-52/ura3-52, leu2-3 112/leu2-3 112, trp1/TRP1, thr4/THR4, his4/HIS4) by the above-mentioned method of R. H. Schiestl and transformants were screened on an SD agar plate containing leucine. The transformants thus obtained were allowed to undergo sporulation on a sporulation medium SP (1% of potassium acetate, 2% of agar) and subjected to the tetrad analysis. As a result, it was found out that two of the four ascospores underwent germination and formed colonies but the residual two spores did not undergo colony formation. That is to say, the spores suffering from the replacement of the scaur1$^S$ gene by the disrupted gene were not propagated. It has been thus revealed that the scaur1$^S$ gene is essentially required for the growth of the cells.

Example 4

Figure 10:
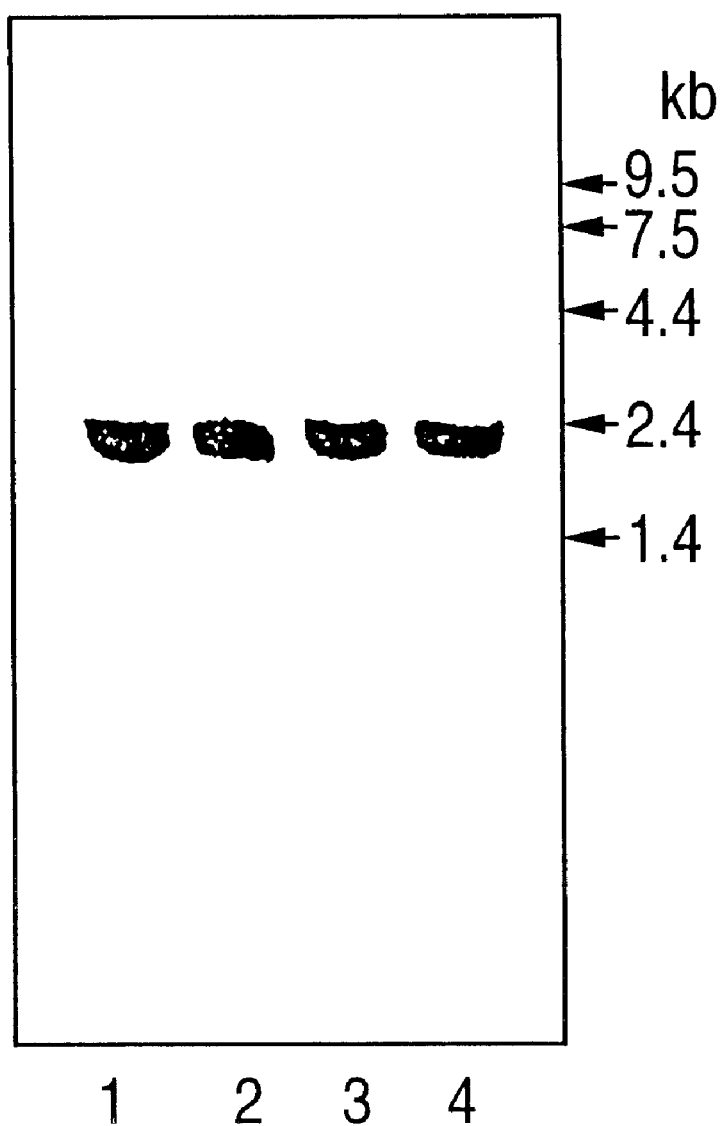
FIG. 10 shows the results of the northern hybridization of the spaur1 gene of *Schizo. pombe*.

Examination on the expression of aureobasidin sensitive gene spaur1 by northern hybridization From a normal strain or a resistant strain of *Schizo. pombe*, the whole RNAs were extracted and purified by the method of R. Jensen et al. [*Proc. Natl. Acad. Sci. USA*, 80, 3035–3039 (1983)]. Further, poly(A)$^+$RNA was purified by using Oligotex™-dT30 (manufactured by Takara Shuzo Co., Ltd.). The purified poly(A)$^+$RNA (2.5 µg) was separated by the electrophoresis on a 1.2% agarose gel containing formaldehyde and transferred onto a nylon membrane (Hybond™-N). After immobilizing, the hybridization was performed with the use of a HindIII-SacI fragment (2 kb) of the spaur1$^R$ gene labeled with [α-$^{32}$P]dCTP as a probe. As a result, both of the normal cells and the resistant cells showed a band of the same amount of about 2 kb. In both cases, this amount underwent no change in the logarithmic growth phase and the stationary phase (FIG. 10). FIG. 10 is an autoradiogram showing the results of the northern hybridization wherein mRNAs obtained from cells of a sensitive strain of *Schizo. pombe* in the logarithmic growth phase (lane 1), cells of a resistant strain in the logarithmic growth phase (lane 2), cells of the sensitive strain in the stationary phase (lane 3) and cells of the resistant strain in the stationary phase (lane 4) are electrophoresed on a 1.2% agarose gel containing formaldehyde.

Example 5

Determination of the activity of scaur1$^S$ gene 5-a) Construction of plasmid YEpSCARW3 (FIG. 9) and YEpSCARW1

Figure 9:
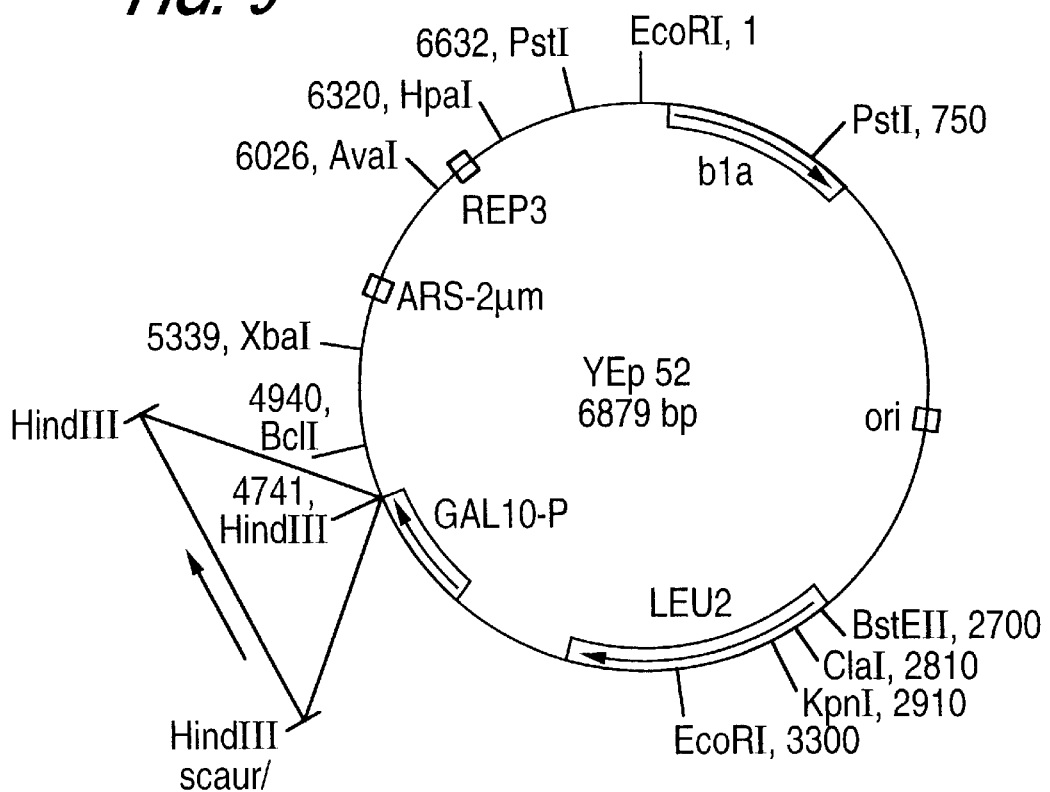
FIG. 9 shows the structure of a plasmid YEpSCARW3 for expressing the scaur1 gene.

The plasmid pSCAR1 prepared in Example 2-e) was cleaved with HindIII and a fragment of 2 kb containing the whole ORF was excised. This fragment was inserted into the HindIII site of a expression-plasmid YEp52 having a promoter Gal10, the expression of which was induced by galactose in a medium. The plasmid having the scaur1$^S$ gene which had been inserted in such a direction as to be normally transcribed by the promoter Gal10 was named YEpSCARW3. FIG. 9 shows the structure of this plasmid. Further, the plasmid having the scaur1$^S$ gene inserted in the opposite direction was named YEpSCARW1.

5-b) Transformation by plasmids YEpSCARW3 and YEpSCARW1

By using 5 µg portions of the plasmids YEpSCARW3 and YEpSCARW1, the diploid *S. cerevisiae* cells with the disrupted scaur1$^S$ gene prepared in Example 3-b) were transformed. Then transformants were screened on an SD agar plate. These transformants were allowed to undergo sporulation on an SP medium and then subjected to the tetrad analysis. When the expression of the scaur1$^S$ gene was induced by using a YPGal medium (1% of yeast extract, 2% of polypeptone, 2% of galactose), the ascospores formed from the diploid cells transformed by YEpSCARW3 all underwent germination while two of the four ascospores formed from the diploid cells transformed by YEpSCARW1 underwent germination but not the remaining two. It is thus conceivable that the cells with the disrupted scaur1$^S$ gene have reverted to the normal state by introducing YEpSCARW3 containing the scaur1$^S$ gene into these cells. Accordingly, the use of these cells with the disrupted scaur1$^S$ gene as a host makes it possible to determine the activity of normal aur1-analogous genes carried by other organisms.

Example 6

Confirmation and cloning of aur1 and aur2 genes (caaur1, caaur2) carried by *C. albicans*

6-a) Detection of aur1 gene by the PCR method

Poly(A)$^+$RNA was extracted and purified from an aureobasidin sensitive strain *C. albicans* TIMM0136 by the same method as the one employed in Example 4. By using the poly(A)$^+$RNA (5 µg) as a template, a double-stranded cDNA was synthesized on a cDNA synthesizing system Plus (manufactured by Amersham) with the use of an oligo(dT) primer. Mixed primers for PCR corresponding to amino acid sequence regions being common to the amino acid sequences of *S. cerevisiae* and *Schizo. pombe* were synthesized on a DNA synthesizer and purified. That is to say, a primer of SEQ ID No. 25 in Sequence Listing corresponding to the region of amino acids at the 184- to 192-positions of SEQ ID No. 18 in Sequence Listing of *Schizo. pombe* (from the 184- to 192-positions of SEQ ID No. 22 in Sequence Listing of *S. cerevisiae*) and another primer of SEQ ID No. 26 in Sequence Listing corresponding to the region of amino acids from the 289- to 298-positions of *Schizo. pombe* (from the 289- to 298-positions of SEQ ID No. 22 in Sequence Listing of *S. cerevisiae*) were employed.

Figure 6:
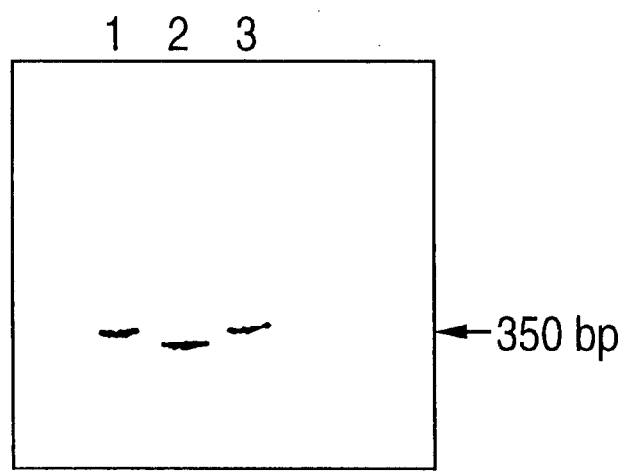
FIG. 6 shows the results of the detection of the aur1 gene caaur1 carried by *C. albicans* by the PCR method.

PCR was performed by using these primers and the above-mentioned cDNA as a template by repeating a cycle comprising treatment at 94° C. for 30 seconds, one at 48° C. for 1 minute and one at 72° C. for 2 minutes 25 times. As a result, a DNA (about 350 bp) being almost the same as *S.* cerevisiae and Schizo. pombe in length was amplified (FIG. 6). FIG. 6 shows a pattern obtained by carrying out PCR with the use of cDNA of C. albicans (lane 1), cDNA of S. cerevisiae (lane 2) and cDNA of Schizo. pombe (lane 3) as a template, electrophoresing each PCR product on an agarose gel and staining with ethidium bromide.

Figure 7:
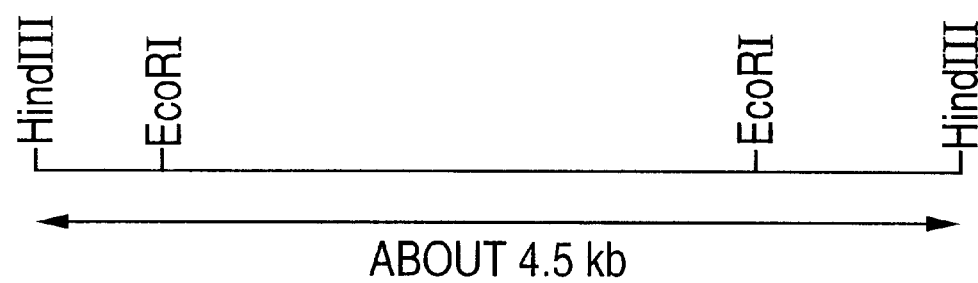
FIG. 7 is a restriction enzyme map of the caaur1 gene carried by *C. albicans*.

6-b) Cloning of aur1 gene (caaur1) of C. albicans (i) Genomic DNA was extracted and purified from a strain C. albicans TIMM0136 by the same method as the one described in Example 1-c). After partially digesting with HindIII, the DNA fragment was ligated with a Traplex119 vector which had been completely digested with HindIII and transformed into E. coli HB101. Thus a genomic library of C. albicans was prepared. From this library, a DNA fragment of 4.5 kb containing the aur1 gene of C. albicans was cloned by using the DNA fragment of C. albicans obtained by the PCR described in Example 6-a), which had been labeled with [α-$^{32}$P]dCTP by using a random primer DNA labeling kit (manufactured by Takara Shuzo Co., Ltd.), as a probe. This DNA fragment had a restriction enzyme map shown in FIG. 7 and the DNA nucleotide sequence thereof is represented by SEQ ID No. 27 in Sequence Listing. Based on this nucleotide sequence, it was estimated that the caaur1 gene coded for a protein having the amino acid sequence represented by SEQ ID No. 28 in Sequence Listing. When compared with the scaur1$^S$ protein, a homology of as high as 53% was observed. A Traplex119 vector having this caaur1 gene integrated therein was named pCAAR1, while E. coli HB101 transformed by this plasmid was named and designated as Escherichia coli HB101/pCAAR1. This strain has been deposited at National Institute of Bioscience and Human-Technology, Agency of Industrial Science and Technology in accordance with the Budapest Treaty under the accession number FERM BP-4482.

Next, pCAAR1 was treated with HindIII to thereby give caaur1 of 4.5 kb. Further, it was integrated into pTV118 which had been completely digested with HindIII to thereby prepare a plasmid for expressing caaur1. This plasmid was named pTCAAR1.

(ii) Genomic DNA was extracted and parified from a strain C. albicans TIMM1768 [The Journal of Antibiotics, 46, 1414–1420(1993)] by the same method as the one described in Example 1-c). After partially digesting with HindIII, the DNA fragment was ligated with a pUC118 vector which had been completely digested with HindIII and transformed into E. coli HB101. Thus a genomic library of C. albicans TIMM1768 was prepared. From this library, a DNA fragment of 4.5 kb containing the aur1 gene of C. albicans TIMM1768 was cloned by the colony hybridization with the same probe as that described in Example 6-b)-(i). This DNA fragment had the same restriction enzyme map as that shown in FIG. 7. Next, a part of the DNA sequence containing a ORF in this DNA fragment was determined. The DNA nucleotide sequence thereof is represented by SEQ ID No. 35 in Sequence Listing. Based on this nucleotide sequence, it was estimated that this gene coded for a protein having the amino acid sequence represented by SEQ ID No. 36 in Sequence Listing. When the amino acid sequence of the caaur1 protein C. albicans TIMM1768 was compared with that of the caaur1 protein of C. albicans TIMM0136, the amino acid sequences of the 1- to 381-positions and the 383- to 423-positions and the 425- to 471-positions of caaur1 protein (SEQ ID No. 28 in Sequence Listing) in C. albicans TIMM0136 were identical with the amino acid sequences of the 2- to 382-positions and the 384- to 424-positions and the 426- to 472-positions, respectively, of caaur1 protein (SEQ ID No. 36 in Sequence Listing) in C. albicans TIMM1768.

However, serines at the 382- and 424-positions of SEQ ID No. 28 in Sequence Listing were replaced with prolines at the 383- and 425-positions of SEQ ID No. 36 in Sequence Listing.

6-c) Cloning of aur2 gene (caaur2) of C. albicans

Figure 8:
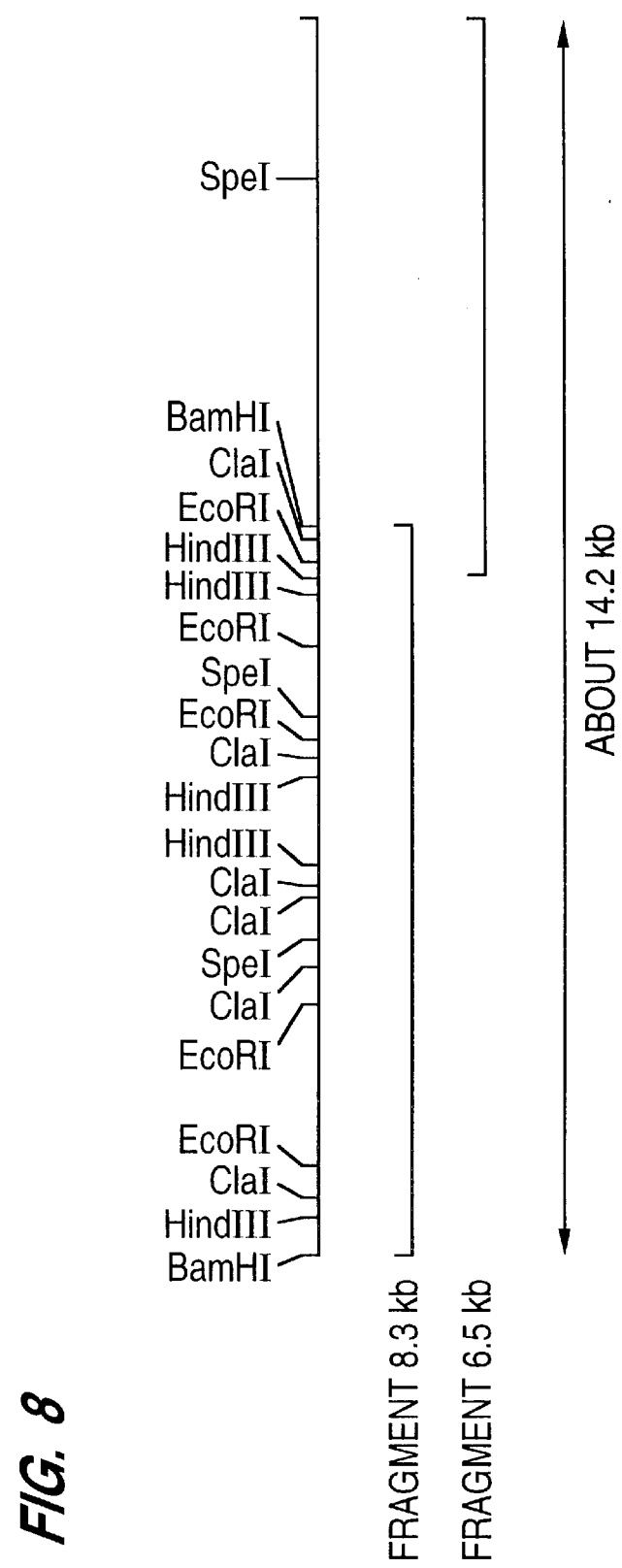
FIG. 8 is a restriction enzyme map of the caaur2 gene.

Genomic DNA of a strain C. albicans TIMM0136 was digested with BamHI and ligated with a pTV118 vector which had been completely digested with BamHI. Then it was transformed into E. coli HB101 to thereby prepare a genomic library of C. albicans. On the other hand, the DNA fragment containing the scaur2$^S$ gene obtained in Example 2-h) was cleaved with HindIII and PstI to thereby give a DNA fragment of 1.2 kb. This DNA fragment was labeled with [α-$^{32}$P]dCTP by using a random primer DNA labeling kit. By using this labeled DNA fragment as a probe, the above-mentioned C. albicans genomic library was screened by the colony hybridization. Thus a plasmid containing a DNA fragment of 8.3 kb was obtained. A part of the DNA sequence upstream of the BamHI site of this DNA fragment was determined (SEQ ID No. 29 in Sequence Listing). Based on this sequence, an amino acid sequence represented by SEQ ID No. 30 in Sequence Listing was estimated. It corresponded to the amino acid sequence of the 1230- to 1309-positions of the amino acid sequence of the scaur2 gene (SEQ ID No. 24), having a homology of as high as 77%. Since this DNA fragment lacked a part of the C-end, the genomic library prepared in Example 6-b) was further screened by using this DNA fragment as a probe. Thus a DNA fragment of 6.5 kb having the C-terminal part was obtained. FIG. 8 shows the restriction enzyme map of the DNA region containing the caaur2 gene thus clarified.

A pTV118 vector having the above-mentioned caaur2 gene of 8.3 kb integrated therein was named pCAAR2N, while E. coli HB101 transformed by this plasmid was named and designated as Escherichia coli HB101/pCAAR2N. This strain has been deposited at National Institute of Bioscience and Human-Technology, Agency of Industrial Science and Technology in accordance with the Budapest Treaty under the accession number FERM BP4481.

Example 7

Preparation of antibody against protein coded for by scaur1$^S$ gene and staining of S. cerevisiae cells and detection of said protein by using this antibody 7-a) Preparation of antibody SCAR1-1 (SEQ ID No. 33 in Sequence Listing) comprising a peptide corresponding to the amino acids at the residue 103 to 113 in the amino acid sequence of SEQ ID No. 22 in Sequence Listing having cysteine added to the N-end thereof and SCAR1-2 (SEQ ID No. 34 in Sequence Listing) comprising a peptide corresponding to the amino acids at the residue 331 to 348 in the amino acid sequence of SEQ ID No. 22 having cysteine added to the N-end thereof were synthesized by the Fmoc solid phase synthesis method and purified by reverse phase HPLC. Thus 10 mg portions of these peptides were obtained. To the N-terminal cysteine of each of these synthetic peptides, KLH was bound as a carrier protein. By using this binding product as an antigen, a rabbit was immunized and an antiserum was obtained. This antiserum was further purified on an affinity column prepared by binding the synthetic peptide employed as the antigen to an agarose gel. Thus a polyclonal antibody being specific for the synthetic peptide was prepared.

7-b) Staining of S. cerevisiae cells with antibody

A strain S. cervisiae ATCC 9763 was cultured in a YNBG medium [0.67% of yeast nitrogen base (manufactured by Difco), 2% of glucose] to thereby give a suspension of a concentration of 3×10$^7$ cells/ml. To 1 ml of this cell suspension were added 0.11 ml of a 1 M phosphate buffer (pH 6.5) and 0.17 ml of 37% formaldehyde. After slowly stirring at room temperature for 1 hour, the cells were harvested by centrifugation and then suspended in 20 ml of an SS buffer (1 M of sorbitol, 0.2% of β-mercaptoethanol, 0.1 M phosphate buffer, pH 7.5) containing 20 μg/ml of Zymolyase 20T. After treating at 30° C. for 1 hour, the cells were harvested, washed with the SS buffer, suspended in 1 ml of the SS buffer containing 0.1% of Triton X-100 and then allowed to stand for 10 minutes. This cell suspension was placed on a slide glass which had been coated with poly(L-lysine) and allowed to stand for 10 minutes. Next, a PBS solution containing 1% of albumin (BSA) was dropped thereinto. After allowing to stand at room temperature for 15 minutes, the excessive liquid was removed and then a PBS solution containing BSA containing 0.02 mg/ml of the antiSCAR1-1 antibody was dropped thereinto. After allowing to stand at room temperature for 60 minutes and washing with PBS containing BSA three times, antirabbit IgG antibody labeled with FITC (antibody concentration 0.02 mg/ml) was layered over and allowed to stand at room temperature for 1 hour. After washing with a PBS solution containing BSA, a small amount of a mounting solution, which was a solution prepared by dissolving 0.1 g of p-phenylenediamine in 10 ml of CBS (150 mM of NaCl, 50 mM of CHES, pH 9.5), adjusting the pH value to 9.0 with 10 N NaOH and further adding 90 ml of glycerol, was layered over. Then a cover glass was placed thereon to thereby give a specimen. This specimen was observed under a fluorescence microscope to thereby examine the intracellular distribution of the scaur1 protein. As a result, it was found out that this protein was distributed all over the cells.

Figure 11:
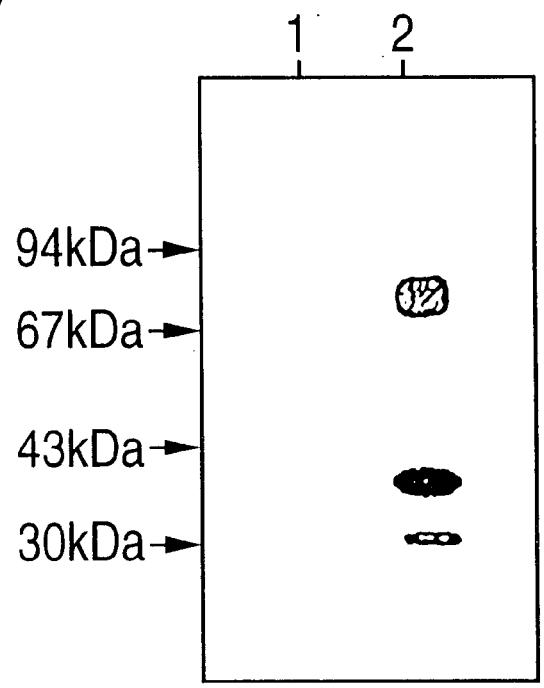
FIG. 11 shows the results of the detection of the scaur1 protein by using an antibody.

7-c) Detection of protein coded for by scaur1 gene by using antibody The plasmid YEpSCARW3 prepared in Example 5-a) was introduced into a normal haploid *S. cerevisiae* SH3328 to thereby give a transformant. This transformant was cultured in a YPGal medium or a YPD medium and the cells were harvested by centrifugation. The cells thus obtained were suspended in a buffer (1% of Triton X-100, 1% of SDS, 20 mM of Tris-HCl, pH 7.9, 10 mM of EDTA, 1 mM of DTT, 1 mM of PMSF). Further, glass beads were added thereto to disrupt the cells by vigorous vortex. Then an SDS loading solution was added thereto and the protein was denatured by treating at 95° C. for 5 minutes. After centrifuging, a part of the obtained supernatant was subjected to SDS-PAGE and the protein thus separated was transfered onto an Immobilon membrane (manufactured by MILLIPORE). This Immobilon membrane was treated with Block Ace (manufactured by Dainippon Pharmaceutical Co., Ltd.). Then the antiSCAR1-2 antibody prepared in 7-a) was reacted therewith as a primary antibody. After washing, antirabbit IgG antibody labeled with peroxidase was reacted therewith as a secondary antibody and the mixture was thoroughly washed. Next, it was color-developed with diaminobenzidine and a band of the scaur1 protein was detected. FIG. 11 shows the results.

FIG. 11 shows the results of the detection of the protein prepared from the cells incubated in the YPD medium (lane 1) and the protein prepared from the cells incubated in the YPGal medium (lane 2), each subjected to SDS-PAGE, by using the antiSCAR1-2 antibody. The cells incubated in the YPGal medium, of which scaur1 gene had been induced, showed a specific band.

Example 8
Construction of chromosome integration vector containing aureobasidin resistant gene 8-a) Construction of replication vector containing scaur1$^R$ A plasmid pSCAR1 was prepared from *Escherichia coli* HB101/pSCAR1 (FERM BP-4483) which carried a plasmid pSCAR1 containing scaur1$^S$. Then the obtained plasmid was partially cleaved with HindIII and thus a DNA of 3.5 kb containing scaur1$^S$ was separated therefrom. This DNA (3.5 kb) was ligated to a vector pUC118 cleaved with HindIII to thereby prepare a plasmid pUscaur1$^S$. This plasmid pUscaur1$^S$ was transformed into *Escherichia coli* CJ236 to thereby prepare ssDNA.

Next, a site-specific DNA mutation was introduced by using Mutan-K kit (manufactured by Takara Shuzo Co., Ltd.) with the use of a synthetic oligonucleotide for introducing mutation represented by SEQ ID No. 37 in the Sequence Listing, which had been synthesized and purified, and the above-mentioned ssDNA. That is to say, the use of the oligonucleotide represented by SEQ ID No. 37 in the Sequence Listing made it possible to obtain scaur1$^R$ wherein the codon TTT of the 158th amino acid residue Phe in the ORF of the gene scaur1$^S$ had been replaced by the codon TAT of Tyr. This plasmid having a DNA coding for Aur1$^R$p (F158Y) was designated as pUscaur1R.

8-b) Amplification of scaur1$^R$ by PCR method

By using the plasmid pUscaur1$^R$ which carried a HindIII fragment of 3.5 kb containing scaur1$^R$, scaur1$^R$ (about 1.9 kb) was amplified by the PCR method. Regarding primers employed herein, XhoI and KpnI sites bad been designed in primers in order to clone the amplified scaur1$^R$ into the plasmid vector pYES2 (manufactured by Invitrogen corporation) and thus primers represented by SEQ ID Nos. 38 and 39 in the Sequence Listing were synthesized.

The reaction was effected in the following manner. 100 μl of a PCR solution containing 28 μl of a PCR buffer [capable of giving final concentrations of 10 mM of S Tris-HCl (pH 8.3), 50 mM of KCl, 1.5 mM of MgCl$_2$, 0.1 mM of dATP, 0.1 mM of dCTP, 0.1 mM of dTTP and 0.1 mM of dGTP], 1 μl of 2.5 U of Ampli Taq DNA polymerase (Manufactured by Perkin-Elmer), 0.5 μl portions of 20 pmol of the primers represented by SEQ ID Nos. 38 and 39 in the Sequence Listing, 1 μl of the plasmid and 69 μl of H$_2$O was maintained at an initial temperature of 94° C. for 1 minute, and then heated successively at 94° C. for 1 minute, at 50° C. for 2 minutes and at 72° C. for 3 minutes. This heating cycle was repeated 35 times. Next, the reaction mixture was maintained at 72° C. for 10 minutes to thereby effect the amplification by PCR. Then the PCR amplification product was cleaved with KpnI and XhoI and electrophoresed on an agarose gel and the target DNA fragment of about 1.9 kb was recovered from the gel and purified by using Suprec™-01 (manufactured by Takara Shuzo Co., Ltd.).

8-c) DNA ligation and transformation

About 0.3 μg of the DNA fragment (about 1.9 kb) purified in the above step was ligated to about 0.1 μg of pYES2, which had been digested with XhoI and KpnI, by using a DNA ligation kit (manufactured by Takara Shuzo Co., Ltd.).

Next, 7 μl of the above-mentioned ligation mixture was added to 200 μl of competent cells of *Escherichia coli* HB101. These cells were allowed to stand on ice for 30 minutes, at 42° C. for 1 minute and then on ice again for 1 minute. Then 800 μl of an SOC medium [Sambrook et al., *Molecular Cloning, A Laboratory Manual,* Cold Spring Harbor Laboratory Press (1989)] was added thereto. After incubating at 37° C. for 1 hour, these *Escherichia coli* cells were spread onto an L-broth agar medium containing 50

μg/ml of ampicillin and incubated at 37° C. overnight. Thus a transformant was obtained.

This transformant was incubated in S ml of an L-broth medium containing 50 μg/ml of ampicillin at 37° C. overnight. From this culture, a plasmid DNA was prepared in accordance with the alkali method (*Molecular Cloning*, cited above). The plasmid thus obtained was named pYES2aur1.

8-d) Construction of chromosome integration vector

About 0.4 μg of the above-mentioned plasmid pYES2aur1 was digested with XbaI and KpnI and electrophoresed on an agarose gel. Then a DNA fragment of about 1.9 kb containing scaur1$^R$ was recovered from the gel and purified by using Suprec-01.

Similarly, about 0.4 μg of the plasmid vector pUC19 was digested with SspI and PvuII and electrophoresed on an agarose gel. Then a DNA fragment (about 1.8 kb) containing an ampicillin resistant gene and ColE1 origin was recovered from the gel and purified. About 0.1 μg portions of these DNA fragments thus purified were blunt-ended with the use of a DNA blunting kit (manufactured by Takara Shuzo Co., Ltd.). Further, about 0.1 μg portions of these blunted DNA fragments were subjected to a ligation reaction. The ligation reaction was effected by using a DNA ligation kit (manufactured by Takara Shuzo Co., Ltd.).

Subsequently, the plasmid was integrated into Escherichia coli JM109. After incubating, a transformant and a plasmid DNA were prepared. The plasmid thus obtained was named plasmid pAUR1. Next, this plasmid was cleaved with StuI to thereby prepare a chromosome integration vector.

Example 9
Construction of chromosome integration vector containing aureobasidin resistant gene 9-a) Amplification of DNA fragment of scaur1$^R$ having mutation introduced therein by PCR In order to replace the 240th amino acid residue Ala of Aur1$^R$p (F158Y) by Cys, a primer, wherein the codon GCT of Ala had been changed into the codon TGT of Cys, represented by SEQ ID No. 48 in the Sequence Listing was synthesized and purified. By using the plasmid pUscaur1$^R$ described in Example 8-a), which carried a HindIII fragment (3.5 kb) containing scaur1$^R$ at the HindIII site of pUC119, as a template, was amplified a DNA fragment (about 1.4 kb) which contained a sequence of about 500 bp coding for the amino acid sequence on the C-terminal side of Aur1$^R$p (F158Y, A240C), wherein GCT had been changed into TGT, by the PCR method with the use of the primer represented by SEQ ID No. 48 in the Sequence Listing and a primer M13M4. The PCR was effected in the following manner. To 28 μl of a PCR buffer [capable of giving final concentrations of 10 mM of Tris-HCl (pH 8.3), 50 mM of KCl, 1.5 mM of MgCl$_2$, 0.1 mM of dATP, 0.1 mM of dCTP, 0.1 mM of dTTP and 0.1 mM of dGTP] were added 2.5 U of Ampli Taq DNA polymerase, 100 pmol portions of the primer represented by SEQ ID No. 48 in the Sequence Listing and the primer M13M4, 1 ng of pUscaur1$^R$ and distilled water to thereby give 100 μl of a PCR solution. This reaction mixture was then heated successively at 94° C. for 1 minute, at 55° C. for 1.5 minutes and at 72° C. for 1.5 minutes. This cycle was repeated 30 times. Next, the PCR product was cleaved with SalI and SnaI and electrophoresed on an agarose gel. The target DNA fragment of about 1.3 kb was recovered from the gel and purified.

9-b) Construction of plasmid containing DNA coding for Aur1$^R$p (F158Y, A240C)

pUscaur1$^R$ was cleaved with SalI and SnaI and electrophoresed on an agarose gel. The target DNA fragment of 5.3 kb was recovered and purified. To this DNA fragment was ligated the DNA fragment of 1.3 kb obtained in Example 9-a). The obtained plasmid, which had a DNA (scaur1$^R$-C) coding for Aur1$^R$p (F158Y, A240C), was named pUscaur1$^R$-C. To effect transformation by integrating it into the chromosome of sake yeast, pUscaur1$^R$-C was linearized by cleaving with StuI prior to use. As a control, pUscaur1$^R$ was also linearized with StuI.

9-c) Construction of plasmid containing DNA coding for Aur1$^R$p (A240C) pUscaur1$^S$ was cleaved with SalI and SnaI and electrophoresed on an agarose gel. The target DNA fragment of 5.3 kb was recovered and purified. This DNA fragment was ligated the DNA fragment of 1.3 kb obtained in Example 9-a). The obtained plasmid, which had a DNA coding for Aur1$^R$p (A240C) wherein the 240th residue Ala of Aur1$^S$p had been replaced by Cys, was named pUscaur1A240C. To effect transformation by integrating it into the chromosome of sake yeast, pUscaurA240C was linearized by cleaving with StuI prior to use.

Example 10
Transformation by using sake yeast as host 10-a) About 10 μg of the linearized vector of the plasmid pAUR1 described in Example 8 was introduced into Sake yeast Kyokai k-701 by the lithium acetate method [*Journal of Bacteriology*, 153, 163 (1983)].

Namely, to Sake yeast Kyokai K-701, which had been suspended in a 0.1 M lithium acetate solution (about 1.3×10$^8$ cells/100 μl of 0.1 M lithium acetate), was added 10 μg of the vector which had been prepared through the linearization of scaur1$^R$ by cleaving with StuI at one position. After treating at 30° C. for 30 minutes and then at 42° C. for 15 minutes, the cells were harvested by centrifugation and pre-incubated in 5 ml of a YPD liquid medium. After pre-incubating in a YPD liquid medium containing 0.4 μg/ml of aureobasidin A, transformants were obtained on a YPD agar medium containing 0.8 μg/ml of aureobasidin A. This transformant was named Sake yeast Kyokai K-701/pAUR1.

This transformant was subcultured over three generations in the absence of aureobasidin A and then the sensitivity to aureobasidin was assayed. As a result, it showed eight times as much aureobasidin resistance (MIC 1.56 μg/ml) as that of the parent strain (i.e., Sake yeast Kyokai K-701), which indicated that the aureobasidin resistance was sustained. Thus it has been confirmed that the aureobasidin resistance introduced on the host chromosome is usable as a selective marker.

10-b) To compare the activities of pUscaur1$^R$-C prepared in Example 9-b), pUscaur1A240C prepared in Example 9-c) and pUscaur1$^R$ prepared in Example 8-a), 5 μg of the plasmid, which had been linearized with StuI, was introduced into Sake yeast Kyokai K-701 by the lithium acetate method. Namely, to sake yeast, which had been suspended in a 0.1 M lithium acetate solution (pH 7.5) and made competent, were added 5 μg of the plasmid, which had been linearized by cleaving with StuI at one position, and 850 μl of 40% polyethylene glycol/0.1 M lithium acetate. After treating at 30° C. for 30 minutes and then maintaining at 42° C. for 15 minutes, the cells were harvested, pre-incubated in 5 ml of a YPD liquid medium for 1 hour or overnight and then smeared on a YPD agar medium containing aureobasidin A at various concentration. After incubating at 30° C. for 3 to 4 days, transformants having a resistance to aureobasidin A were obtained. As Table 4 shows, the transformant prepared by using the StuI-linearized pUscaur1$^R$-C could grow even in the medium containing 5 μg/ml of aureobasidin A. These transformants sustained an aureobasidin A resistance at least 10 times higher than that of the parent strain even after being subcultured over several generations. The transformant obtained by using the linearized pUscaur1$^R$-C showed an MIC to aureobasidin A of 20 μg/ml or above. Thus it has been confirmed that the Aur1$^R$p (F158Y, A240C) is usable as an effective selective marker for sake yeast. As Table 4 shows, the StuI-linearized pUscaur1A240C exceeded the StuI-linearized pUscaur1$^R$ in the activity of imparting resistance. That is to say, the mutation at the 240th residue Ala resulted in the expression of the activity of imparting a stronger resistance.

TABLE 4

| Plasmid | Pre-incubation time | No. of transformants/μg DNA Aureobasidin A concn. (μg/ml) | | |
|---|---|---|---|---|
| | | 0.5 | 1.0 | 5.0 |
| StuI-linearized pUscaur1R | 1 hour | 0 | 0 | 0 |
| | overnight | 5 | 4 | 0 |
| StuI-linearized pUscaur1R-C | 1 hour | 170 | 73 | 0 |
| | overnight | 2368 | 2024 | 64 |
| StuI-linearized pUscaur1A240C | 1 hour | 18 | 1 | 0 |
| | overnight | 160 | 152 | 0 |
| no plasmid (control) | 1 hour | 0 | 0 | 0 |
| | overnight | 0 | 0 | 0 |

Example 11
Transformation by chromosome integration vector having aureobasidin resistant gene and AARE gene 11-a) Construction of plasmid containing AARE gene 0.5 μg of the plasmid pAUR1 was cleaved with SphI and electrophoresed on an agarose gel. Then the linearized plasmid pAUR1 was recovered from the gel and purified.

Next, a plasmid pYHA201 was prepared from a yeast BJ2168, which carried a plasmid pYHA201 containing the AARE gene described in Japanese Patent Laid-Open No. 254680/1991 (i.e., Saccharomyces cerevisiae BJ2168/pYHA201; FERM P-11570). 0.5 μg of this plasmid pYHA201 was digested with SphI and the DNA fragments (about 3.2 kb) were isolated and purified.

This DNA fragment of about 3.2 kb contained the AARE gene bound to the downstream of the ADHI promotor.

By using each 0.2 μg portions of both the purified SphI-cleaved DNA fragments, a ligation reaction was effected by using a DNA ligation kit (manufactured by Takara Shuzo Co., Ltd.). Subsequently, the plasmid was integrated into Escherichia coli JM109 and incubated to thereby give a transformant and a plasmid DNA. The plasmid thus obtained was named plasmid pAUR1aare, while the transformant thus obtained was named and indicated as Escherichia coli JM109/pAUR1aare and has been deposited at National Institute of Bioscience and Human-Technology, Agency of Industrial Science and Technology under the accession number FERM P-14366.

11-b) Expression of AARE in sake yeast

By using about 10 μg of the above-mentioned plasmid pAUR1aare, the plasmid pAUR1aare linearized was transformed into Sake yeast Kyokai K-701 in the same manner as the one described in Example 10. Then an aureobasidin resistant transformant was obtained on a YPD agar medium containing 0.4 μg/ml of aureobasidin A.

The transformant thus obtained was named and indicated as Saccharomyces cerevisiae K701/pAUR1aare and has been deposited at National Institute of Bioscience and Human-Technology, Agency of Industrial Science and Technology under the accession number FERM P-14379.

Next, this transformant was inoculated into 5 ml of a minimal medium [0.67% of Bacto Yeast Nitrogen Base w/o Amino Acid (manufactured by Difco), 2% of glucose] and incubated at 30° C. for two days and then the cells were harvested by centrifugation.

After discarding the supernatant, the cells were washed with 2 ml of water and harvested again by centrifugation.

Subsequently, the cells were suspended in 700 μl of a 0.2 M sodium phosphate buffer Solution (pH 7.2).

To this suspension were added 400 μl of glass beads (0.40 to 0.60 mm in diameter) and the cells were disrupted by vigorously stirring under ice-cooling.

After centrifuging, the supernatant was recovered and regarded as a extract.

Also, extracts of Sake yeast Kyokai K-701 and Sake yeast Kyokai K-701/pAUR1 obtained in Example 10 were prepared in the same manner.

The acylamino acid releasing enzyme activity of each of the extracts thus obtained was measured by the following method. 0.89 ml of a 0.5% dimethylformamide-0.2 M sodium phosphate buffer solution (pH 7.2) containing 0.020 mM of an amide prepared from N-acetyl-L-methionine and 7-amino-4-methylcoumarin (AMC) was preheated at 37° C. for about 5 minutes. Then 100 μl of the above-mentioned extract was added thereto and the resulting mixture was incubated at 37° C. for 15 minutes. After the completion of the reaction, 10 μl of 10% SDS was added to thereby cease the reaction and the intensity of fluorescence was measured with a fluorophotometer. Namely, the excitation wavelength and the measurement wavelength were set respectively to 380 nm and 440 nm. The amount of the liberated AMC was determined by preparing a standard curve with the use of AMC samples of known concentrations and comparing the obtained data therewith.

100 μl of the extract of S. cerevisiae K701/pAUR1aare had an activity of liberating about 25 pmol of AMC in 15 minutes in the above reaction system.

On the other hand, the extract of Sake yeast Kyokai K-701 having no plasmid and the extract of Sake yeast Kyokai K-701/pAUR1 obtained in Example 10 showed each no AARE activity.

Further, an analysis was effected by the southern hybridization with the use of the aureobasidin resistant gene as a probe. As a probe in the hybridization, use was made of an scaur1$^R$ fragment (about 1.6 kb) which had been amplified by the PCR method with the use of the plasmid pAUR1 as a template and the primers represented by SEQ ID Nos. 40 and 41 in the Sequence Listing. 100 ng of the fragment thus obtained was labeled with [$^{32}$P]dCTP by using a Bca-BEST™ labeling kit. The genomic DNAs of Sake yeast Kyokai K-701 and Saccharomyces cerevisiae K701/pAUR1aare were cleaved with various restriction enzymes (HpaI having no cleavage site on pAUR1aare, BamHI having two cleavage sites on pAUR1aare), electrophoresed on an agarose gel and transferred onto the hybridization filter.

Figure 14:
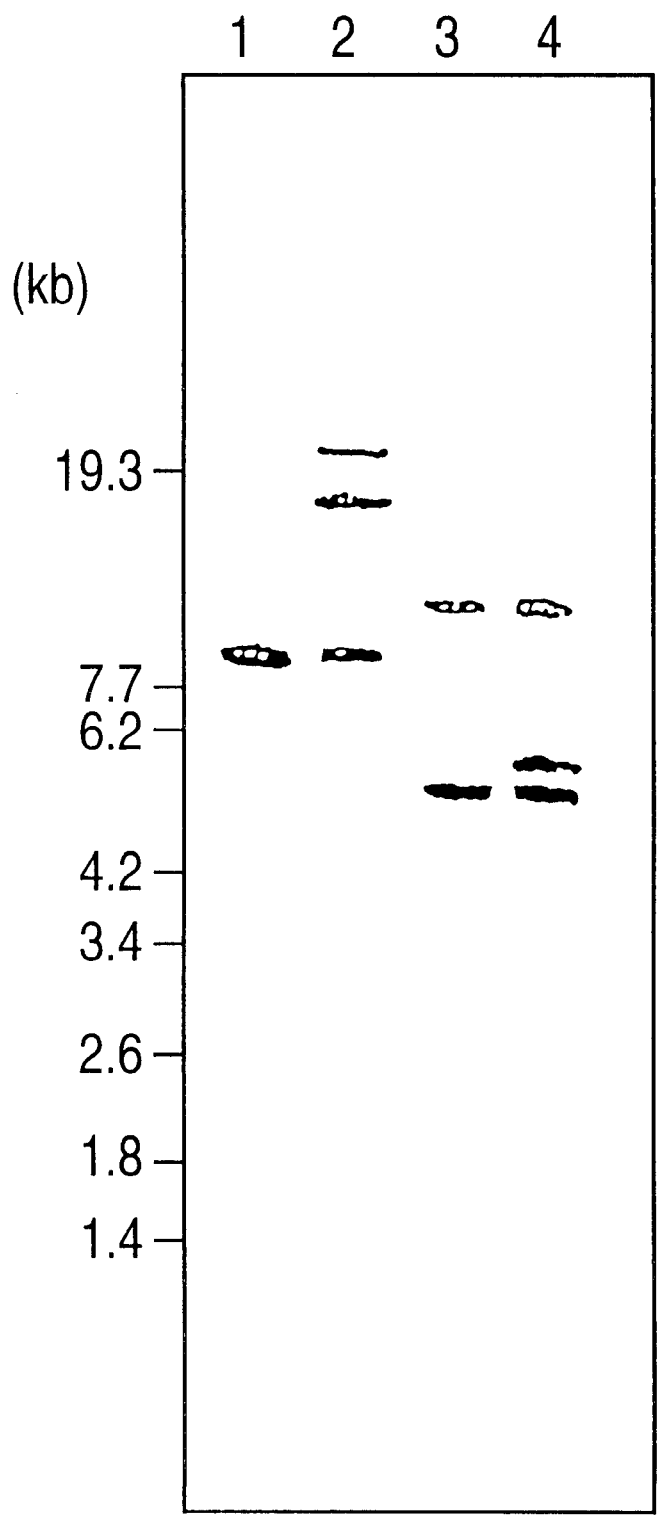
FIG. 14 shows a pattern of the southern hybridization after electrophoresis of the genomic DNA digested by a restriction enzyme.

In FIG. 14, the lanes 1 and 2 show the results obtained by cleaving the genomic DNA of Sake yeast Kyokai K-701 with HpaI (lane 1) or BamHI (lane 3) and subjected to southern hybridization, while the lanes 2 and 4 show the results obtained by cleaving the genomic DNA of Saccharomyces cerevisiae K701/pAUR1aare with HpaI (lane 2) or BamHI (lane 4) and subjected to southern hybridization. Since HpaI had no cleaving site on the plasmid pAUR1aare but cleaved exclusively the genomic DNA, it was proved from the lanes 1 and 2 that the aureobasidin resistant gene had been integrated into one of a pair of chromosomes.

It was confirmed from the lanes 3 and 4 that the aureobasidin resistant gene had been homologously integrated into the aureobasidin sensitive gene on the chromosome of the sake yeast.

These results indicate that genes of the sake yeast were not disrupted by the random integration of the aureobasidin resistant gene.

As described above, by using the chromosome integration vector of the present invention, the resistance could be imparted to an aureobasidin sensitive fungi and, furthermore, a foreign gene could be expressed.

Example 12
Construction of recombinant plasmid containing aureobasidin resistant gene 12-a) Construction of pYC vector carrying DNA coding for Aurl$^R$p (F158Y, A240C)

By employing pUscaurl$^R$-C as a template, PCR was effected with the use of primers represented by SEQ ID Nos. 49 and 59 in the Sequence Listing. The PCR product (about 2.2 kb), which contained the DNA coding for the amplified Aurl$^R$p (F158Y, A240C), was cleaved with XhoI and KpnI and blunt-ended with the use of a blunting kit (manufactured by Takara Shuzo Co., Ltd.).

A pYC vector pYEUra3 (manufactured by Clontech Laboratories, Inc.) was cleaved with EcoRI and BamHI and blunt-ended with the use of a blunting kit. Then it was ligated to the blunt-ended PCR product (about 2.2 kb) described above. The plasmid thus obtained was named pYCscaurl$^R$-C. By employing pUscaurl$^R$ as a template, PCR was effected in the same manner with the use of primers represented by SEQ ID Nos. 49 and 50 in the Sequence Listing. The PCR product (about 2.2 kb), which contained the DNA coding for the amplified Aurl$^R$p (F158Y), was cleaved with XhoI and KpnI and blunt-ended with the use of a blunting kit (manufactured by Takara Shuzo Co., Ltd.). A pYEUra3 was cleaved with EcoRI and BamHI and blunt-ended with the use of a blunting kit. Then it was ligated to the blunt-ended PCR product (about 2.2 kb) described above. The plasmid thus obtained was named pYCscaurlR.

12-b) Construction of pYE vector carrying DNA coding for Aurl$^R$p (F158Y, A240C)

By using pUscaurl$^R$-C as a template, the DNA fragment (about 2.2 kb), which contained the DNA coding for Aurl$^R$p (F158Y, A240C), was amplified by the PCR method with the use of a primer represented by SEQ ID No. 49 in the Sequence Listing and a primer M13M4. The PCR product was cleaved with BamHI and electrophoresed on an agarose gel. Then the target DNA fragment (about 1.8 kb) was recovered from the gel and purified. The plasmid pSCAR1 was cleaved with BamHI and thus a DNA fragment of 11.7 kb, from which a DNA fragment of 2.8 kb containing scaurl$^S$ had been deleted, was obtained. This DNA fragment of 11.7 kb was ligated to the above-mentioned DNA fragment of 1.8 kb containing the DNA coding for Aurl$^R$p (F158Y, A240C). Then a plasmid having the fragment of 1.8 kb inserted thereinto in the desired direction was selected. This plasmid containing the DNA coding for Aurl$^R$p (F158Y, A240C) was named pWscaurl$^R$-C and employed in the transformation of a yeast for laboratory use.

Example 13
Transformation with the use of yeast as host 13-a) Transformation of sake yeast by pYCscaurl$^R$-C By using 5 μg of a pYC plasmid pYCscaurl$^R$-C, Sake yeast Kyokai K-701 was transformed by the lithium acetate method described in Example 8-a). As Table 5 shows, the obtained results are similar to those obtained in the cases of the linearized plasmids. These transformants sustained each an aureobasidin A resistance at least 10 times higher than that of the parent strain even after being subcultured over several generations. Thus it has been confirmed that Aurl$^R$p (F158Y, A240C) is usable as an effective selective marker for sake yeast in the transformation by a replication vector.

TABLE 5

| Plasmid | Pre-incubation time | No. of transformants/μg DNA Aureobasidin A concn. (μg/ml) | | | |
|---|---|---|---|---|---|
| | | 0.5 | 1.0 | 2.0 | 5.0 |
| pYCscaurlR | 1 hour | 0 | 0 | 0 | 0 |
| | overnight | 24 | 21 | 0 | 0 |
| pYCscaurl$^R$-C | 1 hour | 386 | 172 | 18 | 1 |
| | overnight | 4824 | 4792 | 1692 | 136 |

13-b) Transformation of laboratory yeast by pWscaurl$^R$-C

By using a monoploid yeast DKD-5D for laboratory use (a, his3, trp1, leu2-3, 112) as a host, 5 μg of pWscaurl$^R$-C was transformed by the lithium acetate method described in Example 10-a).

For comparison, a transformant was screened on a minimal medium by using an auxotrophic marker contained in the plasmid. As Table 6 shows, it has been confirmed that Aurl$^R$p (F158Y, A240C) is usable as a selective marker which is comparable to the conventional auxotrophic markers in a monoploid yeast.

TABLE 6

| Plasmid | Pre-incubation time | No. of transformants/μg DNA Minimal Aureobasidin A concn. (μg/ml) | | | |
|---|---|---|---|---|---|
| | | medium | 0.5 | 1.0 | 5.0 |
| pWCscaurl$^R$-C | 1 hour | 192 | 248 | 181 | 58 |
| | overnight | 2500 | 2780 | 2524 | 2044 |

Example 14
Transformation by using C. albicans as host 14-a) 5 μg of a linear plasmid, which had been prepared by cleaving pUscaurl$^R$-C with SalI capable of cleaving at one point in the pUC119 region, was transformed into C. albicans TIMM0136 by the lithium acetate method. After the completion of the transformation, the cells were incubated in a YPD medium for 1 hour or overnight and then smeared on a YPD agar medium containing aureobasidin A. As Table 7 shows, transformants having the resistance to aureobasidin were obtained by effecting the pre-incubation overnight. These transformants showed each an MIC of 10 μg/ml or above.

TABLE 7

| Plasmid | Pre-incubation time | No. of transformants/μg DNA Aureobasidin A concn. (μg/ml) | |
|---|---|---|---|
| | | 0.25 | 1.0 |
| SalI-linearized pUscaurl$^R$-C | 1 hour | 0 | 0 |
| | overnight | 180 | 0 |

Example 15
Cloning of gene anaurl regulating aureobasidin sensitivity and originating in A. nidulans 15-a) Isolation of aureobasidin resistant mutant of A. nidulans A strain A. nidulans FGSC89 showing a sensitivity to aureobasidin at 5 μg/ml was inoculated into an SD slant (containing 1% of polypeptone S, 2% of glucose and 2% of agar) and incubated therein at 30° C. for 7 days. After suspending in S ml of a 0.1% Tween 80 solution containing 0.8% of NaCl, the suspension was filtered through a glass filter (3G3 type) and the obtained filtrate was used as a conidium suspension. This conidium suspension was UV-radiated for 5 minutes, thus effecting mutagenesis. Under these conditions, the rate of survival was about 25%. After blocking off the light for 30 minutes or longer, the conidia were inoculated into an SD plate and incubated at 30° C. for 4 days. The conidia thus formed were collected with a glass filter, further inoculated into Cz+bi medium [containing 4.9% of Czapek solution agar (manufactured by Difco), 200 µg/ml of arginine and 0.02 µg/ml of biotin] containing 5 µg/ml of aureobasidin and incubated therein at 30° C. After 2 or 3 days, eight aureobasidin resistant colonies were obtained. Although these cells showed a resistance to 80 µg/ml of aureobasidin, they were the same as the parent strain in the sensitivities to amphotericin B, cycloheximide and clotrimazole. Thus it was estimated that the resistance thus acquired was not a multiple drug resistance but one specific to aureobasidin.

15-b) Preparation of genomic library of aureobasidin resistant strain

From a strain R1 showing a particularly high resistance from among the aureobasidin resistant strains, genomic DNAs were extracted and purified in the following manner. After incubating in a PD medium [containing 2.4% of potato dextrose broth (manufactured by Difco)] under shaking at 30° C. for 2 days, the hyphae were collected with a glass filter (3G1 type) and washed with distilled water. Then the cells were dehydrated and suspended in 20 ml of a protoplast generation solution [containing 20 µg/ml of Yatalase (manufactured by Ozeki Shuzo), 0.8 M of NaCl and 10 mM of a sodium phosphate buffer, pH 6.0]. Then the suspension was slowly stirred at 30° C overnight to thereby generate protoplasts. The suspension was filtered through a glass filter (3G2 type) and thus the protoplasts were collected into the filtrate and then harvested by centrifuging at 2,000 rpm for 5 minutes. After washing with 0.8 M NaCl twice, the protoplasts were suspended in 2 ml of a TE solution (containing 10 mM of Tris-HCl and 1 mM of EDTA, pH 8.0) and 2 ml of a lysis solution (containing 2% of SDS, 0.1 M of NaCl, 10 mM of EDTA and 50 mM of Tris-HCl, pH 7.0) was added thereto. After slowly stirring, the mixture was maintained at room temperature for 15 minutes and then centrifuged at 3,500 rpm for 10 minutes followed by the recovery of the supernatant. Then an equivalent amount of a mixture of phenol/chloroform/isoamyl alcohol (25/24/1) was added thereto and the mixture in the tube was gently mixed and centrifuged at 3,000 rpm for 5 minutes followed by the recovery of the upper liquid layer. Next, 2.5 times by volume as much ethanol at −20° C. was added thereto. The resulting mixture was allowed to stand at −80° C. for 10 minutes and then centrifuged at 3,500 rpm for 15 minutes. The DNAs thus precipitated were dried. Then 0.5 ml of a TE solution and 2.5 µl of an RNase A solution (20 µg/ml) were added thereto and the mixture was maintained at 37° C. for 30 minutes.

After adding 0.5 ml of phenol/chloroform/isoamyl alcohol, the obtained mixture was gently mixed and centrifuged at 10,000 rpm for 5 minutes followed by the recovery of the upper layer. This procedure was repeated once. After adding 0.5 ml of chloroform/isoamyl alcohol (24/1), the obtained mixture was gently mixed and centrifuged at 10,000 rpm for 5 minutes followed by the recovery of the supernatant. Then 0.05 ml of 5 M NaCl and 0.5 ml of isopropyl alcohol were added and the mixture was allowed to stand at −80° C. for 10 minutes and centrifuged at 10,000 rpm for 15 minutes to thereby collect DNAs.

Eight µg of the genomic DNAs thus purified were partially digested by treating with 4 U of a restriction enzyme BamHI at 37° C. for 15 minutes. After deprotenization with phenol/chloroform, the DNA was recovered by ethanol precipitation. The DNAs were electrophoresed on a 0.8% agarose gel and DNAs in a region of from 3 to 15 kb were extracted and purified. The DNAs thus obtained were ligated to a vector pDHG25 [Gene, 98, 61–67 (1991)], which had been completely digested with BamHI, with the use of a DNA ligation kit (manufactured by Takara Shuzo Co., Ltd.). Then *Escherichia coli,* HB101 was transformed thereby so as to prepare a genomic library of the resistant strain. The *E. coli* cells containing this genomic library were cultured in 50 ml of an LB medium (containing 1% of bactotrypton, 0.5% of bacto yeast extract and 0.5% of sodium chloride) containing 100 µg/ml of ampicillin at 37° C. overnight. Next, plasmids were recovered and purified from the *E. coli* cells.

15-c) Expression and cloning of aureobasidin resistant gene anaurl$^R$

The plasmid originating in the genomic library of the aureobasidin resistant strain thus obtained was transformed into a strain *A. nidulans* FGSC89 by the following method. Namely, *A. nidulans* was incubated in a PD medium under shaking at 30C for 2 days. Then the hyphae were collected by filtering the culture broth through a glass filter (3G1 type) and washed with sterilized water. After sufficiently dehydrating, the cells were suspended in 10 ml of a protoplast generation solution. After reacting by slowly shaking at 30° C. for about 3 hours, the cell suspension was filtered through a glass filter 3G3. Then the filtrate was centrifuged at 2,000 rpm for 5 minutes to thereby collect the protoplasts therein. The collected protoplasts were washed with 0.8 M NaCl twice and suspended in Sol 1 (containing 0.8 M of NaCl, 10 mM of CaCl$_2$ and 10 mM of Tris-HCl, pH 8.0) in such a manner as to give a protoplast concentration of 2×10$^8$/ml. Then 0.2 time by volume as much Sol 2 [containing 40% (w/v) of PEG4000, 50 mM of CaCl$_2$ and 50 mM of Tris-HCl, pH 8.0] was added thereto and well mixed.

10 µg of the plasmid originating in the genomic library was added to a 0.2 ml portion of the protoplast suspension. After mixing well, the mixture was allowed to stand in ice for 30 minutes and then 1 ml of Sol 2 was added thereto. After mixing well, the mixture was allowed to stand at room temperature for 15 minutes and then 8.5 ml of Sol 1 was added thereto. After mixing well, the mixture was centrifuged at 2,000 rpm for 5 minutes to thereby collect the protoplasts. 0.2 ml of Sol 1 was added thereto and the resulting mixture was placed on the center of a minimum medium plate (containing 4.9% of Czapek solution agar, 0.8 M of NaCl and 0.02 µg/ml of biotin) containing 5 µg/ml of aureobasidin. Next, 5 ml of a soft agar medium (containing 3.5% of Czapek-Dox broth, 0.8 M of NaCl, 0.02 µg/ml of biotin and 0.5% of agar) was layered thereon followed by incubation at 30° C. for 3 to 5 days. It was considered that the colonies growing on this plate carried a plasmid containing an aureobasidin resistant gene.

Thus, about 70 colonies were formed on the aureobasidin-containing medium. These colonies were transplanted into 20 ml of a Cz+Bi medium and incubated at 30° C. for 2 days. Then DNA was recovered and purified from the cells thus propagated in accordance with the method for the extraction and purification of DNA described in Example 15-b). A strain *E. coli* HB101 was transformed by this DNA and spread on an LB plate containing 100 µg/ml of ampicillin.

Figure 15:
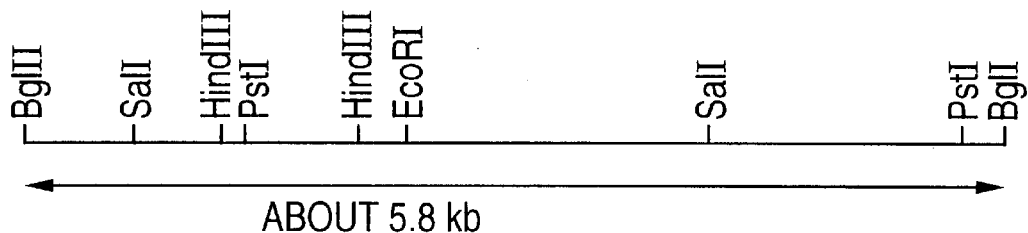
FIG. 15 is a diagram showing the restriction enzyme map of the genomic DNA of a gene anaur1$^R$ regulating aureobasidin sensitivity.
Figure 19:
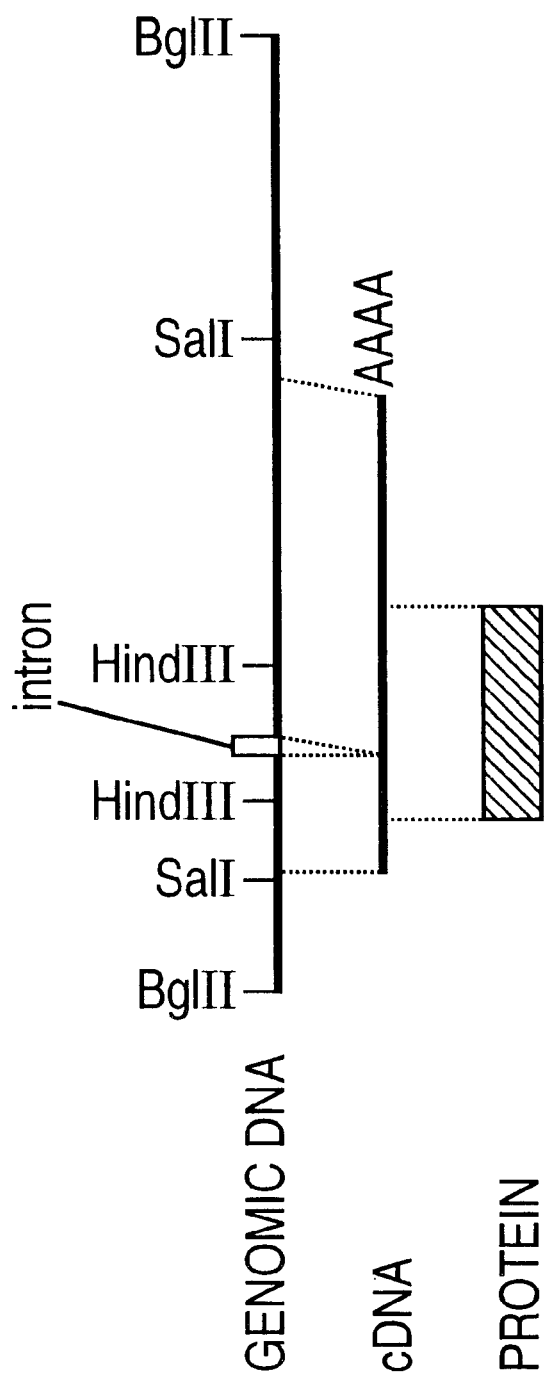
FIG. 19 is a diagram showing a relation among the genomic DNA, cDNA and protein of a gene anaur1 regulating aureobasidin sensitivity.

Then a plasmid DNA was prepared from the E. coli colonies thus formed. This plasmid contained a DNA of 12 kb and was named pR1-1. FIG. 19 shows the restriction enzyme map of the 12 kb DNA contained in pR1-1. To further specify the resistant gene region, the DNA fragment of 12 kb was digested into fragments of various sizes with restriction enzymes. Next, these fragments were cloned into a vector pDHG25. Plasmids containing various DNAs were transformed into a strain A. nidulans FGSC89 so as to confirm whether the aureobasidin resistance could be thus acquired or not. As a result, it was revealed that the activity of imparting aureobasidin resistance resided in a fragment Bgl II (5.8 kb). Thus it was clarified that the gene anaur1$^R$ was located in this fragment. FIG. 15 shows the restriction enzyme map of this DNA fragment containing the aureobasidin resistant gene anaur1$^R$. This fragment was subcloned into a vector pUC118 and the obtained plasmid was named pUR1. By using this plasmid, the DNA sequence of the DNA was identified. SEQ ID NO. 1 in the Sequence Listing shows this base sequence. As this DNA sequence indicates, the gene anaur1$^R$ is one composed of two exon regions containing an intron. It has been revealed that this gene encodes a protein having the amino acid sequence represented by SEQ ID NO. 2 in the Sequence Listing.

15-d) Cloning of aureobasidin sensitive gene anaur1$^S$

Figure 16:
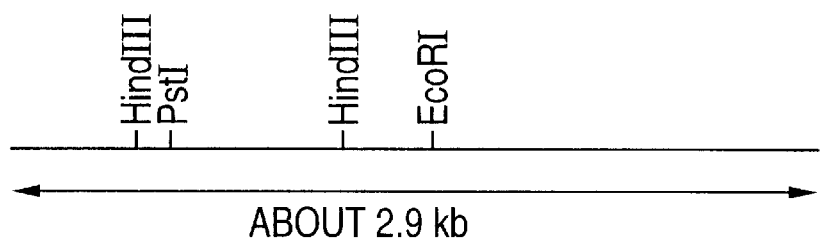
FIG. 16 is a diagram showing the restriction enzyme map of the cDNA of a gene anaur1$^s$ regulating aureobasidin sensitivity.
Figure 17:
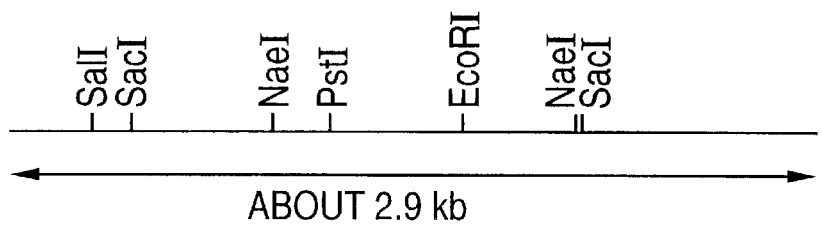
FIG. 17 is a diagram showing the restriction enzyme map of the cDNA of a gene afaur1$^s$ regulating aureobasidin sensitivity.

To obtain the cDNA of the aureobasidin sensitive gene from normal cells of A. nidulans, total RNAs were first extracted from a strain A. nidulans FGSC89. Namely, this strain was incubated in 200 ml of a PD medium and the cells were collected with the use of a glass filter (3G1 type). After sufficiently dehydrating, the cells were quickly frozen with liquid nitrogen. Then the frozen cells were powdered in a mortar and total RNAs (2.6 mg) were extracted and purified with the use of an RNA extraction kit (manufactured by Pharmacia). From 1 mg of these RNAs, 12.8 μg of poly(A)$^+$ RNAs were prepared by using Oligotex-dT30 <Super> (manufactured by Takara Shuzo Co., Ltd.). By using 5 μg of the poly(A)$^+$RNAs, cDNAs were synthesized with the use of a Takara cDNA synthesizing kit (manufactured by Takara Shuzo Co., Ltd.). The cDNAs thus synthesized were ligated to a λ phage vector λSHlox™ (manufactured by Novagen, Inc.) and subjected to in vitro packaging with the use of Phage Maker™ System, Phage Pack Extract (manufactured by Novagen, Inc.) to thereby construct a cDNA library. This cDNA library was infected in a host strain E. coli ER1647. After mixing with top agarose (an LB medium containing 0.7% of agarose), it was layered on an LB plate and incubated at 37° C. overnight to thereby form plaques. The plaques thus formed were transferred onto a nylon membrane (Hybond-N, manufactured by Amersham) and subjected to plaque hybridization. As a probe, use was made of a DNA fragment of 2.6 kb obtained by cleaving the plasmid pUR1 obtained in Example 15-c) with PstI and SalI. This DNA fragment was labeled with [α-$^{32}$p]dCTP by using a random primer DNA labeling kit (manufactured by Takara Shuzo Co., Ltd.) and employed as a probe in the hybridization. As the result of screening of 4×10$^5$ plaques, 8 phage clones hybridizable with the probe were obtained. Next, these phages were subjected to automatic subcloning in E. coli to thereby give E. coli strains having plasmids wherein a cDNA-containing region had been automatically subcloned. The plasmids were purified from these strains and the cDNAs were compared in length. Thus pSl5 having the longest cDNA (2.9 kb) was selected and subcloned into pUC118 followed by the identification of the DNA sequence. This plasmid was named pANAR1. An E. coli strain transformed by pANAR1 was named Escherichia coli JM109/pANAR1 and has been deposited at National Institute of Bioscience and Human-Technology, Agency of Industrial Science and Technology under the accession number FERM BP-5180. FIG. 16 shows the restriction enzyme map of this cDNA. The DNA base sequence thereof is represented by SEQ ID NO. 3 in the Sequence Listing. As this base sequence indicates, the gene anaur1$^S$ encodes a protein having the amino acid sequence represented by SEQ ID NO. 4 in the Sequence Listing. A comparison with the resistant gene anaur1$^R$ has revealed that the base G at the position 1218 in SEQ ID NO. 3 has been mutated into T and, at the amino acid level, the amino acid glycine at the position 275 has been converted into valine. It has been further clarified that the genomic DNA has one intron (56 bp). FIG. 19 shows the relation between the genomic DNA and cDNA.

Example 16

Figure 20:
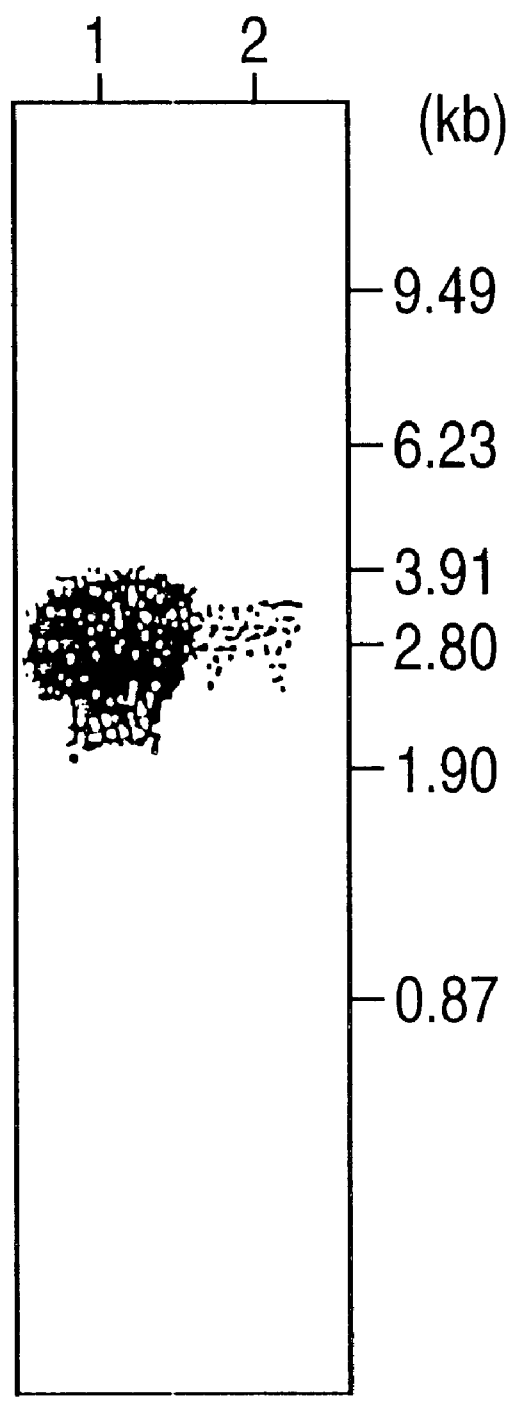
FIG. 20 is a diagram showing the results of Northern hybridization of genes regulating aureobasidin sensitivity of *A. nidulans* and *A. fumigatus*.

Confirmation and cloning of gene afaur1$^S$ carried by A. fumigatus 16-a) Detection of gene afaur1$^S$ by Northern hybridization From a strain A. fumigatus TIMM1776, poly(A)$^+$RNAs were extracted and purified by the same method as the one of Example 15-d). The poly(A)$^+$RNAs (1 μg) of A. fumigatus and A. nidulans were separated by electrophoresing on a 1.2% agarose gel containing formaldehyde and transferred onto a nylon membrane. After fixing, hybridization was effected with the use of a HindIII fragment (741 bp) of the cDNA of the gene anaur1$^S$ labeled with [α-$^{32}$p] dCTP as a probe. After hybridizing at 60° C. overnight, the mixture was washed at 60° C. with 0.5×SSC and 0.1% SDS. In FIG. 19, the lanes 1 and 2 show the results of the hybridization of the poly(A)$^+$RNAs obtained from A. nidulans and A. fumigatus respectively. As FIG. 20 clearly shows, autoradiography of the hybridization revealed that A. fumigatus and A. nidulans both had the aureobasidin sensitive genes of the same size. However, the band of A. fumigatus was very weak, which indicates that the homology between these genes is not so high.

16-b) Cloning of gene afaur1$^s$ carried by A. fumigatus

By using the poly(A)$^+$RNAs of A. fumigatus purified in Example 16-a), a cDNA library of A. fumigatus was prepared in accordance with the method for the preparation of a cDNA library described in Example 15-d). The above-mentioned library was screened under the same hybridization conditions as those of Example 16-a) with the use of a PstI-EcoRI fragment (921 bp) of the cDNA of A. nidulans as a probe. Thus eight phage clones were obtained. From these phage clone, the cDNA was recovered in the form of a plasmid by the method described in Example 15-d). The plasmids were purified and the cDNAs were compared in length. Thus the plasmid having the longest cDNA (2.9 kb) among them was selected. This cDNA was subcloned into pUC118 and the DNA sequence was identified. This base sequence, which is represented by SEQ ID NO. 12 in the Sequence Listing, indicates that this gene encodes a protein having the amino acid sequence represented by SEQ ID NO. 5 in the Sequence Listing. A comparison between the amino acid sequence of the afaur1$^s$ protein of the strain A. fumigatus TIMM1776 with that of the anaur1$^s$ protein of the strain A. nidulans FGSC 89 indicated that they had a high homology (87%).

Example 17

Figure 21:
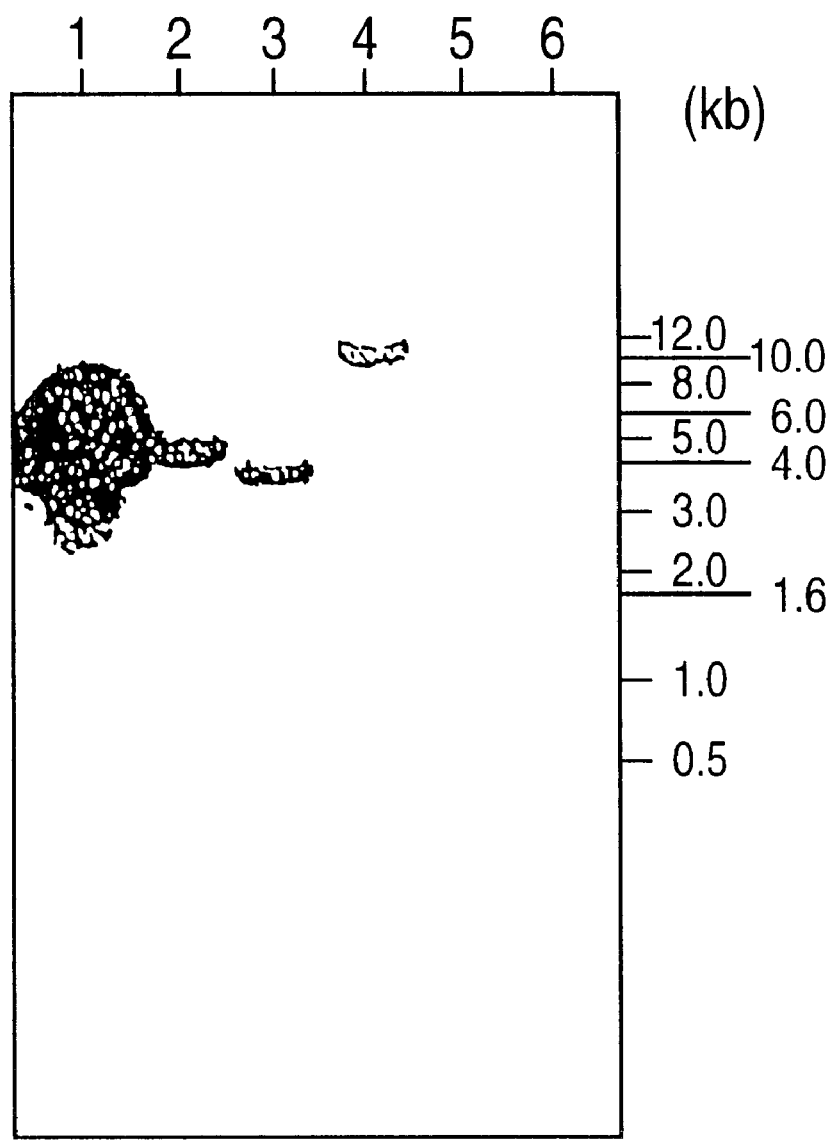
FIG. 21 is a diagram showing the results of Southern hybridization which indicate the detection of genes regulating aureobasidin sensitivity of *A. niger* and *A. oryzae*.

Confirmation of genes regulating aureobasidin sensitivity carried by A. niger and A. oryzae Genomic DNAs were extracted and purified from strains A. fumigatus TIMM1776, A. niger FGSC805 and A. oryzae IF05710 in accordance with the method described in Example 15-b). Further, genomic DNAs were extracted and purified from yeast strains *S. cerevisiae* DKD-5D and *Schizo. pombe* JY745 in accordance with the method of P. Philippsen et al. [*Methods in Enzymology,* 194, 169–175 (1991)]. 5 µg portions of the genomic DNAs of *A. nidulans, A. fumigatus, A. niger, A. oryzae, S. cerevisiae* and *Schizo. pombe* were cleaved with a restriction enzyme PstI, separated by electrophoresing on a 0.8% agarose gel, transferred onto a nylon membrane and fixed. Next, Southern hybridization was efected by using a PstI-EcoRI fragment of the cDNA of the anaur1 gene labeled with [α-$^{32}$p]dCTP as a probe. The hybridization was effected under the same conditions as those described in Example 16-a). FIG. 21 shows the autoradiogram of the hybridization. As FIG. 21 clearly shows, genes regulating aureobasidin sensitivity occur in *A. niger* and *A. oryzae* too. It has been also revealed that the DNA of *A. nidulans* is not hybridizable with the aureobasidin sensitive genes of the yeasts *S. cerevisiae* and *Schizo. pombe*. In FIG. 21, the lanes 1, 2, 3, 4, 5 and 6 show the results of the Southern hybridization of the genomic DNAs of *A. nidulans, A. fumigatus, A. niger, A. oryzae, S. cerevisiae* and *Schizo. pombe* respectively.

According to the present invention, a novel protein regulating aureobasidin sensitivity and a gene coding for the protein, i.e., a gene regulating aureobasidin sensitivity are provided. These substances are useful in the diagnosis and treatment for diseases caused by organisms having the above-mentioned gene, such as mycoses. The present invention further provides an antisense DNA and an antisense RNA of this gene, a nucleic acid probe being hybridizable with the gene, a process for detecting the gene by using this nucleic acid probe, a process for producing a protein regulating aureobasidin sensitivity by using a transformant having the gene introduced thereinto, an antibody for the protein and a process for detecting the protein by using this antibody. They are also useful in the diagnosis and treatment of diseases including mycoses.

In addition, the present invention provides a chromosome integration vector with the use of a resistance to aureobasidin as a selective marker, which is useful in genetic recombination of fungi (in particular, industrial fungi), a process for producing a transformant having this vector introduced thereinto, and a transformant obtained by this process. They are effectively applicable to, for example the creation of a transformant for producing a useful protein and breeding. The present invention also provides a protein capable of imparting a strong resistance to aureobasidin and a DNA coding for this protein. They imparted a resistance to an organism having an aureobasidin sensitivity and are useful as a selective marker for screening the organism thus acquiring the resistance. They are highly useful particularly in, for example, the genetic engineering breeding of a practically usable yeast and the analysis of genetic information of *C. albicans*. In particular, an aureobasidin resistant gene originating in *S. cerevisiae* is highly useful in the breeding of *S. cerevisiae* and the preparation of a transformant for producing a useful protein, because *S. cerevisiae* is a yeast which is not only widely employed as an industrial yeast but also highly safe in genetic recombination.

Both the aureobasidin-resistant genes obtained from yeasts and that from mold are isolated from the resistant mutant derived from yeasts and mold, respectively. And the aureobasidin-resistant gene of mold have function, giving an aureobasidin-resistance, identical to the genes of yeasts. That is, these genes are functional homologs. Although amino acid sequence of aureobasidin-resistant genes of yeasts have low homology with those of molds (for example, 35% in the comparison of that of spaur1 and that of anaur1), middle regions of these amino acid sequences have high homology (57% in the comparison of the region between 24th and 329th of spaur1 and the region between 59th and 364th of anaur1). Furthermore, a secondary structure predicted from amino acid sequence of these genes have identical characteristic which is membrane protein containing transmembrane domains. Therefore, these proteins are homologous in structure also.

What is claimed is:

1. An isolated DNA comprising a nucleic acid sequence which encodes the amino acid sequence of SEQ ID No. 2, 4, or 5.

2. An isolated DNA comprising the nucleic acid sequence of SEQ ID No. 1, 3, or 12.

3. The DNA according to claim 1, which is isolated from mold.

4. The DNA according to claim 2, which is isolated from mold.

5. The DNA according to claim 1, which is isolated from an microorganism belonging to the genus Aspergillus.

6. The DNA according to claim 2, which is isolated from a microorganism belonging to the genus Aspergillus.

7. An isolated DNA comprising a nucleic acid sequence which encodes a portion of the amino acid sequence of SEQ ID No. 2 and which portion confers upon a cell resistance to aureobasidin.

8. An isolated DNA comprising a fragment of the nucleic acid sequence of SEQ ID No. 1 and which fragment encodes a protein which confers upon a cell resistance to aureobasidin.

9. An isolated DNA comprising a nucleic acid sequence which encodes the amino acid sequence of SEQ ID No. 2 or containing one conservative substitution thereof and which amino acid sequence confers upon a cell resistance to aureobasidin.

10. An isolated DNA comprising the nucleic acid sequence of SEQ ID No. 1 or containing one mutation thereof and which encodes a protein which confers upon a cell resistance to aureobasidin.

11. An isolated DNA which is hybridizable with the DNA according to claim 1, 2, 7, 8, 9, or 10 or its full complement under conditions of 6×SSC, 1% of sodium lauryl sulfate, 100 µg/ml of salmon sperm DNA and 5×Denhardt's solution at 65° C. for 20 hours and which encodes a protein which confers upon a cell sensitivity or resistance to aureobasidin.

12. An isolated DNA, which comprises a DNA having a sequence which is fully complementary to the DNA according to claim 1, 2, 7, 8, 9, 10, or 11.

13. The isolated DNA according to claim 12, which has the nucleic acid sequence according to SEQ ID No. 13.

14. An isolated RNA, which comprises an RNA having a sequence which is fully complementary to the mRNA encoded by the DNA according to claim 1, 2, 7, 8, 9, 10, or 11.

15. The isolated RNA according to claim 14, which has the nucleic acid sequence according to SEQ ID No. 14, or a fragment of 15 or more bases thereof.

16. A recombinant plasmid comprising a nucleic acid sequence containing the DNA according to claim 1, 2, 7, 8, 9, 10, or 11.

17. A transformant containing the recombinant plasmid according to claim 16.

18. A process for producing a protein, which comprises:
    incubating the transformant according to claim 17 under conditions to express the protein, and
    recovering the protein from the culture medium.

19. An isolated DNA comprising a nucleic acid sequence which encodes a protein which has an amino acid sequence according to SEQ ID No. 4 except that the 275th amino acid residue Gly in the amino acid sequence is replaced by another amino acid residue, and which confers upon a cell resistance to aureobasidin.

20. A chromosome integration vector for a host fungus or mold, which comprises a nucleic acid sequence containing the DNA according to claim 1, 2, 7, 8, 9, 10, 11, or 19.

21. A process for producing an aureobasidin resistant transformant, which comprises:
    (a) providing a replication vector which contains a DNA according to claim 1, 2, 7, 8, 9, 10, 11 or 19 and which encodes a protein imparting aureobasidin resistance,
    (b) cleaving the DNA in the replication vector at one site to produce a chromosome integration vector for a host fungus or mold;
    (c) integrating the chromosome integration vector into the chromosome of the host; and (d) selecting a host which has been transformed into an aureobasidin resistant transformant in the presence of aureobasidin.

22. A transformant obtained by the process according to claim 21.

23. An isolated DNA comprising a nucleic acid sequence which encodes a portion of the amino acid sequence of SEQ ID No. 4 or 5 and which portion confers upon a cell sensitivity to aureobasidin.

24. An isolated DNA comprising a fragment of the nucleic acid sequence of SEQ ID No. 3 or 12 and which fragment encodes a protein which confers upon a cell sensitivity to aureobasidin.

25. An isolated DNA comprising a nucleic acid sequence which encodes the amino acid sequence of SEQ ID No. 4 or 5 or containing one conservative substitution thereof and which amino acid sequence confers upon a cell sensitivity to aureobasidin.

26. An isolated DNA comprising the nucleic acid sequence of SEQ ID No. 3 or 12 or containing one mutation thereof and which encodes a protein which confers upon a cell sensitivity to aureobasidin.

27. An isolated DNA which is hybridizable with the DNA according to claim 23, 24, 25, or 26 or its full complement under conditions of 6×SSC, 1% of sodium lauryl sulfate, 100 μg/ml of salmon sperm DNA and 5×Denhardt's solution at 65° C. for 20 hours and which encodes a protein which confers upon a cell sensitivity or resistance to aureobasidin.

28. An isolated DNA, which comprises a DNA having a sequence which is fully complementary to the DNA according to claim 23, 24, 25, 26 or 27.

29. An isolated RNA, which comprises an RNA having a sequence which is fully complementary to the mRNA encoded by the DNA according to claim 23, 24, 25, 26, or 27.

30. A recombinant plasmid comprising a nucleic acid sequence containing the DNA according to claim 23, 24, 25, 26, or 27.

31. A transformant containing the recombinant plasmid according to claim 30.

32. A process for producing a protein, which comprises:

incubating the transformant according to claim 31 under conditions to express the protein, and recovering the protein from the culture medium.

* * * * *

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 4140 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO:1:

```
AGATCTGTGG CTTCCGGTTG GCTACTTGTA ACCAACTGAT GGTCAGATGG ATCTGCCGTC      60

TGTTTTGATT TGAATTTTCC CTGCTCATTC TGATTCTGTG AGAGGCTGCA TTCATTATCA     120

CATCTCATAC CCGGCGCCTG CGACTTCGGT CACCTCTGCG GTCTGGCGGT TACCGGGGTC     180

CGTCTGAGAC TCGTCAGTCA GCCATTCGAG TATGCGAACT CTGACTTTGC TCACCTAAGA     240

GTTTGCACGA GATGCCGAAA TCCTCCTCGA GTAGAGTTTG CAAGGCTTGA ACCTTGGTCC     300
```

-continued

```
TTGAAGCCCG AAAGTGGCTC AGTAGTGGGA TCGATAGTCT GGTTGTTGAA GATTTTCTCC      360

TCCACCTTAC CTATGGCCGC TGGCCTTCTC CACCTTTCAG GCTTTCAGGC ACCCTCGGCT      420

CGGATTCTGT ATCGTCCGGT ACCGAAGCTA GTCCTAGCTA GTCAAAGCTA GTCCAAGCTA      480

GTCTCGTCAA GGTTTGGCGC AGCGCGGTTC CGTGTAAAGT ACAAATTTGA AATACGAATA      540

CGCAGTACTC GCAGCCGGCA CTTCCGCTCA GCCCAGGCTC AGAGGCTAAG GGTGTTGGCG      600

CTTCCTCATC ATCTTCTTCT CGTCGACCTT TTCCTCTTTC TCTCCCTATC GGTGCTTCTC      660

TCCAACCTCA TTCTCAGTCG TTCGCCCATC AGGTTTATAC TCCGGCTCCG TGGCCATCTG      720

CCTCCCTCAC GACCTCCTCG TTCCAGGTTT TCCTCTCGAC TGCTGCGCCC TTGCACTTCG      780

CCTTGCATCA GTGAAACCCC CTGCAACGTG ACGGCTCAAA GACATCCTCG TTTGGCCGCT      840

GGAGACCGGA GCGTGCGCTT CGTTTCGTCT TCTTCGAACC GATCTCAATT TCCCCGCTCG      900

GGTTGACGCC GTCAGCACCC TGCTCGTTGC CTAACGGCTT GTTATTCAAG ACCCCTTTTC      960

TGCCGCTTCC GCGACCGATT TATTCGTCGC CTTCCAACTC TTGTACAATC GGGGGGAAAG     1020

AAAGCAGACG GAGTTCGATC TGGAGGAATT ATAGCTGAGT CTTGCCCGCA AGACTCGCCG     1080

CAACCATGAA TCAAACACTT CCCACGTGGA AGGACCGCAC GCAGAACCAG TTTGGAAAGC     1140

TTCAGATCCA GGTTCCATGG CGGTCCATCC AACTGCTCGT CCCGCATCGC ATGCGGCGGA     1200

AGTTAAGGTC CAAATTGCGC AGTAGAGCGT CTCCTACCTC GTCAATAGCC TCTTTACAGA     1260

CGTCGTTATC GCCTGCAGAC ACACTACGAT CGCTCCAAAG CCACCGATGG ACGGTTTACG     1320

ACTTCCAATA TCTGCTTCTG TTGATCGTGG GCATCTTCTC TTTGACCGTT ATCGAGTCGC     1380

CCGGGCCTTT GGGCAAAACG GCCATTTTCT CCATGCTCCT ATTCTCTCTC CTGATCCCTA     1440

TGACCCGCCA GTTCTTCCTC CCGTTTCTGC CGATTGCCGG ATGGCTTCTG TTTTTCTACG     1500

CCTGCCAGTG AGTTAAAAAC AACCCGCTAC CAGACCCCGT GCAGCAGTTA CTCACATATG     1560

CAGGTTCATC CCAAGCGATT GGCGCCCTGC GATTTGGGTT CGTGTCTTGC CTGCACTGGA     1620

GAATATTCTC TACGGCGCAA ACATCAGCAA CATCCTATCC GCTCACCAGA ACGTTGTGCT     1680

TGACGTGCTG GCGTGGCTAC CCTACGGTAT CTGCCACTAT GGCGCTCCGT TTGTGTGCTC     1740

GTTGATCATG TTCATCTTCG GTCCGCCCGG CACTGTTCCC CTTTTCGCGC GCACTTTCGG     1800

CTATATCAGT ATGACTGCGG TTACTATTCA GCTGTTTTTC CCTTGCTCTC CACCTTGGTA     1860

TGAGAATCGC TATGGTCTAG CTCCGGCAGA CTACTCCATC CAAGGTGATC CCGCAGGGCT     1920

TGCCCGCATT GACAAGCTTT TCGGCATCGA CCTTTACACG TCTGTTTTCC ATCAGTCGCC     1980

TGTTGTGTTC GGCGCTTTTC CGTCGCTGCA TGCTGCCGAC TCAACCCTGG CCGCACTTTT     2040

CATGAGTCAT GTTTTCCCCC GCATGAAGCC CGTCTTCGTG ACCTATACTC TATGGATGTG     2100

GTGGGCAACA ATGTACCTCT CACATCACTA TGCGGTCGAT TTGGTTGCGG GTGGTCTCCT     2160

GGCCGCCATT GCTTTCTACT TCGCCAAGAC CCGATTCCTT CCCCGTGTCC AGCTCGACAA     2220

GACCTTCCGT TGGGACTACG ACTATGTGGA ATTCGGCGAG TCTGCCCTGG AGTATGGGTA     2280

TGGTGCAGCT GGCTATGATG GAGACTTCAA CTCTGACAGC GATGAATGGA CTGTTGGTTC     2340

TTCATCCTCC GTCTCCTCAG GCTCCTTGAG TCCCGTTGAC GATCATTACT CATGGGAAAC     2400

CGAGGCACTG ACCTCCCCAC ATACTGATAT TGAGTCCGGC AGGCATACTT TCAGCCCTTG     2460

AGTAGCCACA AACCAAACTC GATACCTGCA TATAGCGATC TCGCTCCTCC TCCACTGCAT     2520

CTATTTACGA GACGGCGTTA GAACATTTCA CGACATTCTG GCTTTATTGC ATCGAGCACA     2580

TTTCGACACA TATATCTTTA ATACCCTTTC TTCGGTGTCC CAGATCATCG GTTCGACCTT     2640
```

```
AATGTACCTC GGTCCGAATC CGCCTGGGAT ACTGTTTCTC TTTCCGCCGC ACTTCACTGT    2700

ACATTGCTTG ACATTGCGAA ACCGGGTTGG GCTCGAACGT GGGATGGGTT ATCGCTCATC    2760

GCTACACGCC GTTGCTCCAT CATAATGTTA ATGGACACAA TGGGGCTACG CATCCTGGTG    2820

TTTAGTCCTG GAAGACCATC CGATAACCCC CGTCGGTAAC ACTCGCTTGT CTCGTGTCCA    2880

CCCAGACACT ACTTCAATTC TCACTTCTAT CGTCCGCTAT TACCTTGACC TGGTCGAACC    2940

CATCCTTATT ATTCGTTTCG ACTATGCTAT ATATTTATTT TTACCATTCG TGTCGATCGC    3000

TCATACTCTT GGCGCTTGGG ACTGGAAGCA TTTATATTGG AAAAAATCAC GGAATGGGGC    3060

GCCTTTTCTT CTTGCACTTC ACTCGCTGTG CATAGACGGT TTTACATTTC TGCTTTGCAA    3120

TGCATCACGA ACTCTGCATT AGCATATAGA AAGAGGGGAA GGATGGACCT TCTTCTTGAT    3180

TGCTCGCATG GTTTATCCAT TCGCTCAAAG TGGATTACGT CCACATATTA CCCGGGGGCT    3240

ATACACATGG CTACTGTGTT GCTTTCTGAC ATTCGCCGGA CGTGCAAGGT TGGGAGGAGA    3300

GTCTGACGCT GACGGGGCTT GTTGAAGGAT GTTCACGCGT CCCGATTTGA CCCGGCTTCG    3360

ACTAACCTCA GATTCTCGAC TTGTTGGACG GTGACTTGAC TTGCTTGCTA TGGTCTGACG    3420

CTCTCACACC TACCTATCAC ATCCTCCTCA CCTCACAAAT TCCGCTCATG GACACTATCC    3480

TCTTCTTTTC GTTTCCCTTG GATAGTGTGT GTGTGTGTGT GGTTGGGGCA AATTATCCAT    3540

AGCAGCAGTA TTATTAGTTA TAATCCGGTA GTGTTATGAT TTATGAAGGC AACTTGTATA    3600

CTATTGCCAC TTTGTCCATA TCTCTTGCTT GTAATAGAAC TGACATCGCG ACGCTTCGGC    3660

CACGATGCAT ATAAAAACTC TAGTCAACAC GATATTAACA AGCGAAACCA TTACGCTGTA    3720

AACTATTCAG GATCGCCGCG GGCCCATCTG GGACTTGACT GTACTAAATA TGTCCTAAAG    3780

CAAGCAGACT AAATATTTAA CGTGGGATAT TATTCATATA CGCATATGTA TACATAGTCA    3840

TAACAAGCCA AGGGGTGGGT AGGGGTGGGT AATTATTATT TTTTTTCGTC GATACAAGTA    3900

TCCATCCTTA AATGTCCGTG GTCTACTCTT CATAAATCTT AACCCGCTCC GCATACTCCT    3960

TTATCCTCGA GACAAAAGTG TCTTCAATTT CATCGCCACG GCCACCAGCA ACGCGGAGGA    4020

TAAGGTCGTT GAGAGAGGCG CGGCCGAGAA TGTCGACATG GTCGCCTTCA TATTGTTAGC    4080

ATGCGACGTC AGACTGGAAC CAGGAAGGGA AAGGAGAGAG GTACCTGTAT TTGGACCACC    4140
```

(2) INFORMATION FOR SEQ ID NO:2:

(i) SEQUENCE CHARACTERISTICS:
        (A) LENGTH: 439 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Asn Gln Thr Leu Pro Thr Trp Lys Asp Arg Thr Gln Asn Gln
 1               5                  10                  15

Phe Gly Lys Leu Gln Ile Gln Val Pro Trp Arg Ser Ile Gln Leu
                20                  25                  30

Leu Val Pro His Arg Met Arg Arg Lys Leu Arg Ser Lys Leu Arg
                35                  40                  45

Ser Arg Ala Ser Pro Thr Ser Ser Ile Ala Ser Leu Gln Thr Ser
                50                  55                  60

Leu Ser Pro Ala Asp Thr Leu Arg Ser Leu Gln Ser His Arg Trp
                65                  70                  75

Thr Val Tyr Asp Phe Gln Tyr Leu Leu Leu Leu Ile Val Gly Ile
```

```
                80              85              90
Phe Ser Leu Thr Val Ile Glu Ser Pro Gly Pro Leu Gly Lys Thr
                95             100             105
Ala Ile Phe Ser Met Leu Leu Phe Ser Leu Leu Ile Pro Met Thr
               110             115             120
Arg Gln Phe Phe Leu Pro Phe Leu Pro Ile Ala Gly Trp Leu Leu
               125             130             135
Phe Phe Tyr Ala Cys Gln Phe Ile Pro Ser Asp Trp Arg Pro Ala
               140             145             150
Ile Trp Val Arg Val Leu Pro Ala Leu Glu Asn Ile Leu Tyr Gly
               155             160             165
Ala Asn Ile Ser Asn Ile Leu Ser Ala His Gln Asn Val Val Leu
               170             175             180
Asp Val Leu Ala Trp Leu Pro Tyr Gly Ile Cys His Tyr Gly Ala
               185             190             195
Pro Phe Val Cys Ser Leu Ile Met Phe Ile Phe Gly Pro Pro Gly
               200             205             210
Thr Val Pro Leu Phe Ala Arg Thr Phe Gly Tyr Ile Ser Met Thr
               215             220             225
Ala Val Thr Ile Gln Leu Phe Phe Pro Cys Ser Pro Pro Trp Tyr
               230             235             240
Glu Asn Arg Tyr Gly Leu Ala Pro Ala Asp Tyr Ser Ile Gln Gly
               245             250             255
Asp Pro Ala Gly Leu Ala Arg Ile Asp Lys Leu Phe Gly Ile Asp
               260             265             270
Leu Tyr Thr Ser Val Phe His Gln Ser Pro Val Val Phe Gly Ala
               275             280             285
Phe Pro Ser Leu His Ala Ala Asp Ser Thr Leu Ala Ala Leu Phe
               290             295             300
Met Ser His Val Phe Pro Arg Met Lys Pro Val Phe Val Thr Tyr
               305             310             315
Thr Leu Trp Met Trp Trp Ala Thr Met Tyr Leu Ser His His Tyr
               320             325             330
Ala Val Asp Leu Val Ala Gly Gly Leu Leu Ala Ala Ile Ala Phe
               335             340             345
Tyr Phe Ala Lys Thr Arg Phe Leu Pro Arg Val Gln Leu Asp Lys
               350             355             360
Thr Phe Arg Trp Asp Tyr Asp Tyr Val Glu Phe Gly Glu Ser Ala
               365             370             375
Leu Glu Tyr Gly Tyr Gly Ala Ala Gly Tyr Asp Gly Asp Phe Asn
               380             385             390
Leu Asp Ser Asp Glu Trp Thr Val Gly Ser Ser Ser Val Ser
               395             400             405
Ser Gly Ser Leu Ser Pro Val Asp Asp His Tyr Ser Trp Glu Thr
               410             415             420
Glu Ala Leu Thr Ser Pro His Thr Asp Ile Glu Ser Gly Arg His
               425             430             435
Thr Phe Ser Pro (2) INFORMATION FOR SEQ ID NO:3:

(i) SEQUENCE CHARACTERISTICS:
        (A) LENGTH:  2856 base pairs
        (B) TYPE:  nucleic acid
```

(C) STRANDEDNESS: double
(D) TOPOLOGY: linear (ii) MOLECULE TYPE: cDNA (xi) SEQUENCE DESCRIPTION: SEQ ID NO:3:

```
GGTTTATACT CCGGCTCCGT GGCCATCTGC CTCCCTCACG ACCTCCTCGT TCCAGGTTTT      60
CCTCTCGACT GCTGCGCCCT TGCACTTCGC CTTGCATCAG TGAAACCCCC TGCAACGTGA     120
CGGCTCAAAG ACATCCTCGT TTGGCCGCTG GAGACCGGAG CGTGCGCTTC GTTTCGTCTT     180
CTTCGAACCG ATCTCAATTT CCCCGCTCGG GTTGACGCCG TCAGCACCCT GCTCGTTGCC     240
TAACGGCTTG TTATTCAAGA CCCCTTTTCT GCCGCTTCCG CGACCGATTT ATTCGTCGCC     300
TTCCAACTCT TGTACAATCG GGGGAAAGA AAGCAGACGA AGTTCGATCT GGAGGAATTA     360
TAGCTGAGTC TTGCCCGCAA GACTCGCCGC AACCATGAAT CAAACACTTC CCACGTGGAA     420
GGACCGCACG CAGAACCAGT TTGGAAAGCT TCAGATCCAG GTTCCATGGC GGTCCATCCA     480
ACTGCTCGTC CCGCATCGCA TGCGGCGGAA GTTAAGGTCC AAATTGCGCA GTAGAGCGTC     540
TCCTACCTCG TCAATAGCCT CTTTACAGAC GTCGTTATCG CCTGCAGACA CACTACGATC     600
GCTCCAAAGC CACCGATGGA CGGTTTACGA CTTCCAATAT CTGCTTCTGT TGATCGTGGG     660
CATCTTCTCT TTGACCGTTA TCGAGTCGCC CGGGCCTTTG GGCAAAACGG CCATTTTCTC     720
CATGCTCCTA TTCTCTCTCC TGATCCCTAT GACCCGCCAG TTCTTCCTCC CGTTTCTGCC     780
GATTGCCGGA TGGCTTCTGT TTTTCTACGC CTGCCAGTTC ATCCCAAGCG ATTGGCGCCC     840
TGCGATTTGG GTTCGTGTCT TGCCTGCACT GGAGAATATT CTCTACGGCG CAAACATCAG     900
CAACATCCTA TCCGCTCACC AGAACGTTGT GCTTGACGTG CTGGCGTGGC TACCCTACGG     960
TATCTGCCAC TATGGCGCTC CGTTTGTGTG CTCGTTGATC ATGTTCATCT TCGGTCCGCC    1020
CGGCACTGTT CCCCTTTTCG CGCGCACTTT CGGCTATATC AGTATGACTG CGGTTACTAT    1080
TCAGCTGTTT TTCCCTTGCT CTCCACCTTG GTATGAGAAT CGCTATGGTC TAGCTCCGGC    1140
AGACTACTCC ATCCAAGGTG ATCCCGCAGG GCTTGCCCGC ATTGACAAGC TTTTCGGCAT    1200
CGACCTTTAC ACGTCTGTTT CCATCAGTC GCCTGTTGTG TTCGGCGCTT TCCGTCGCT    1260
GCATGCTGCC GACTCAACCC TGGCCGCACT TTTCATGAGT CATGTTTTCC CCGCATGAA    1320
GCCCGTCTTC GTGACCTATA CTCTATGGAT GTGGTGGGCA ACAATGTACC TCTCACATCA    1380
CTATGCGGTC GATTTGGTTG CGGGTGGTCT CCTGGCCGCC ATTGCTTTCT ACTTCGCCAA    1440
GACCCGATTC CTTCCCCGTG TCCAGCTCGA CAAGACCTTC CGTTGGGACT ACGACTATGT    1500
GGAATTCGGC GAGTCTGCCC TGGAGTATGG GTATGGTGCA GCTGGCTATG ATGGAGACTT    1560
CAATCTCGAC AGCGATGAAT GGACTGTTGG TTCTTCATCC TCCGTCTCCT CAGGCTCCTT    1620
GAGTCCCGTT GACGATCATT ACTCATGGGA AACCGAGGCA CTGACCTCCC ACATACTGA    1680
TATTGAGTCC GGCAGGCATA CTTTCAGCCC TTGAGTAGCA ACAAACCAAA CTCGATACCT    1740
GCATATAGCG ATCTCGCTCC TCCTCCACTG CATCTATTTA CGAGACGGCG TTAGAACATT    1800
TCACGACATT CTGGCTTTAT TGCATCGAGC ACATTTCGAC ACATATATCT TTAATACCCT    1860
TTCTTCGGTG TCCCAGATCA TCGGTTCGAC CTTAATGTAC CTCGGTCCGA ATCCGCCTGG    1920
GATACTGTTT CTCTTTCCGC CGCACTTCAC TGTACATTGC TTGACATTGC GAAACCGGGT    1980
TGGGCTCGAA CGTGGGATGG GTTATCGCTC ATCGCTACAC GCCGTTGCTC CATCATAATG    2040
TTAATGGACA CAATGGGGCT ACGCATCCTG GTGTTTAGTC CTGGAAGACC ATCCGATAAC    2100
CCCCGTCGGT AACACTCGCT TGTCTCGTGT CCACCCAGAC ACTACTTCAA TTCTCACTTC    2160
```

```
TATCGTCCGC TATTACCTTG ACCTGGTCGA ACCCATCCTT ATTATTCGTT TCGACTATGC    2220

TATATATTTA TTTTTACCAT TCGTGTCGAT CGCTCATACT CTTGGCGCTT GGGACTGGAA    2280

GCATTTATAT TGGAAAAAAT CACGGAATGG GGCGCCTTTT CTTCTTGCAC TTCACTCGCT    2340

GTGCATAGAC GGTTTTACAT TTCTGCTTTG CAATGCATCA CGAACTCTGC ATTAGCATAT    2400

AGAAAGAGGG GAAGGATGGA CCTTCTTCTT GATTGCTCGC ATGGTTTATC CATTCGCTCA    2460

AAGTGGATTA CGTCCACATA TTACCCGGGG GCTATACACA TGGCTACTGT GTTGCTTTCT    2520

GACATTCGCC GGACGTGCAA GGTTGGGAGG AGAGTCTGAC GCTGACGGGG CTTGTTGAAG    2580

GATGTTCACG CGTCCCGATT TGACCCGGCT TCGACTAACC TCAGATTCTC GACTTGTTGG    2640

ACGGTGACTT GACTTGCTTG CTATGGTCTG ACGCTCTCAC ACCTACCTAT CACATCCTCC    2700

TCACCTCACA AATTCCGCTC ATGGACACTA TCCTCTTCTT TTCGTTTCCC TTGGATAGTG    2760

TGTGTGTGTG TGTGGTTGGG GCAAATTATC CATAGCAGCA GTATTATTAG TTATAATCCG    2820

GTAGTGTTAT GATTATGAA GGCAACTTGT ATACTA                               2856
```

(2) INFORMATION FOR SEQ ID NO:4:

(i) SEQUENCE CHARACTERISTICS:
        (A) LENGTH: 439 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Asn Gln Thr Leu Pro Thr Trp Lys Asp Arg Thr Gln Asn Gln
 1               5                  10                  15

Phe Gly Lys Leu Gln Ile Gln Val Pro Trp Arg Ser Ile Gln Leu
                20                  25                  30

Leu Val Pro His Arg Met Arg Arg Lys Leu Arg Ser Lys Leu Arg
                35                  40                  45

Ser Arg Ala Ser Pro Thr Ser Ser Ile Ala Ser Leu Gln Thr Ser
                50                  55                  60

Leu Ser Pro Ala Asp Thr Leu Arg Ser Leu Gln Ser His Arg Trp
                65                  70                  75

Thr Val Tyr Asp Phe Gln Tyr Leu Leu Leu Ile Val Gly Ile
                80                  85                  90

Phe Ser Leu Thr Val Ile Glu Ser Pro Gly Pro Leu Gly Lys Thr
                95                  100                 105

Ala Ile Phe Ser Met Leu Leu Phe Ser Leu Leu Ile Pro Met Thr
                110                 115                 120

Arg Gln Phe Phe Leu Pro Phe Leu Pro Ile Ala Gly Trp Leu Leu
                125                 130                 135

Phe Phe Tyr Ala Cys Gln Phe Ile Pro Ser Asp Trp Arg Pro Ala
                140                 145                 150

Ile Trp Val Arg Val Leu Pro Ala Leu Glu Asn Ile Leu Tyr Gly
                155                 160                 165

Ala Asn Ile Ser Asn Ile Leu Ser Ala His Gln Asn Val Val Leu
                170                 175                 180

Asp Val Leu Ala Trp Leu Pro Tyr Gly Ile Cys His Tyr Gly Ala
                185                 190                 195

Pro Phe Val Cys Ser Leu Ile Met Phe Ile Phe Gly Pro Pro Gly
                200                 205                 210
```

```
Thr Val Pro Leu Phe Ala Arg Thr Phe Gly Tyr Ile Ser Met Thr
            215                 220                 225

Ala Val Thr Ile Gln Leu Phe Phe Pro Cys Ser Pro Pro Trp Tyr
            230                 235                 240

Glu Asn Arg Tyr Gly Leu Ala Pro Ala Asp Tyr Ser Ile Gln Gly
            245                 250                 255

Asp Pro Ala Gly Leu Ala Arg Ile Asp Lys Leu Phe Gly Ile Asp
            260                 265                 270

Leu Tyr Thr Ser Gly Phe His Gln Ser Pro Val Val Phe Gly Ala
            275                 280                 285

Phe Pro Ser Leu His Ala Ala Asp Ser Thr Leu Ala Ala Leu Phe
            290                 295                 300

Met Ser His Val Phe Pro Arg Met Lys Pro Val Phe Val Thr Tyr
            305                 310                 315

Thr Leu Trp Met Trp Ala Thr Met Tyr Leu Ser His His Tyr
            320                 325                 330

Ala Val Asp Leu Val Ala Gly Gly Leu Leu Ala Ala Ile Ala Phe
            335                 340                 345

Tyr Phe Ala Lys Thr Arg Phe Leu Pro Arg Val Gln Leu Asp Lys
            350                 355                 360

Thr Phe Arg Trp Asp Tyr Asp Tyr Val Glu Phe Gly Glu Ser Ala
            365                 370                 375

Leu Glu Tyr Gly Tyr Gly Ala Ala Gly Tyr Asp Gly Asp Phe Asn
            380                 385                 390

Leu Asp Ser Asp Glu Trp Thr Val Gly Ser Ser Ser Val Ser
            395                 400                 405

Ser Gly Ser Leu Ser Pro Val Asp Asp His Tyr Ser Trp Glu Thr
            410                 415                 420

Glu Ala Leu Thr Ser Pro His Thr Asp Ile Glu Ser Gly Arg His
            425                 430                 435

Thr Phe Ser Pro (2) INFORMATION FOR SEQ ID NO:5:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Met Asn Thr Thr Leu Pro Ser Trp Lys Asp Arg Thr Gln Asn Gln
 1               5                  10                  15

Phe Gly Lys Leu Gln Ile Gln Val Pro Trp Arg Thr Ile Gln Leu
                20                  25                  30

Leu Val Pro His Arg Met Arg Arg Lys Ile Arg Ser Lys Leu Arg
                35                  40                  45

Ser Arg Ile Ser Pro Thr Ser Ser Ile Ser Ser Leu Gln Thr Ser
                50                  55                  60

Phe Ser Pro Val Asp Thr Leu Arg Ser Leu Gln Ser His Arg Trp
                65                  70                  75

Thr Leu Tyr Asp Phe Gln Tyr Leu Leu Leu Leu Ile Val Gly Ile
                80                  85                  90

Phe Ser Leu Ser Val Met Glu Ser Pro Gly Pro Leu Ala Lys Thr
```

-continued

|  | 95 |  |  |  | 100 |  |  |  | 105 |  |
|---|---|---|---|---|---|---|---|---|---|---|

Ala Ala Phe Thr Leu Leu Val Ser Leu Leu Pro Ile Thr
            110                 115                 120

Arg Gln Phe Phe Leu Pro Phe Leu Pro Ile Ala Gly Trp Leu Ile
            125                 130                 135

Phe Phe Tyr Ala Cys Gln Phe Ile Pro Ser Asp Trp Arg Pro Ala
            140                 145                 150

Ile Trp Val Arg Val Leu Pro Ala Leu Glu Asn Ile Leu Tyr Gly
            155                 160                 165

Ala Asn Ile Ser Asn Ile Leu Ser Ala His Gln Asn Val Val Leu
            170                 175                 180

Asp Val Leu Ala Trp Leu Pro Tyr Gly Ile Cys His Tyr Gly Ala
            185                 190                 195

Pro Phe Val Cys Ser Ala Ile Met Phe Ile Phe Gly Pro Pro Gly
            200                 205                 210

Thr Val Pro Leu Phe Ala Arg Thr Phe Gly Tyr Ile Ser Met Ala
            215                 220                 225

Ala Val Thr Ile Gln Leu Phe Phe Pro Cys Ser Pro Pro Trp Tyr
            230                 235                 240

Glu Asn Leu Tyr Gly Leu Ala Pro Ala Asp Tyr Ser Met Pro Gly
            245                 250                 255

Asn Pro Ala Gly Leu Ala Arg Ile Asp Glu Leu Phe Gly Ile Asp
            260                 265                 270

Leu Tyr Thr Ser Gly Phe Arg Gln Ser Pro Val Val Phe Gly Ala
            275                 280                 285

Phe Pro Ser Leu His Ala Ala Asp Ser Thr Leu Ala Ala Leu Phe
            290                 295                 300

Met Ser Gln Val Phe Pro Arg Leu Lys Pro Leu Phe Val Ile Tyr
            305                 310                 315

Thr Leu Trp Met Trp Trp Ala Thr Met Tyr Leu Ser His His Tyr
            320                 325                 330

Ala Val Asp Leu Val Gly Gly Gly Leu Leu Ala Thr Val Ala Phe
            335                 340                 345

Tyr Phe Ala Lys Thr Arg Phe Met Pro Arg Val Gln Asn Asp Lys
            350                 355                 360

Met Phe Arg Trp Asp Tyr Asp Tyr Val Glu Tyr Gly Asp Ser Ala
            365                 370                 375

Leu Asp Tyr Gly Tyr Gly Pro Ala Ser Phe Glu Gly Glu Phe Asn
            380                 385                 390

Leu Asp Ser Asp Glu Trp Thr Val Gly Ser Ser Ser Ser Ile Ser
            395                 400                 405

Ser Gly Ser Leu Ser Pro Val Asp Asp His Tyr Ser Trp Glu Gly
            410                 415                 420

Glu Thr Leu Ala Ser Pro Ala Thr Asp Ile Glu Ser Gly Arg His
            425                 430                 435

Phe (2) INFORMATION FOR SEQ ID NO:6:

(i) SEQUENCE CHARACTERISTICS:
        (A) LENGTH:  401 amino acids
        (B) TYPE:  amino acid
        (C) STRANDEDNESS:  single
        (D) TOPOLOGY:  linear (ii) MOLECULE TYPE: peptide (xi) SEQUENCE DESCRIPTION: SEQ ID NO:6:

```
Met Ala Asn Pro Phe Ser Arg Trp Phe Leu Ser Glu Arg Pro
  1               5                  10                  15
Asn Cys His Val Ala Asp Leu Glu Thr Ser Leu Asp Pro His Gln
               20                  25                  30
Thr Leu Leu Lys Val Gln Lys Tyr Lys Pro Ala Leu Ser Asp Trp
               35                  40                  45
Val His Tyr Ile Phe Leu Gly Ser Ile Met Leu Phe Val Phe Ile
               50                  55                  60
Thr Asn Pro Ala Pro Trp Ile Phe Lys Ile Leu Phe Tyr Cys Phe
               65                  70                  75
Leu Gly Thr Leu Phe Ile Ile Pro Ala Thr Ser Gln Phe Phe
               80                  85                  90
Asn Ala Leu Pro Ile Leu Thr Trp Val Ala Leu Tyr Phe Thr Ser
               95                 100                 105
Ser Tyr Phe Pro Asp Asp Arg Arg Pro Pro Ile Thr Val Lys Val
              110                 115                 120
Leu Pro Ala Val Glu Thr Ile Leu Tyr Gly Asp Asn Leu Ser Asp
              125                 130                 135
Ile Leu Ala Thr Ser Thr Asn Ser Phe Leu Asp Ile Leu Ala Trp
              140                 145                 150
Leu Pro Tyr Gly Leu Phe His Phe Gly Ala Pro Phe Val Val Ala
              155                 160                 165
Ala Ile Leu Phe Val Phe Gly Pro Pro Thr Val Leu Gln Gly Tyr
              170                 175                 180
Ala Phe Ala Phe Gly Tyr Met Asn Leu Phe Gly Val Ile Met Gln
              185                 190                 195
Asn Val Phe Pro Ala Ala Pro Pro Trp Tyr Lys Ile Leu Tyr Gly
              200                 205                 210
Leu Gln Ser Ala Asn Tyr Asp Met His Gly Ser Pro Gly Gly Leu
              215                 220                 225
Ala Arg Ile Asp Lys Leu Leu Gly Ile Asn Met Tyr Thr Thr Ala
              230                 235                 240
Phe Ser Asn Ser Ser Val Ile Phe Gly Ala Phe Pro Ser Leu His
              245                 250                 255
Ser Gly Cys Ala Thr Met Glu Ala Leu Phe Phe Cys Tyr Cys Phe
              260                 265                 270
Pro Lys Leu Lys Pro Leu Phe Ile Ala Tyr Val Cys Trp Leu Trp
              275                 280                 285
Trp Ser Thr Met Tyr Leu Thr His His Tyr Phe Val Asp Leu Met
              290                 295                 300
Ala Gly Ser Val Leu Ser Tyr Val Ile Phe Gln Tyr Thr Lys Tyr
              305                 310                 315
Thr His Leu Pro Ile Val Asp Thr Ser Leu Phe Cys Arg Trp Ser
              320                 325                 330
Tyr Thr Ser Ile Glu Lys Tyr Asp Ile Ser Lys Ser Asp Pro Leu
              335                 340                 345
Ala Ala Asp Ser Asn Asp Ile Glu Ser Val Pro Leu Ser Asn Leu
              350                 355                 360
Glu Leu Asp Phe Asp Leu Asn Met Thr Asp Glu Pro Ser Val Ser
              365                 370                 375
```

-continued

```
Pro Ser Leu Phe Asp Gly Ser Thr Ser Val Ser Arg Ser Ser Ala
                380                 385                 390

Thr Ser Ile Thr Ser Leu Gly Val Lys Arg Ala
                395                 400
```

(2) INFORMATION FOR SEQ ID NO:7:

(i) SEQUENCE CHARACTERISTICS:
        (A) LENGTH: 422 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Ser Ala Leu Ser Thr Leu Lys Lys Arg Leu Ala Ala Cys Asn
 1               5                  10                  15

Arg Ala Ser Gln Tyr Lys Leu Glu Thr Ser Leu Asn Pro Met Pro
                20                  25                  30

Thr Phe Arg Leu Leu Arg Asn Thr Lys Trp Ser Trp Thr His Leu
                35                  40                  45

Gln Tyr Val Phe Leu Ala Gly Asn Leu Ile Phe Ala Cys Ile Val
                50                  55                  60

Ile Glu Ser Pro Gly Phe Trp Gly Lys Phe Gly Ile Ala Cys Leu
                65                  70                  75

Leu Ala Ile Ala Leu Thr Val Pro Leu Thr Arg Gln Ile Phe Phe
                80                  85                  90

Pro Ala Ile Val Ile Ile Thr Trp Ala Ile Leu Phe Tyr Ser Cys
                95                 100                 105

Arg Phe Ile Pro Glu Arg Trp Arg Pro Ile Trp Val Arg Val
                110                 115                 120

Leu Pro Thr Leu Glu Asn Ile Leu Tyr Gly Ser Asn Leu Ser Ser
                125                 130                 135

Leu Leu Ser Lys Thr Thr His Ser Ile Leu Asp Ile Leu Ala Trp
                140                 145                 150

Val Pro Tyr Gly Val Met His Tyr Ser Ala Pro Phe Ile Ile Ser
                155                 160                 165

Phe Ile Leu Phe Ile Phe Ala Pro Pro Gly Thr Leu Pro Val Trp
                170                 175                 180

Ala Arg Thr Phe Gly Tyr Met Asn Leu Phe Gly Val Leu Ile Gln
                185                 190                 195

Met Ala Phe Pro Cys Ser Pro Pro Trp Tyr Glu Asn Met Tyr Gly
                200                 205                 210

Leu Glu Pro Ala Thr Tyr Ala Val Arg Gly Ser Pro Gly Leu
                215                 220                 225

Ala Arg Ile Asp Ala Leu Phe Gly Thr Ser Ile Tyr Thr Asp Gly
                230                 235                 240

Phe Ser Asn Ser Pro Val Val Phe Gly Ala Phe Pro Ser Leu His
                245                 250                 255

Ala Gly Trp Ala Met Leu Glu Ala Leu Phe Leu Ser His Val Phe
                260                 265                 270

Pro Arg Tyr Arg Phe Cys Phe Tyr Gly Tyr Val Leu Trp Leu Cys
                275                 280                 285

Trp Cys Thr Met Tyr Leu Thr His His Tyr Phe Val Asp Leu Val
                290                 295                 300
```

```
Gly Gly Met Cys Leu Ala Ile Ile Cys Phe Val Phe Ala Gln Lys
                305                 310                 315

Leu Arg Leu Pro Gln Leu Gln Thr Gly Lys Ile Leu Arg Trp Glu
                320                 325                 330

Tyr Glu Phe Val Ile His Gly His Gly Leu Ser Glu Lys Thr Ser
                335                 340                 345

Asn Ser Leu Ala Arg Thr Gly Ser Pro Tyr Leu Leu Gly Arg Asp
                350                 355                 360

Ser Phe Thr Gln Asn Pro Asn Ala Val Ala Phe Met Ser Gly Leu
                365                 370                 375

Asn Asn Met Glu Leu Ala Asn Thr Asp His Glu Trp Ser Val Gly
                380                 385                 390

Ser Ser Ser Pro Glu Pro Leu Pro Ser Pro Ala Ala Asp Leu Ile
                395                 400                 405

Asp Arg Pro Ala Ser Thr Thr Ser Ser Ile Phe Asp Ala Ser His
                410                 415                 420

Leu Pro (2) INFORMATION FOR SEQ ID NO:8:

(i) SEQUENCE CHARACTERISTICS:
        (A) LENGTH:  471 amino acids
        (B) TYPE:  amino acid
        (C) STRANDEDNESS:  single
        (D) TOPOLOGY:  linear (ii) MOLECULE TYPE:  peptide (xi) SEQUENCE DESCRIPTION: SEQ ID NO:8:

Met Ala Ser Ser Ile Leu Arg Ser Lys Ile Gln Lys Pro Tyr
  1               5                  10                  15

Gln Leu Phe His Tyr Tyr Phe Leu Ser Glu Lys Ala Pro Gly Ser
                 20                  25                  30

Thr Val Ser Asp Leu Asn Phe Asp Thr Asn Ile Gln Thr Ser Leu
                 35                  40                  45

Arg Lys Leu Lys His His His Trp Thr Val Gly Glu Ile Phe His
                 50                  55                  60

Tyr Gly Phe Leu Val Ser Ile Leu Phe Phe Val Phe Val Val Phe
                 65                  70                  75

Pro Ala Ser Phe Phe Ile Lys Leu Pro Ile Ile Leu Ala Phe Ala
                 80                  85                  90

Thr Cys Phe Leu Ile Pro Leu Thr Ser Gln Phe Phe Leu Pro Ala
                 95                 100                 105

Leu Pro Val Phe Thr Trp Leu Ala Leu Tyr Phe Thr Cys Ala Lys
                110                 115                 120

Ile Pro Gln Glu Trp Lys Pro Ala Ile Thr Val Lys Val Leu Pro
                125                 130                 135

Ala Met Glu Thr Ile Leu Tyr Gly Asp Asn Leu Ser Asn Val Leu
                140                 145                 150

Ala Thr Ile Thr Thr Gly Val Leu Asp Ile Leu Ala Trp Leu Pro
                155                 160                 165

Tyr Gly Ile Ile His Phe Ser Phe Pro Phe Val Leu Ala Ala Ile
                170                 175                 180

Ile Phe Leu Phe Gly Pro Pro Thr Ala Leu Arg Ser Phe Gly Phe
                185                 190                 195

Ala Phe Gly Tyr Met Asn Leu Leu Gly Val Leu Ile Gln Met Ala
```

```
                    200             205                 210
Phe Pro Ala Ala Pro Pro Trp Tyr Lys Asn Leu His Gly Leu Glu
                215                 220                 225
Pro Ala Asn Tyr Ser Met His Gly Ser Pro Gly Gly Leu Gly Arg
                230                 235                 240
Ile Asp Lys Leu Leu Gly Val Asp Met Tyr Thr Thr Gly Phe Ser
                245                 250                 255
Asn Ser Ser Ile Ile Phe Gly Ala Phe Pro Ser Leu His Ser Gly
                260                 265                 270
Cys Cys Ile Met Glu Val Leu Phe Leu Cys Trp Leu Phe Pro Arg
                275                 280                 285
Phe Lys Phe Val Trp Val Thr Tyr Ala Ser Trp Leu Trp Trp Ser
                290                 295                 300
Thr Met Tyr Leu Thr His His Tyr Phe Val Asp Leu Ile Gly Gly
                305                 310                 315
Ala Met Leu Ser Leu Thr Val Phe Glu Phe Thr Lys Tyr Lys Tyr
                320                 325                 330
Leu Pro Lys Asn Lys Glu Gly Leu Phe Cys Arg Trp Ser Tyr Thr
                335                 340                 345
Glu Ile Glu Lys Ile Asp Ile Gln Glu Ile Asp Pro Leu Ser Tyr
                350                 355                 360
Asn Tyr Ile Pro Val Asn Ser Asn Asp Asn Glu Ser Arg Leu Tyr
                365                 370                 375
Thr Arg Val Tyr Gln Glu Ser Gln Val Ser Pro Pro Gln Arg Ala
                380                 385                 390
Glu Thr Pro Glu Ala Phe Glu Met Ser Asn Phe Ser Arg Ser Arg
                395                 400                 405
Gln Ser Ser Lys Thr Gln Val Pro Leu Ser Asn Leu Thr Asn Asn
                410                 415                 420
Asp Gln Val Ser Gly Ile Asn Glu Glu Asp Glu Glu Glu Glu Gly
                425                 430                 435
Asp Glu Ile Ser Ser Ser Thr Pro Ser Val Phe Glu Asp Glu Pro
                440                 445                 450
Gln Gly Ser Thr Tyr Ala Ala Ser Ser Ala Thr Ser Val Asp Asp
                455                 460                 465
Leu Asp Ser Lys Arg Asn
                470

(2) INFORMATION FOR SEQ ID NO:9:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:  peptide (ix) FEATURE:
        (A) NAME/KEY:
        (B) LOCATION:
        (C) IDENTIFICATION METHOD:
        (D) OTHER INFORMATION:  /note= "Xaa at position 3 is Val or
            Ile"

(ix) FEATURE:
        (A) NAME/KEY:
        (B) LOCATION:
        (C) IDENTIFICATION METHOD:
        (D) OTHER INFORMATION: /note= "Xaa at position 7 is Leu or
```

Val"

(xi) SEQUENCE DESCRIPTION: SEQ ID NO:9:

Leu Asp Xaa Leu Ala Trp Xaa Pro Tyr Gly
 1               5                   10

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Phe Gly Ala Phe Pro Ser Leu His
 1               5

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (B) LOCATION:
        (C) IDENTIFICATION METHOD:
        (D) OTHER INFORMATION: /note= "Xaa at position 5 is Ser or
            Thr"

(ix) FEATURE:
        (A) NAME/KEY:
        (B) LOCATION:
        (C) IDENTIFICATION METHOD:
        (D) OTHER INFORMATION: /note= "Xaa at position 9 is Ala or
            Phe"

(xi) SEQUENCE DESCRIPTION: SEQ ID NO:11:

Thr Met Tyr Leu Xaa His His Tyr Xaa Val Asp Leu
 1               5                   10

(2) INFORMATION FOR SEQ ID NO:12:

(i) SEQUENCE CHARACTERISTICS:
        (A) LENGTH: 2935 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

```
ATTTTCTTCC CCATAACAAC TCTTCTCGCC CTTCCTCCGG CTCCGTGGCC AAATTGTTTT      60

ATGCAGCGCC TCCTAGCGAT TTAACCTCGT TCTCGTTGCC CTTGCCTGTC CGCCTTGCGT     120

CAGTACGACC CTTGCAACGT GACCTTCCCC AGAGTATCCT CGTTTGGCCG CTGGAGACCG     180

GAGCTTGCAC CCTCATAAAC TAGCTCTTCG AAATCAATTC TCCGTTCTCC AGAGATTATC     240

GGATCGAATC TCTCCGCTGT CGACACCTTT CGTCTCTCGG TGATCCTCGC CCTTGGAGTC     300

TCGTCACGTT GACGCCTTGA ACCCCTGGCC GCCAACTCCA CATAGGAGAC CACACTTCAT     360

TCTTCCCCCG CCATAATTGC AGCACCCTCC GTCTCCCTTC GAGCTCCTCC TGGATCATCA     420
```

```
AGTCCGAAAG GATTAGACTC GTCGCAGCGA TGAATACCAC CCTTCCATCC TGGAAGGATC      480

GGACGCAAAA CCAGTTCGGC AAGCTCCAGA TCCAAGTCCC ATGGCGCACC ATACAACTTC      540

TCGTGCCGCA CCGTATGCGA CGGAAGATTC GGTCCAAGCT GCGCAGTCGG ATCTCGCCTA      600

CCTCATCGAT ATCCTCGTTG CAGACGTCAT TCTCACCTGT CGATACACTC AGGTCGCTGC      660

AAAGTCATAG ATGGACGCTC TATGACTTTC AGTATCTTTT GCTGCTGATT GTCGGCATAT      720

TCTCGCTGAG CGTTATGGAA TCACCTGGAC CATTGGCAAA GACCGCCGCG TTTACGCTAC      780

TTCTCGTCTC TCTCCTTCTC CCGATTACGC GCCAGTTCTT CTTGCCATTC CTCCCGATTG      840

CAGGATGGCT TATATTTTTC TACGCTTGCC AGTTCATCCC GAGCGACTGG CGCCCTGCAA      900

TCTGGGTTCG CGTGCTGCCG GCTCTGGAAA ACATTCTCTA CGGTGCTAAT ATCAGTAACA      960

TCCTTTCCGC TCACCAAAAT GTGGTGCTTG ACGTTTTGGC GTGGCTTCCC TACGGAATCT     1020

GCCATTATGG CGCGCCATTT GTGTGCTCAG CGATCATGTT CATCTTTGGT CCTCCCGGCA     1080

CCGTCCCCCT TTTCGCTCGA ACTTTTGGAT ACATCAGCAT GGCTGCAGTC ACCATTCAGC     1140

TGTTTTTCCC CTGCTCTCCT CCGTGGTACG AAAATCTGTA TGGTTTGGCT CCGGCTGATT     1200

ACTCCATGCC GGGTAATCCT GCGGGCCTTG CTCGCATCGA TGAGCTTTTT GGGATAGACT     1260

TGTACACATC GGGCTTCAGA CAATCTCCCG TCGTGTTTGG CGCATTTCCT TCCCTACATG     1320

CCGCTGATTC GACACTTGCA GCTCTATTTA TGAGCCAAGT GTTCCCACGG TTGAAGCCCT     1380

TGTTTGTCAT CTATACTCTC TGGATGTGGT GGGCTACAAT GTATCTTTCG CACCACTACG     1440

CTGTTGATCT GGTCGGTGGT GGCCTCTTGG CAACTGTCGC GTTCTACTTT GCTAAAACGC     1500

GGTTCATGCC TCGCGTCCAG AATGATAAGA TGTTCCGCTG GACTACGAT TATGTTGAGT      1560

ACGGCGATTC CGCACTCGAC TATGGGTACG GTCCAGCCAG CTTCGAAGGC GAATTCAACC     1620

TTGATAGCGA TGAGTGGACC GTTGGTTCTT CGTCATCCAT TTCGTCCGGC TCCCTCAGTC     1680

CAGTTGACGA CCACTACTCT TGGGAGGGCG AGACTCTTGC CTCTCCTGCC ACCGACATCG     1740

AGTCTGGAAG GCATTTCTGA TCCTGCTCAA TGAGCCTTGA TACGTACTAC ACTGTGTACG     1800

TGCTACTGCA TTGACTAATG AGACGGCGTT TTCAAACAAA TTTTAACGAC ATGCTTGGTT     1860

ATCGCATTGA GCTGATTTCG ACACATATAT ATGTTTAATA CGTTTTGGGG ACACTCCAGG     1920

GATTCATGAC GGTTGCTTCA TATCCCGACC TGGGGATGGA TTGACCTGGT TGTGCCCAAT     1980

TTTCTTCTGC CTAACGTTTT GATTATACAT GCATTTTTCA CGAAACCAGC CGGCCCGCCA     2040

TGATCGTGAC CTCAATTTGA GCTCGAATCT TCCTGGGGCC TCCAGCGATA ATTCTTAATG     2100

CTCGTTCCGA GGGTGCCACA TCGGACATTC GCTTGTACAA CTTTTGCAGA CGAACATTT      2160

TCACCGATTC CAACTTGAGT CATTCGCTTA CTACTTTCAA CTGGTCGAGA AACTTCGCTT     2220

CTTTTCAGCT CGGCTAGGTG CATAAATATT TTACATTCGT GTCGATCGCT CACATTTCAC     2280

GGCGCCTGGA AACTTGGGGG TTTCGATTTC ATTGGAAAGG ATAAACAACA TGGGCTGGGC     2340

GCCTTTTACA CGCACTACAT TCGCTTAGAA AAGTTCTGAT GCTTTTAATG ATTCTTGCAT     2400

TGGCATATAG AAAGGGGTCC TCCAGACTCG CTACTGTGGT CCTCTCTCAA CCCCACACTC     2460

GCTTGCTTTT AACAGTGGAC ACCCCGTGGA GCTACGTCTC CATCAAATAT TTGGCATCAA     2520

CCGGAATCGA TGCCAGGAGG ACTGAGCTTA CTCACGGTGA CCGTCGGGTA AAAGGCGTTC     2580

ATACAGAACA TCTCCTCTAT CCTCCTGTCC CATCTCGATT CTCTGGCTGC TGGACGCAAC     2640

ACACCTCGCT GCACGTTTTC GACTTCCTAA TACGACCTAA TATCATTCTC GGTTTTCTTT     2700

GCTCTGGCTC GCGGCCGCCA TTTATATGGC GTGTCGGCTC GAGTCTGAAG TGAACTTTTT     2760
```

-continued

```
TCTCCTTTCT GGCCTCCACA ACTTTCCGAT CCCTAGCAGC TTCCCGTGCA CAGCGAGGTG    2820

TTGTTGGATG ATTGTTCCAT AGCATTATCA TTATTCCTAA TCCGGTAGCG TTATGATTTA    2880

TGAAGAACAG TGATGTACAT TATTATGCGG TGATCAAAAA AAAAAAAAAA AAAAA         2935
```

(2) INFORMATION FOR SEQ ID NO:13:

(i) SEQUENCE CHARACTERISTICS:
        (A) LENGTH: 2856 base pairs
        (B) TYPE: nucleic acid
        (C) STRANDEDNESS: double
        (D) TOPOLOGY: linear (ii) MOLECULE TYPE: Genomic DNA (iv) ANTI-SENSE: Yes (xi) SEQUENCE DESCRIPTION: SEQ ID NO:13:

```
TAGTATACAA GTTGCCTTCA TAAATCATAA CACTACCGGA TTATAACTAA TAATACTGCT      60

GCTATGGATA ATTTGCCCCA ACCACACACA CACACACACT ATCCAAGGGA AACGAAAAGA     120

AGAGGATAGT GTCCATGAGC GGAATTTGTG AGGTGAGGAG GATGTGATAG GTAGGTGTGA     180

GAGCGTCAGA CCATAGCAAG CAAGTCAAGT CACCGTCCAA CAAGTCGAGA ATCTGAGGTT     240

AGTCGAAGCC GGGTCAAATC GGGACGCGTG AACATCCTTC AACAAGCCCC GTCAGCGTCA     300

GACTCTCCTC CCAACCTTGC ACGTCCGGCG AATGTCAGAA AGCAACACAG TAGCCATGTG     360

TATAGCCCCC GGGTAATATG TGGACGTAAT CCACTTTGAG CGAATGGATA AACCATGCGA     420

GCAATCAAGA AGAAGGTCCA TCCTTCCCCT CTTTCTATAT GCTAATGCAG AGTTCGTGAT     480

GCATTGCAAA GCAGAAATGT AAAACCGTCT ATGCACAGCG AGTGAAGTGC AAGAAGAAAA     540

GGCGCCCCAT TCCGTGATTT TTTCCAATAT AAATGCTTCC AGTCCCAAGC GCCAAGAGTA     600

TGAGCGATCG ACACGAATGG TAAAAATAAA TATATAGCAT AGTCGAAACG AATAATAAGG     660

ATGGGTTCGA CCAGGTCAAG GTAATAGCGG ACGATAGAAG TGAGAATTGA AGTAGTGTCT     720

GGGTGGACAC GAGACAAGCG AGTGTTACCG ACGGGGGTTA TCGGATGGTC TTCCAGGACT     780

AAACACCAGG ATGCGTAGCC CCATTGTGTC CATTAACATT ATGATGGAGC AACGGCGTGT     840

AGCGATGAGC GATAACCCAT CCCACGTTCG AGCCCAACCC GGTTTCGCAA TGTCAAGCAA     900

TGTACAGTGA AGTGCGGCGG AAAGAGAAAC AGTATCCCAG GCGGATTCGG ACCGAGGTAC     960

ATTAAGGTCG AACCGATGAT CTGGGACACC GAAGAAAGGG TATTAAAGAT ATATGTGTCG    1020

AAATGTGCTC GATGCAATAA AGCCAGAATG TCGTGAAATG TTCTAACGCC GTCTCGTAAA    1080

TAGATGCAGT GGAGGAGGAG CGAGATCGCT ATATGCAGGT ATCGAGTTTG GTTTGTGGCT    1140

ACTCAAGGGC TGAAAGTATG CCTGCCGGAC TCAATATCAG TATGTGGGA GGTCAGTGCC     1200

TCGGTTTCCC ATGAGTAATG ATCGTCAACG GGACTCAAGG AGCCTGAGGA GACGGAGGAT    1260

GAAGAACCAA CAGTCCATTC ATCGCTGTCG AGATTGAAGT CTCCATCATA GCCAGCTGCA    1320

CCATACCCAT ACTCCAGGGC AGACTCGCCG AATTCCACAT AGTCGTAGTC CAACGGAAG     1380

GTCTTGTCGA GCTGGACACG GGGAAGGAAT CGGGTCTTGG CGAAGTAGAA AGCAATGGCG    1440

GCCAGGAGAC CACCCGCAAC CAAATCGACC GCATAGTGAT GTGAGAGGTA CATTGTTGCC    1500

CACCACATCC ATAGAGTATA GGTCACGAAG ACGGGCTTCA TGCGGGGAA AACATGACTC     1560

ATGAAAAGTG CGGCCAGGGT TGAGTCGGCA GCATGCAGCG ACGGAAAAGC GCCGAACACA    1620

ACAGGCGACT GATGGAAAAC AGACGTGTAA AGGTCGATGC CGAAAAGCTT GTCAATGCGG    1680

GCAAGCCCTG CGGGATCACC TTGGATGGAG TAGTCTGCCG GAGCTAGACC ATAGCGATTC    1740
```

```
TCATACCAAG GTGGAGAGCA AGGGAAAAAC AGCTGAATAG TAACCGCAGT CATACTGATA    1800

TAGCCGAAAG TGCGCGCGAA AAGGGGAACA GTGCCGGGCG GACCGAAGAT GAACATGATC    1860

AACGAGCACA CAAACGGAGC GCCATAGTGG CAGATACCGT AGGGTAGCCA CGCCAGCACG    1920

TCAAGCACAA CGTTCTGGTG AGCGGATAGG ATGTTGCTGA TGTTTGCGCC GTAGAGAATA    1980

TTCTCCAGTG CAGGCAAGAC ACGAACCCAA ATCGCAGGGC GCCAATCGCT TGGGATGAAC    2040

TGGCAGGCGT AGAAAAACAG AAGCCATCCG GCAATCGGCA GAAACGGGAG GAAGAACTGG    2100

CGGGTCATAG GGATCAGGAG AGAGAATAGG AGCATGGAGA AAATGGCCGT TTTGCCCAAA    2160

GGCCCGGGCG ACTCGATAAC GGTCAAAGAG AAGATGCCCA CGATCAACAG AAGCAGATAT    2220

TGGAAGTCGT AAACCGTCCA TCGGTGGCTT TGGAGCGATC GTAGTGTGTC TGCAGGCGAT    2280

AACGACGTCT GTAAAGAGGC TATTGACGAG GTAGGAGACG CTCTACTGCG CAATTTGGAC    2340

CTTAACTTCC GCCGCATGCG ATGCGGGACG AGCAGTTGGA TGGACCGCCA TGGAACCTGG    2400

ATCTGAAGCT TTCCAAACTG GTTCTGCGTG CGGTCCTTCC ACGTGGGAAG TGTTTGATTC    2460

ATGGTTGCGG CGAGTCTTGC GGGCAAGACT CAGCTATAAT TCCTCCAGAT CGAACTCCGT    2520

CTGCTTTCTT TCCCCCCGAT TGTACAAGAG TTGGAAGGCG ACGAATAAAT CGGTCGCGGA    2580

AGCGGCAGAA AAGGGGTCTT GAATAACAAG CCGTTAGGCA ACGAGCAGGG TGCTGACGGC    2640

GTCAACCCGA GCGGGGAAAT TGAGATCGGT TCGAAGAAGA CGAAACGAAG CGCACGCTCC    2700

GGTCTCCAGC GGCCAAACGA GGATGTCTTT GAGCCGTCAC GTTGCAGGGG GTTTCACTGA    2760

TGCAAGGCGA AGTGCAAGGG CGCAGCAGTC GAGAGGAAAA CCTGGAACGA GGAGGTCGTG    2820

AGGGAGGCAG ATGGCCACGG AGCCGGAGTA TAAACC                              2856

(2) INFORMATION FOR SEQ ID NO:14:

(i) SEQUENCE CHARACTERISTICS:
        (A) LENGTH: 2856 bases
        (B) TYPE: nucleic acid
        (C) STRANDEDNESS: single
        (D) TOPOLOGY: linear (ii) MOLECULE TYPE: mRNA (iv) ANTI-SENSE: Yes (xi) SEQUENCE DESCRIPTION: SEQ ID NO:14:

UAGUAUACAA GUUGCCUUCA UAAAUCAUAA CACUACCGGA UUAUAACUAA UAAUACUGCU      60

GCUAUGGAUA AUUUGCCCCA ACCACACACA CACACACACU AUCCAAGGGA AACGAAAAGA    120

AGAGGAUAGU GUCCAUGAGC GGAAUUUGUG AGGUGAGGAG GAUGUGAUAG GUAGGUGUGA    180

GAGCGUCAGA CCAUAGCAAG CAAGUCAAGU CACCGUCCAA CAAGUCGAGA AUCUGAGGUU    240

AGUCGAAGCC GGGUCAAAUC GGGACGCGUG AACAUCCUUC AACAAGCCCC GUCAGCGUCA    300

GACUCUCCUC CCAACCUUGC ACGUCCGGCG AAUGUCAGAA AGCAACACAG UAGCCAUGUG    360

UAUAGCCCCC GGGUAAUAUG UGGACGUAAU CCACUUUGAG CGAAUGGAUA AACCAUGCGA    420

GCAAUCAAGA AGAAGGUCCA UCCUUCCCCU CUUUCUAUAU GCUAAUGCAG AGUUCGUGAU    480

GCAUUGCAAA GCAGAAAUGU AAAACCGUCU AUGCACAGCG AGUGAAGUGC AAGAAGAAAA    540

GGCGCCCCAU UCCGUGAUUU UUUCCAAUAU AAAUGCUUCC AGUCCCAAGC GCCAAGAGUA    600

UGAGCGAUCG ACACGAAUGG UAAAAAUAAA UAUAUAGCAU AGUCGAAACG AAUAAUAAGG    660

AUGGGUUCGA CCAGGUCAAG GUAAUAGCGG ACGAUAGAAG UGAGAAUUGA AGUAGUGUCU    720

GGGUGGACAC GAGACAAGCG AGUGUUACCG ACGGGGGUUA UCGGAUGGUC UUCCAGGACU    780
```

-continued

| | |
|---|---|
| AAACACCAGG AUGCGUAGCC CCAUUGUGUC CAUUAACAUU AUGAUGGAGC AACGGCGUGU | 840 |
| AGCGAUGAGC GAUAACCCAU CCCACGUUCG AGCCCAACCC GGUUUCGCAA UGUCAAGCAA | 900 |
| UGUACAGUGA AGUGCGGCGG AAAGAGAAAC AGUAUCCCAG GCGGAUUCGG ACCGAGGUAC | 960 |
| AUUAAGGUCG AACCGAUGAU CUGGGACACC GAAGAAAGGG UAUUAAAGAU AUAUGUGUCG | 1020 |
| AAAUGUGCUC GAUGCAAUAA AGCCAGAAUG UCGUGAAAUG UUCUAACGCC GUCUCGUAAA | 1080 |
| UAGAUGCAGU GGAGGAGGAG CGAGAUCGCU AUAUGCAGGU AUCGAGUUUG GUUUGUGGCU | 1140 |
| ACUCAAGGGC UGAAAGUAUG CCUGCCGGAC UCAAUAUCAG UAUGUGGGGA GGUCAGUGCC | 1200 |
| UCGGUUUCCC AUGAGUAAUG AUCGUCAACG GGACUCAAGG AGCCUGAGGA GACGGAGGAU | 1260 |
| GAAGAACCAA CAGUCCAUUC AUCGCUGUCG AGAUUGAAGU CUCCAUCAUA GCCAGCUGCA | 1320 |
| CCAUACCCAU ACUCCAGGGC AGACUCGCCG AAUUCCACAU AGUCGUAGUC CAACGGAAG | 1380 |
| GUCUUGUCGA GCUGGACACG GGAAGGAAU CGGGUCUUGG CGAAGUAGAA AGCAAUGGCG | 1440 |
| GCCAGGAGAC CACCCGCAAC CAAAUCGACC GCAUAGUGAU GUGAGAGGUA CAUUGUUGCC | 1500 |
| CACCACAUCC AUAGAGUAUA GGUCACGAAG ACGGGCUUCA UGCGGGGAA AACAUGACUC | 1560 |
| AUGAAAAGUG CGGCCAGGGU UGAGUCGGCA GCAUGCAGCG ACGGAAAAGC GCCGAACACA | 1620 |
| ACAGGCGACU GAUGGAAAAC AGACGUGUAA AGGUCGAUGC CGAAAAGCUU GUCAAUGCGG | 1680 |
| GCAAGCCCUG CGGGAUCACC UUGGAUGGAG UAGUCUGCCG GAGCUAGACC AUAGCGAUUC | 1740 |
| UCAUACCAAG GUGGAGAGCA AGGGAAAAAC AGCUGAAUAG UAACCGCAGU CAUACUGAUA | 1800 |
| UAGCCGAAAG UGCGCGCGAA AAGGGGAACA GUGCCGGGCG GACCGAAGAU GAACAUGAUC | 1860 |
| AACGAGCACA CAAACGGAGC GCCAUAGUGG CAGAUACCGU AGGGUAGCCA CGCCAGCACG | 1920 |
| UCAAGCACAA CGUUCUGGUG AGCGGAUAGG AUGUUGCUGA UGUUUGCGCC GUAGAGAAUA | 1980 |
| UUCUCCAGUG CAGGCAAGAC ACGAACCCAA AUCGCAGGGC GCCAAUCGCU UGGGAUGAAC | 2040 |
| UGGCAGGCGU AGAAAAACAG AAGCCAUCCG GCAAUCGGCA GAAACGGGAG GAAGAACUGG | 2100 |
| CGGGUCAUAG GGAUCAGGAG AGAGAAUAGG AGCAUGGAGA AAAUGGCCGU UUUGCCCAAA | 2160 |
| GGCCCGGGCG ACUCGAUAAC GGUCAAAGAG AAGAUGCCCA CGAUCAACAG AAGCAGAUAU | 2220 |
| UGGAAGUCGU AAACCGUCCA UCGGUGGCUU UGGAGCGAUC GUAGUGUGUC UGCAGGCGAU | 2280 |
| AACGACGUCU GUAAAGAGGC UAUUGACGAG GUAGGAGACG CUCUACUGCG CAAUUUGGAC | 2340 |
| CUUAACUUCC GCCGCAUGCG AUGCGGGACG AGCAGUUGGA UGGACCGCCA UGGAACCUGG | 2400 |
| AUCUGAAGCU UUCCAAACUG GUUCUGCGUG CGGUCCUUCC ACGUGGGAAG UGUUUGAUUC | 2460 |
| AUGGUUGCGG CGAGUCUUGC GGGCAAGACU CAGCUAUAAU UCCUCCAGAU CGAACUCCGU | 2520 |
| CUGCUUUCUU UCCCCCCGAU UGUACAAGAG UUGGAAGGCG ACGAAUAAAU CGGUCGCGGA | 2580 |
| AGCGGCAGAA AAGGGGUCUU GAAUAACAAG CCGUUAGGCA ACGAGCAGGG UGCUGACGGC | 2640 |
| GUCAACCCGA GCGGGAAAU UGAGAUCGGU UCGAAGAAGA CGAAACGAAG CGCACGCUCC | 2700 |
| GGUCUCCAGC GGCCAAACGA GGAUGUCUUU GAGCCGUCAC GUUGCAGGGG GUUUCACUGA | 2760 |
| UGCAAGGCGA AGUGCAAGGG CGCAGCAGUC GAGAGGAAAA CCUGGAACGA GGAGGUCGUG | 2820 |
| AGGGAGGCAG AUGGCCACGG AGCCGGAGUA UAAACC | 2856 |

(2) INFORMATION FOR SEQ ID NO:15:

(i) SEQUENCE CHARACTERISTICS:
        (A) LENGTH: 2385 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:15:

```
AAGCTTTTTT GCCTCTGCAA AAGTTCCTTT CTCGAATTGG TTTTTTGAGG AAAAGCAAGT      60
TAATAAACTA ATTATATTAT ATATAATTAG CAATTTTATA AAAAAAATAA AAAAATAGCC     120
CTGATTGCTG GCAACTGTGA GCTGAACATT GGTTAATCGG TCCATCTTTT TTTAAATATT     180
TTACATCGCT ACTTTTAAGT GCTTGACACT TGCATTTAAT AGCTACTTTC TTTCCTTCAT     240
AAAAATTCCT TTTTTTTCCT TTAGTTTTCC GGTTAATTCC TTACGAAATT TTTTTCGTAC     300
GCTTCCCTTT TTTACTCTGA TAATTCTTTG AAGCAATGTC TGCTCTTTCG ACCTTAAAAA     360
AGCGCCTTGC TGCGTGTAAC CGAGCATCCC AATACAAGTT GGAAACAAGC TTAAACCCTA     420
TGCCTACATT TCGTTTGCTA CGCAATACGA AATGGTCATG GACACATTTG CAATATGTGT     480
TTCTAGCAGG TAATTTGATT TTTGCTTGTA TTGTCATTGA ATCTCCTGGA TTCTGGGGGA     540
AATTTGGCAT TGCCTGTCTT TTGGCCATTG CGTTGACCGT TCCTTTAACA CGCCAAATTT     600
TTTTTCCTGC CATTGTTATC ATCACCTGGG CAATTTTATT TTACTCTTGT AGGTTTATTC     660
CAGAACGCTG GCGTCCACCC ATATGGGTTC GTGTTTTACC CACACTTGAA AATATTCTTT     720
ATGGCTCTAA TCTTTCTAGT CTTCTCTCGA AAACCACGCA TAGCATCCTT GATATTTTGG     780
CCTGGGTTCC ATATGGAGTC ATGCATTATT CGGCTCCTTT TATCATTTCA TTTATTCTTT     840
TCATCTTTGC ACCTCCTGGA ACTCTTCCAG TTTGGGCTCG AACTTTTGGT TATATGAATT     900
TATTTGGTGT TCTTATCCAA ATGGCTTTCC CCTGTTCTCC TCCTTGGTAT GAAAATATGT     960
ATGGTTTAGA ACCTGCCACG TATGCAGTAC GTGGCTCTCC TGGTGGATTG GCCCGTATTG    1020
ATGCTCTCTT CGGCACTAGC ATTTACACTG ATTGTTTTTC TAACTCTCCG GTTGTTTTTG    1080
GTGCCTTTCC ATCTCTTCAC GCTGGATGGG CCATGCTGGA AGCACTTTTC CTTTCGCATG    1140
TGTTTCCTCG ATACCGCTTC TGCTTTTATG GATATGTTCT ATGGCTTTGC TGGTGTACTA    1200
TGTACCTTAC CCACCACTAC TTTGTAGATT TGGTCGGCGG TATGTGTTTA GCTATTATAT    1260
GCTTCGTTTT TGCTCAAAAG CTACGCCTCC CACAGTTGCA AACTGGTAAA ATCCTTCGTT    1320
GGGAATACGA GTTTGTTATC CACGGTCATG GTCTTTCCGA AAAACCAGC AACTCCTTGG     1380
CTCGTACCGG CAGCCCATAC TTACTTGGAA GGGATTCTTT TACTCAAAAC CCTAATGCAG    1440
TAGCCTTCAT GAGTGGTCTT AACAATATGG AACTTGCTAA CACCGATCAT GAATGGTCCG    1500
TGGGTTCATC ATCACCTGAG CCGTTACCTA GTCCTGCTGC TGATTTGATT GATCGTCCTG    1560
CCAGTACCAC TTCCTCCATC TTTGATGCAA GTCATCTTCC TTAAATCAAC GTGCTTTAAG    1620
AATATATTTC CAAAAGCTAC ATGATACATT GACTAGAATC GGTTTGATTC ATAGTGGTAT    1680
TGGAATGATG TTGTTCATTG TGTTTTTTAA CTGTTAATCT GACATCCATT GAGTCATTCT    1740
TTACAATTTG TAAAATTAAT TTGTATCACT AATTTTGAAG GAAGCTATTT TGGTATTAAT    1800
ACCGCTTTTG GTCTCCACTT CCTTTTCGAA ACTCTTAACA GCGATTAGGC CGGGTATCTT    1860
CCAGTGTGAT GTATAGGTAT TTGTCGTTTT TTTATCATTT CCGTTAATAA AGAACTCTTT    1920
TATCCAGCTT CTTACACTGT CAACTGTTGT GAAAGGAACA CATTTAGAAT TCATTTTCC     1980
TTATTTGTTG TGATTTAAAT CGTTTGACAT AATTTTAAAT TTGGTTTGAA ATGTGTGTGA    2040
GAAGGCTTGT TTTATTCATT TAGTTTATTG CTTGTTTGCA CGAAAATCCA GAACGGAGCA    2100
TTAATGTAAT CCTTTTTTAT TCTGTAAAGC GTTTTTATAC AAATGTTGGT TATACGTTTC    2160
TAAAATAAGA ATATTGTTAT AATAATATAG TTTTTTCTAT CATTTGTTAC ACACACTAAA    2220
GAGACATTAA GGATAAGCAA ATGTGTTAAA ATGATAATAT ATTTTGGAAA CATTTATAAA    2280
```

```
GAAATTAAGC AGCTTTGACT AACTACATTT TTGTTTTTTT CCTAAGCAAA ACTGTATAGT    2340

TATACACGCG AGCTGTATTC ACTTCCATTG TAGTGACTTG AGCTC                    2385
```

(2) INFORMATION FOR SEQ ID NO:16:

(i) SEQUENCE CHARACTERISTICS:
        (A) LENGTH:  422 amino acids
        (B) TYPE:  amino acid
        (C) STRANDEDNESS:  single
        (D) TOPOLOGY:  linear (ii) MOLECULE TYPE: peptide (xi) SEQUENCE DESCRIPTION: SEQ ID NO:16:

```
Met Ser Ala Leu Ser Thr Leu Lys Lys Arg Leu Ala Ala Cys Asn
 1               5                  10                  15

Arg Ala Ser Gln Tyr Lys Leu Glu Thr Ser Leu Asn Pro Met Pro
            20                  25                  30

Thr Phe Arg Leu Leu Arg Asn Thr Lys Trp Ser Trp Thr His Leu
            35                  40                  45

Gln Tyr Val Phe Leu Ala Gly Asn Leu Ile Phe Ala Cys Ile Val
            50                  55                  60

Ile Glu Ser Pro Gly Phe Trp Gly Lys Phe Gly Ile Ala Cys Leu
            65                  70                  75

Leu Ala Ile Ala Leu Thr Val Pro Leu Thr Arg Gln Ile Phe Phe
            80                  85                  90

Pro Ala Ile Val Ile Ile Thr Trp Ala Ile Leu Phe Tyr Ser Cys
            95                 100                 105

Arg Phe Ile Pro Glu Arg Trp Arg Pro Ile Trp Val Arg Val
           110                 115                 120

Leu Pro Thr Leu Glu Asn Ile Leu Tyr Gly Ser Asn Leu Ser Ser
           125                 130                 135

Leu Leu Ser Lys Thr Thr His Ser Ile Leu Asp Ile Leu Ala Trp
           140                 145                 150

Val Pro Tyr Gly Val Met His Tyr Ser Ala Pro Phe Ile Ile Ser
           155                 160                 165

Phe Ile Leu Phe Ile Phe Ala Pro Pro Gly Thr Leu Pro Val Trp
           170                 175                 180

Ala Arg Thr Phe Gly Tyr Met Asn Leu Phe Gly Val Leu Ile Gln
           185                 190                 195

Met Ala Phe Pro Cys Ser Pro Pro Trp Tyr Glu Asn Met Tyr Gly
           200                 205                 210

Leu Glu Pro Ala Thr Tyr Ala Val Arg Gly Ser Pro Gly Gly Leu
           215                 220                 225

Ala Arg Ile Asp Ala Leu Phe Gly Thr Ser Ile Tyr Thr Asp Cys
           230                 235                 240

Phe Ser Asn Ser Pro Val Val Phe Gly Ala Phe Pro Ser Leu His
           245                 250                 255

Ala Gly Trp Ala Met Leu Glu Ala Leu Phe Leu Ser His Val Phe
           260                 265                 270

Pro Arg Tyr Arg Phe Cys Phe Tyr Gly Tyr Val Leu Trp Leu Cys
           275                 280                 285

Trp Cys Thr Met Tyr Leu Thr His His Tyr Phe Val Asp Leu Val
           290                 295                 300

Gly Gly Met Cys Leu Ala Ile Ile Cys Phe Val Phe Ala Gln Lys
```

```
                305                 310                 315
Leu Arg Leu Pro Gln Leu Gln Thr Gly Lys Ile Leu Arg Trp Glu
                320                 325                 330
Tyr Glu Phe Val Ile His Gly His Gly Leu Ser Glu Lys Thr Ser
                335                 340                 345
Asn Ser Leu Ala Arg Thr Gly Ser Pro Tyr Leu Leu Gly Arg Asp
                350                 355                 360
Ser Phe Thr Gln Asn Pro Asn Ala Val Ala Phe Met Ser Gly Leu
                365                 370                 375
Asn Asn Met Glu Leu Ala Asn Thr Asp His Glu Trp Ser Val Gly
                380                 385                 390
Ser Ser Ser Pro Glu Pro Leu Pro Ser Pro Ala Ala Asp Leu Ile
                395                 400                 405
Asp Arg Pro Ala Ser Thr Thr Ser Ser Ile Phe Asp Ala Ser His
                410                 415                 420
Leu Pro
```

(2) INFORMATION FOR SEQ ID NO:17:

(i) SEQUENCE CHARACTERISTICS:
        (A) LENGTH: 2385 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:17:

```
AAGCTTTTTT GCCTCTGCAA AAGTTCCTTT CTCGAATTGG TTTTTTGAGG AAAAGCAAGT    60

TAATAAACTA ATTATATTAT ATATAATTAG CAATTTTATA AAAAAAATAA AAAAATAGCC   120

CTGATTGCTG GCAACTGTGA GCTGAACATT GGTTAATCGG TCCATCTTTT TTTAAATATT   180

TTACATCGCT ACTTTTAAGT GCTTGACACT TGCATTTAAT AGCTACTTTC TTTCCTTCAT   240

AAAAATTCCT TTTTTTTCCT TTAGTTTTCC GGTTAATTCC TTACGAAATT TTTTTCGTAC   300

GCTTCCCTTT TTTACTCTGA TAATTCTTTG AAGCAATGTC TGCTCTTTCG ACCTTAAAAA   360

AGCGCCTTGC TGCGTGTAAC CGAGCATCCC AATACAAGTT GGAAACAAGC TTAAACCCTA   420

TGCCTACATT TCGTTTGCTA CGCAATACGA AATGGTCATG GACACATTTG CAATATGTGT   480

TTCTAGCAGG TAATTTGATT TTTGCTTGTA TTGTCATTGA ATCTCCTGGA TTCTGGGGGA   540

AATTTGGCAT TGCCTGTCTT TTGGCCATTG CGTTGACCGT TCCTTTAACA CGCCAAATTT   600

TTTTTCCTGC CATTGTTATC ATCACCTGGG CAATTTTATT TTACTCTTGT AGGTTTATTC   660

CAGAACGCTG GCGTCCACCC ATATGGGTTC GTGTTTTACC CACACTTGAA AATATTCTTT   720

ATGGCTCTAA TCTTTCTAGT CTTCTCTCGA AAACCACGCA TAGCATCCTT GATATTTTGG   780

CCTGGGTTCC ATATGGAGTC ATGCATTATT CGGCTCCTTT TATCATTTCA TTTATTCTTT   840

TCATCTTTGC ACCTCCTGGA ACTCTTCCAG TTTGGGCTCG AACTTTTGGT TATATGAATT   900

TATTTGGTGT TCTTATCCAA ATGGCTTTCC CCTGTTCTCC TCCTTGGTAT GAAAATATGT   960

ATGGTTTAGA ACCTGCCACG TATGCAGTAC GTGGCTCTCC TGGTGGATTG GCCCGTATTG  1020

ATGCTCTCTT CGGCACTAGC ATTTACACTG ATGGTTTTTC TAACTCTCCG GTTGTTTTTG  1080

GTGCCTTTCC ATCTCTTCAC GCTGGATGGG CCATGCTGGA AGCACTTTTC CTTTCGCATG  1140

TGTTTCCTCG ATACCGCTTC TGCTTTTATG GATATGTTCT ATGGCTTTGC TGGTGTACTA  1200

TGTACCTTAC CCACCACTAC TTTGTAGATT TGGTCGGCGG TATGTGTTTA GCTATTATAT  1260
```

```
GCTTCGTTTT TGCTCAAAAG CTACGCCTCC CACAGTTGCA AACTGGTAAA ATCCTTCGTT     1320

GGGAATACGA GTTTGTTATC CACGGTCATG GTCTTTCCGA AAAAACCAGC AACTCCTTGG     1380

CTCGTACCGG CAGCCCATAC TTACTTGGAA GGGATTCTTT TACTCAAAAC CCTAATGCAG     1440

TAGCCTTCAT GAGTGGTCTT AACAATATGG AACTTGCTAA CACCGATCAT GAATGGTCCG     1500

TGGGTTCATC ATCACCTGAG CCGTTACCTA GTCCTGCTGC TGATTTGATT GATCGTCCTG     1560

CCAGTACCAC TTCCTCCATC TTTGATGCAA GTCATCTTCC TTAAATCAAC GTGCTTTAAG     1620

AATATATTTC CAAAAGCTAC ATGATACATT GACTAGAATC GGTTTGATTC ATAGTGGTAT     1680

TGGAATGATG TTGTTCATTG TGTTTTTTAA CTGTTAATCT GACATCCATT GAGTCATTCT     1740

TTACAATTTG TAAAATTAAT TTGTATCACT AATTTTGAAG GAAGCTATTT TGGTATTAAT     1800

ACCGCTTTTG GTCTCCACTT CCTTTTCGAA ACTCTTAACA GCGATTAGGC CGGGTATCTT     1860

CCAGTGTGAT GTATAGGTAT TTGTCGTTTT TTTATCATTT CCGTTAATAA AGAACTCTTT     1920

TATCCAGCTT CTTACACTGT CAACTGTTGT GAAAGGAACA CATTTAGAAT TCATTTTCC      1980

TTATTTGTTG TGATTTAAAT CGTTTGACAT AATTTTAAAT TTGGTTTGAA ATGTGTGTGA     2040

GAAGGCTTGT TTTATTCATT TAGTTTATTG CTTGTTTGCA CGAAAATCCA GAACGGAGCA     2100

TTAATGTAAT CCTTTTTTAT TCTGTAAAGC GTTTTTATAC AAATGTTGGT TATACGTTTC     2160

TAAAATAAGA ATATTGTTAT AATAATATAG TTTTTTCTAT CATTTGTTAC ACACACTAAA     2220

GAGACATTAA GGATAAGCAA ATGTGTTAAA ATGATAATAT ATTTTGGAAA CATTTATAAA     2280

GAAATTAAGC AGCTTTGACT AACTACATTT TTGTTTTTTT CCTAAGCAAA ACTGTATAGT     2340

TATACACGCG AGCTGTATTC ACTTCCATTG TAGTGACTTG AGCTC                    2385
```

(2) INFORMATION FOR SEQ ID NO:18:

(i) SEQUENCE CHARACTERISTICS:
  (A) LENGTH: 422 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:18:

```
Met Ser Ala Leu Ser Thr Leu Lys Lys Arg Leu Ala Ala Cys Asn
 1               5                  10                  15

Arg Ala Ser Gln Tyr Lys Leu Glu Thr Ser Leu Asn Pro Met Pro
                20                  25                  30

Thr Phe Arg Leu Leu Arg Asn Thr Lys Trp Ser Trp Thr His Leu
                35                  40                  45

Gln Tyr Val Phe Leu Ala Gly Asn Leu Ile Phe Ala Cys Ile Val
                50                  55                  60

Ile Glu Ser Pro Gly Phe Trp Gly Lys Phe Gly Ile Ala Cys Leu
                65                  70                  75

Leu Ala Ile Ala Leu Thr Val Pro Leu Thr Arg Gln Ile Phe Phe
                80                  85                  90

Pro Ala Ile Val Ile Ile Thr Trp Ala Ile Leu Phe Tyr Ser Cys
                95                 100                 105

Arg Phe Ile Pro Glu Arg Trp Arg Pro Ile Trp Val Arg Val
               110                 115                 120

Leu Pro Thr Leu Glu Asn Ile Leu Tyr Gly Ser Asn Leu Ser Ser
               125                 130                 135
```

```
Leu Leu Ser Lys Thr Thr His Ser Ile Leu Asp Ile Leu Ala Trp
            140                 145                 150

Val Pro Tyr Gly Val Met His Tyr Ser Ala Pro Phe Ile Ile Ser
            155                 160                 165

Phe Ile Leu Phe Ile Phe Ala Pro Pro Gly Thr Leu Pro Val Trp
            170                 175                 180

Ala Arg Thr Phe Gly Tyr Met Asn Leu Phe Gly Val Leu Ile Gln
            185                 190                 195

Met Ala Phe Pro Cys Ser Pro Pro Trp Tyr Glu Asn Met Tyr Gly
            200                 205                 210

Leu Glu Pro Ala Thr Tyr Ala Val Arg Gly Ser Pro Gly Gly Leu
            215                 220                 225

Ala Arg Ile Asp Ala Leu Phe Gly Thr Ser Ile Tyr Thr Asp Gly
            230                 235                 240

Phe Ser Asn Ser Pro Val Val Phe Gly Ala Phe Pro Ser Leu His
            245                 250                 255

Ala Gly Trp Ala Met Leu Glu Ala Leu Phe Leu Ser His Val Phe
            260                 265                 270

Pro Arg Tyr Arg Phe Cys Phe Tyr Gly Tyr Val Leu Trp Leu Cys
            275                 280                 285

Trp Cys Thr Met Tyr Leu Thr His His Tyr Phe Val Asp Leu Val
            290                 295                 300

Gly Gly Met Cys Leu Ala Ile Ile Cys Phe Val Phe Ala Gln Lys
            305                 310                 315

Leu Arg Leu Pro Gln Leu Gln Thr Gly Lys Ile Leu Arg Trp Glu
            320                 325                 330

Tyr Glu Phe Val Ile His Gly His Gly Leu Ser Glu Lys Thr Ser
            335                 340                 345

Asn Ser Leu Ala Arg Thr Gly Ser Pro Tyr Leu Leu Gly Arg Asp
            350                 355                 360

Ser Phe Thr Gln Asn Pro Asn Ala Val Ala Phe Met Ser Gly Leu
            365                 370                 375

Asn Asn Met Glu Leu Ala Asn Thr Asp His Glu Trp Ser Val Gly
            380                 385                 390

Ser Ser Ser Pro Glu Pro Leu Pro Ser Pro Ala Ala Asp Leu Ile
            395                 400                 405

Asp Arg Pro Ala Ser Thr Thr Ser Ser Ile Phe Asp Ala Ser His
            410                 415                 420

Leu Pro (2) INFORMATION FOR SEQ ID NO:19:

(i) SEQUENCE CHARACTERISTICS:
        (A) LENGTH:  2340 base pairs
        (B) TYPE:  nucleic acid
        (C) STRANDEDNESS:  double
        (D) TOPOLOGY:  linear (ii) MOLECULE TYPE: genomic DNA (xi) SEQUENCE DESCRIPTION: SEQ ID NO:19:

TTTCTTTCTG TCAAAGAATA ATAAAGTGCC CATCAGTGTT CATATTTGTT ACAAAGTGGT     60

TTTCTGATTT GGTACTACTG CAGAGGCGTA TTTTTTGCTT CAGTTACCAT AGCGTAAGAA    120

CACTAGCGAC TTTTGTTCGT GAACCAACAG AGTAGGATTT CTACTGCTAC ATCTCTTAGG    180

TAGTTGGTTA GTCCGATCGC TCACTTTTGG TTGTTGTTAA GTACTTCATA AGTTTATCCT    240
```

```
TTTCCTTTTT CACACTGAGC TACTTTGGGT ATAGCTTTTG GCCCAAGGAT CTTTGAATTT      300

TCTCCAAAAG TACTTTATTT TATATCCTAC AGGTTGCGGT TTTCATATTT TAAAAAGCTT      360

TTTAATCATT CCTTTGCGTA TGGCAAACCC TTTTTCGAGA TGGTTTCTAT CAGAGAGACC      420

TCCAAACTGC CATGTAGCCG ATTTAGAAAC AAGTTTAGAT CCCCATCAAA CGTTGTTGAA      480

GGTGCAAAAA TACAAACCCG CTTTAAGCGA CTGGGTGCAT TACATCTTCT TGGGATCCAT      540

CATGCTGTTT GTGTTCATTA CTAATCCCGC ACCTTGGATC TTCAAGATCC TTTTTTATTG      600

TTTCTTGGGC ACTTTATTCA TCATTCCAGC TACGTCACAG TTTTTCTTCA ATGCCTTGCC      660

CATCCTAACA TGGGTGGCGC TGTATTTCAC TTCATCGTAC TTTCCAGATG ACCGCAGGCC      720

TCCTATTACT GTCAAAGTGT TACCAGCGGT GGAAACAATT TTATACGGCG ACAATTTAAG      780

TGATATTCTT GCAACATCGA CGAATTCCTT TTTGGACATT TTAGCATGGT TACCGTACGG      840

ACTATTTCAT TATGGGCCCC CATTTGTCGT TGCTGCCATC TTATTCGTAT TTGGTCCACC      900

AACTGTTTTG CAAGGTTATG CTTTTGCATT TGGTTATATG AACCTGTTTG GTGTTATCAT      960

GCAAAATGTC TTTCCAGCCG CTCCCCCATG GTATAAAATT CTCTATGGAT TGCAATCAGC     1020

CAACTATGAT ATGCATGGCT CGCCTGGTGG ATTAGCTAGA ATTGATAAGC TACTCGGTAT     1080

TAATATGTAT ACTACAGCTT TTTCAAATTC CTCCGTCATT TTCGGTGCTT TTCCTTCACT     1140

GCATTCCGGG TGTGCTACTA TGGAAGCCCT GTTTTTCTGT TATTGTTTTC CAAAATTGAA     1200

GCCCTTGTTT ATTGCTTATG TTTGCTGGTT ATGGTGGTCA ACTATGTATC TGACACACCA     1260

TTATTTTGTA GACCTTATGG CAGGTTCTGT GCTGTCATAC GTTATTTTCC AGTACACAAA     1320

GTACACACAT TTACCAATTG TAGATACATC TCTTTTTTGC AGATGGTCAT ACACTTCAAT     1380

TGAGAAATAC GATATATCAA AGAGTGATCC ATTGGCTGCA GATTCAAACG ATATCGAAAG     1440

TGTCCCTTTG TCCAACTTGG AACTTGACTT TGATCTTAAT ATGACTGATG AACCCAGTGT     1500

AAGCCCTTCG TTATTTGATG GATCTACTTC TGTTTCTCGT TCGTCCGCCA CGTCTATAAC     1560

GTCACTAGGT GTAAAGAGGG CTTAATGAGT ATTTTATCTG CAATTACGGA TACGGTTGGT     1620

CTTATGTAGA TACATATAAA TATATATCTT TTTCTTTCTT TTTCTTAGTC AGGATTGTCG     1680

TTTAGCATAA TATACATGTA GTTTATTTAA TCACATACCA CTGATTATCT TTAGAATTTT     1740

ATAAATTTTT GAAATAAATG GGTGGCTTTT AATGGTGTCT ATGTTAAGTG AGGCTTTTAG     1800

AATGCTCTTC CTGCTTTGTT TATTATATGT GTATGAAAGA TATGTATGTA TTTACATGTG     1860

TTTGTAGCGT CCCCAGTCAA AACCTGTGCG CTATACCTAA ATGGATTGAT AATCTTCATT     1920

CACTAATTCT AAAATAGACT TCTTCCCCAA AGAACGGTGT AACGATGAGG CTCTATCCAG     1980

CTGCTTATCT AAATCAACTT TAACGATGGA TGATCTTATG ACACGGGAT CTTTCTTTAA      2040

AGTTCTTAGA ATTTCAGACT GTACCGCAGC TGATGAATCA AACAGCATTA AAAAGTGATA     2100

TGCTCGAAAA TGTTTTTCCT GGTCTTTCTT CATTATTTTA GGAAGATACC TTATGCCCAT     2160

GGGTACAATG TCCCTCACCA CACCTCTGTT TGAATAATC AGTTTCCCGA TTGTGGAAGA      2220

CAATTCTTTT GCTTCCAACT TGGCGCATT GGAGTTGGTT ATGCGAACAA GTCCGATCAG      2280

CTCATAAAGC ATCTTAGTGA AAAGGGTGGT TTTGCGTTAT TCTTTCCTCT GTTGAAGCTT     2340
```

(2) INFORMATION FOR SEQ ID NO:20:

(i) SEQUENCE CHARACTERISTICS:
        (A) LENGTH: 401 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                  100                 105

Ser Tyr Phe Pro Asp Asp Arg Arg Pro Pro Ile Thr Val Lys Val
                110                 115                 120

Leu Pro Ala Val Glu Thr Ile Leu Tyr Gly Asp Asn Leu Ser Asp
                125                 130                 135

Ile Leu Ala Thr Ser Thr Asn Ser Phe Leu Asp Ile Leu Ala Trp
                140                 145                 150

Leu Pro Tyr Gly Leu Phe His Tyr Gly Ala Pro Phe Val Val Ala
                155                 160                 165

Ala Ile Leu Phe Val Phe Gly Pro Pro Thr Val Leu Gln Gly Tyr
                170                 175                 180

Ala Phe Ala Phe Gly Tyr Met Asn Leu Phe Gly Val Ile Met Gln
                185                 190                 195

Asn Val Phe Pro Ala Ala Pro Pro Trp Tyr Lys Ile Leu Tyr Gly
                200                 205                 210

Leu Gln Ser Ala Asn Tyr Asp Met His Gly Ser Pro Gly Gly Leu
                215                 220                 225

Ala Arg Ile Asp Lys Leu Leu Gly Ile Asn Met Tyr Thr Thr Ala
                230                 235                 240

Phe Ser Asn Ser Ser Val Ile Phe Gly Ala Phe Pro Ser Leu His
                245                 250                 255

Ser Gly Cys Ala Thr Met Glu Ala Leu Phe Phe Cys Tyr Cys Phe
                260                 265                 270

Pro Lys Leu Lys Pro Leu Phe Ile Ala Tyr Val Cys Trp Leu Trp
                275                 280                 285

Trp Ser Thr Met Tyr Leu Thr His His Tyr Phe Val Asp Leu Met
                290                 295                 300

Ala Gly Ser Val Leu Ser Tyr Val Ile Phe Gln Tyr Thr Lys Tyr
                305                 310                 315

Thr His Leu Pro Ile Val Asp Thr Ser Leu Phe Cys Arg Trp Ser
                320                 325                 330

Tyr Thr Ser Ile Glu Lys Tyr Asp Ile Ser Lys Ser Asp Pro Leu
                335                 340                 345

Ala Ala Asp Ser Asn Asp Ile Glu Ser Val Pro Leu Ser Asn Leu
                350                 355                 360

Glu Leu Asp Phe Asp Leu Asn Met Thr Asp Glu Pro Ser Val Ser
                365                 370                 375
```

Pro Ser Leu Phe Asp Gly Ser Thr Ser Val Ser Arg Ser Ser Ala
            380                 385                 390

Thr Ser Ile Thr Ser Leu Gly Val Lys Arg Ala
            395                 400

(2) INFORMATION FOR SEQ ID NO:21:

(i) SEQUENCE CHARACTERISTICS:
        (A) LENGTH: 2340 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:21:

```
TTTCTTTCTG TCAAAGAATA ATAAAGTGCC CATCAGTGTT CATATTTGTT ACAAAGTGGT     60

TTTCTGATTT GGTACTACTG CAGAGGCGTA TTTTTTGCTT CAGTTACCAT AGCGTAAGAA    120

CACTAGCGAC TTTTGTTCGT GAACCAACAG AGTAGGATTT CTACTGCTAC ATCTCTTAGG    180

TAGTTGGTTA GTCCGATCGC TCACTTTTGG TTGTTGTTAA GTACTTCATA AGTTTATCCT    240

TTTCCTTTTT CACACTGAGC TACTTTGGGT ATAGCTTTTG GCCCAAGGAT CTTTGAATTT    300

TCTCCAAAAG TACTTTATTT TATATCCTAC AGGTTGCGGT TTTCATATTT TAAAAAGCTT    360

TTTAATCATT CCTTTGCGTA TGGCAAACCC TTTTTCGAGA TGGTTTCTAT CAGAGAGACC    420

TCCAAACTGC CATGTAGCCG ATTTAGAAAC AAGTTTAGAT CCCCATCAAA CGTTGTTGAA    480

GGTGCAAAAA TACAAACCCG CTTTAAGCGA CTGGGTGCAT ACATCTTCT TGGGATCCAT     540

CATGCTGTTT GTGTTCATTA CTAATCCCGC ACCTTGGATC TTCAAGATCC TTTTTTATTG    600

TTTCTTGGGC ACTTTATTCA TCATTCCAGC TACGTCACAG TTTTTCTTCA ATGCCTTGCC    660

CATCCTAACA TGGGTGGCGC TGTATTTCAC TTCATCGTAC TTTCCAGATG ACCGCAGGCC    720

TCCTATTACT GTCAAAGTGT TACCAGCGGT GGAAACAATT TTATACGGCG ACAATTTAAG    780

TGATATTCTT GCAACATCGA CGAATTCCTT TTTGGACATT TTAGCATGGT TACCGTACGG    840

ACTATTTCAT TTTGGGGCCC CATTTGTCGT TGCTGCCATC TTATTCGTAT TTGGTCCACC    900

AACTGTTTTG CAAGGTTATG CTTTTGCATT TGGTTATATG AACCTGTTTG GTGTTATCAT    960

GCAAAATGTC TTTCCAGCCG CTCCCCCATG GTATAAAATT CTCTATGGAT GCAATCAGC   1020

CAACTATGAT ATGCATGGCT CGCCTGGTGG ATTAGCTAGA ATTGATAAGC TACTCGGTAT   1080

TAATATGTAT ACTACAGCTT TTTCAAATTC CTCCGTCATT TTCGGTGCTT TTCCTTCACT   1140

GCATTCCGGG TGTGCTACTA TGGAAGCCCT GTTTTTCTGT TATTGTTTTC CAAAATTGAA   1200

GCCCTTGTTT ATTGCTTATG TTTGCTGGTT ATGGTGGTCA ACTATGTATC TGACACACCA   1260

TTATTTGTA GACCTTATGG CAGGTTCTGT GCTGTCATAC GTTATTTTCC AGTACACAAA    1320

GTACACACAT TTACCAATTG TAGATACATC TCTTTTTTGC AGATGGTCAT ACACTTCAAT   1380

TGAGAAATAC GATATATCAA AGAGTGATCC ATTGGCTGCA GATTCAAACG ATATCGAAAG   1440

TGTCCCTTTG TCCAACTTGG AACTTGACTT TGATCTTAAT ATGACTGATG AACCCAGTGT   1500

AAGCCCTTCG TTATTTGATG GATCTACTTC TGTTTCTCGT TCGTCCGCCA CGTCTATAAC   1560

GTCACTAGGT GTAAGAGGG CTTAATGAGT ATTTTATCTG CAATTACGGA TACGGTTGGT    1620

CTTATGTAGA TACATATAAA TATATATCTT TTTCTTTCTT TTTCTTAGTC AGGATTGTCG   1680

TTTAGCATAA TATACATGTA GTTTATTTAA TCACATACCA CTGATTATCT TTAGAATTTT   1740

ATAAATTTTT GAAATAAATG GGTGGCTTTT AATGGTGTCT ATGTTAAGTG AGGCTTTTAG   1800
```

```
AATGCTCTTC CTGCTTTGTT TATTATATGT GTATGAAAGA TATGTATGTA TTTACATGTG    1860

TTTGTAGCGT CCCCAGTCAA AACCTGTGCG CTATACCTAA ATGGATTGAT AATCTTCATT    1920

CACTAATTCT AAAATAGACT TCTTCCCCAA AGAACGGTGT AACGATGAGG CTCTATCCAG    1980

CTGCTTATCT AAATCAACTT TAACGATGGA TGATCTTATG ACACGGGGAT CTTTCTTTAA    2040

AGTTCTTAGA ATTTCAGACT GTACCGCAGC TGATGAATCA AACAGCATTA AAAAGTGATA    2100

TGCTCGAAAA TGTTTTTCCT GGTCTTTCTT CATTATTTTA GGAAGATACC TTATGCCCAT    2160

GGGTACAATG TCCCTCACCA CACCTCTGTT TTGAATAATC AGTTTCCCGA TTGTGGAAGA    2220

CAATTCTTTT GCTTCCAACT TTGGCGCATT GGAGTTGGTT ATGCGAACAA GTCCGATCAG    2280

CTCATAAAGC ATCTTAGTGA AAAGGGTGGT TTTGCGTTAT TCTTTCCTCT GTTGAAGCTT    2340
```

(2) INFORMATION FOR SEQ ID NO:22:

(i) SEQUENCE CHARACTERISTICS:
        (A) LENGTH: 401 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                 100                 105

Ser Tyr Phe Pro Asp Asp Arg Arg Pro Pro Ile Thr Val Lys Val
               110                 115                 120

Leu Pro Ala Val Glu Thr Ile Leu Tyr Gly Asp Asn Leu Ser Asp
               125                 130                 135

Ile Leu Ala Thr Ser Thr Asn Ser Phe Leu Asp Ile Leu Ala Trp
               140                 145                 150

Leu Pro Tyr Gly Leu Phe His Phe Gly Ala Pro Phe Val Val Ala
               155                 160                 165

Ala Ile Leu Phe Val Phe Gly Pro Pro Thr Val Leu Gln Gly Tyr
               170                 175                 180

Ala Phe Ala Phe Gly Tyr Met Asn Leu Phe Gly Val Ile Met Gln
               185                 190                 195

Asn Val Phe Pro Ala Ala Pro Pro Trp Tyr Lys Ile Leu Tyr Gly
               200                 205                 210

Leu Gln Ser Ala Asn Tyr Asp Met His Gly Ser Pro Gly Gly Leu
               215                 220                 225

Ala Arg Ile Asp Lys Leu Leu Gly Ile Asn Met Tyr Thr Thr Ala
               230                 235                 240
```

```
Phe Ser Asn Ser Ser Val Ile Phe Gly Ala Phe Pro Ser Leu His
                245                 250                 255

Ser Gly Cys Ala Thr Met Glu Ala Leu Phe Phe Cys Tyr Cys Phe
            260                 265                 270

Pro Lys Leu Lys Pro Leu Phe Ile Ala Tyr Val Cys Trp Leu Trp
        275                 280                 285

Trp Ser Thr Met Tyr Leu Thr His His Tyr Phe Val Asp Leu Met
    290                 295                 300

Ala Gly Ser Val Leu Ser Tyr Val Ile Phe Gln Tyr Thr Lys Tyr
305                 310                 315

Thr His Leu Pro Ile Val Asp Thr Ser Leu Phe Cys Arg Trp Ser
                320                 325                 330

Tyr Thr Ser Ile Glu Lys Tyr Asp Ile Ser Lys Ser Asp Pro Leu
            335                 340                 345

Ala Ala Asp Ser Asn Asp Ile Glu Ser Val Pro Leu Ser Asn Leu
        350                 355                 360

Glu Leu Asp Phe Asp Leu Asn Met Thr Asp Glu Pro Ser Val Ser
    365                 370                 375

Pro Ser Leu Phe Asp Gly Ser Thr Ser Val Ser Arg Ser Ser Ala
380                 385                 390

Thr Ser Ile Thr Ser Leu Gly Val Lys Arg Ala
                395                 400

(2) INFORMATION FOR SEQ ID NO:23:

(i) SEQUENCE CHARACTERISTICS:
        (A) LENGTH: 5340 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:23:

AGCGCTTCTA TTTTCCTCCC CACCGCGAGG CGGAAATGGC ACATTTTTTT TCTTTTGCTT      60

CTGTGCTTTT GCTGTAATTT TTGGCATGTG CTATTGTATG AAGATAACGC GTGGTTCCGT     120

GGAAATAGCC GGAAATTTTG CCGGGAATAT GACGGACATG ATTTAACACC CGTGGAAATG     180

AAAAAAGCCA AGGTAAGAAA GTGGCAATAT TTTTCCTACA AATAGATCTG CTGTCCCTTA     240

GATGATTACC ATACATATAT ATATTTATTA CACACATCTG TCAGAGGTAG CTAGCGAAGG     300

TGTCACTGAA ATATTTTTTG TTCCAGTTAG TATAAATACG GAGGTAGAAC AGCTCTCCGC     360

GTGTATATCT TTTTTTGCGC TATACAAGAA CAGGAAGAAC GCATTTCCAT ACCTTTTTCT     420

CCTTACAGGT GCCCTCTGAG TAGTGTCACG AACGAGGAAA AAGATTAATA TTACTGTTTT     480

TATATTCAAA AAGAGTAAAG CCGTTGCTAT ATACGAATAT GACGATTACC GTGGGGGATG     540

CAGTTTCGGA GACGGAGCTG GAAAACAAAA GTCAAACGT GGTACTATCT CCCAAGGCAT      600

CTGCTTCTTC AGACATAAGC ACAGATGTTG ATAAAGCACA ATCGTCTTCT TGGGATGACA     660

AATCTTTGCT GCCTACAGGT GAATATATTG TGGACAGAAA TAAGCCCCAA ACCTACTTGA     720

ATAGCGATGA TATCGAAAAA GTGACAGAAT CTGATATTTT CCCTCAGAAA CGTCTGTTTT     780

CATTCTTGCA CTCTAAGAAA ATTCCAGAAG TACCACAAAC CGATGACGAG AGGAAGATAT     840

ATCCTCTGTT CCATACAAAT ATTATCTCTA ACATGTTTTT TTGGTGGGTT CTACCCATCC     900

TGCGAGTTGG TTATAAGAGA ACGATACAGC CGAACGATCT CTTCAAAATG GATCCGAGGA     960
```

```
                                          -continued

TGTCTATAGA GACCCTTTAT GACGACTTTG AAAAAAACAT GATTTACTAT TTTGAGAAGA       1020

CGAGGAAAAA ATACCGTAAA AGACATCCAG AAGCGACAGA AGAAGAGGTT ATGGAAAATG       1080

CCAAACTACC TAAACATACA GTTCTGAGAG CTTTATTATT CACTTTTAAG AAACAGTACT       1140

TCATGTCGAT AGTGTTTGCA ATTCTCGCTA ATTGTACATC CGGTTTTAAC CCCATGATTA       1200

CCAAGAGGCT AATTGAGTTT GTCGAAGAAA AGGCTATTTT TCATAGCATG CATGTTAACA       1260

AAGGTATTGG TTACGCTATT GGTGCATGTT TGATGATGTT CGTTAACGGG TTGACGTTCA       1320

ATCATTTCTT TCATACATCC CAACTGACTG GTGTGCAAGC TAAGTCTATT CTTACTAAAG       1380

CTGCCATGAA GAAAATGTTT AATGCATCTA ATTATGCGAG ACATTGTTTT CCTAACGGTA       1440

AAGTGACTTC TTTTGTAACA ACAGATCTCG CTAGAATTGA ATTTGCCTTA TCTTTTCAGC       1500

CGTTTTTGGC TGGGTTCCCT GCAATTTTGG CTATTTGCAT TGTTTTATTG ATCGTTAACC       1560

TTGGACCCAT TGCCTTAGTT GGGATTGGTA TTTTTTTCGG TGGGTTTTTC ATATCCTTAT       1620

TTGCATTTAA GTTAATTCTG GCTTTAGAA TTGCTGCGAA CATCTTCACT GATGCTAGAG        1680

TTACCATGAT GAGAGAAGTG CTGAATAATA TAAAAATGAT TAAATATTAT ACGTGGGAGG       1740

ATGCGTATGA AAAAAATATT CAAGATATTA GGACCAAAGA GATTTCTAAA GTTAGAAAAA       1800

TGCAACTATC AAGAAATTTC TTGATTGCTA TGGCCATGTC TTTGCCTAGT ATTGCTTCAT       1860

TGGTCACTTT CCTTGCAATG TACAAAGTTA ATAAAGGAGG CAGGCAACCT GGTAATATTT       1920

TTGCCTCTTT ATCTTTATTT CAGGTCTTGA GTTTGCAAAT GTTTTTCTTA CCTATTGCTA       1980

TTGGTACTGG AATTGACATG ATCATTGGAT TGGGCCGTTT GCAAAGCTTA TTGGAGGCTC       2040

CAGAAGATGA TCCAAATCAG ATGATTGAAA TGAAGCCCTC TCCTGGCTTT GATCCAAAAT       2100

TGGCTCTAAA AATGACACAT TGCTCATTTG AGTGGGAAGA TTATGAATTA AACGACGCTA       2160

TTGAAGAAGC AAAAGGAGAA GCTAAAGATG AAGGTAAAAA GAACAAAAAA AAGCGTAAGG       2220

ATACATGGG  TAAGCCATCT GCAAGTACTA ATAAGGCGAA AAGATTGGAC AATATGTTGA       2280

AAGACAGAGA CGGCCCGGAA GATTTAGAAA AAACTTCGTT TAGGGGTTTC AAGGACTTGA       2340

ACTTCGATAT TAAAAAGGGC GAATTTATTA TGATTACGGG ACCTATTGGT ACTGGTAAAT       2400

CTTCATTATT GAATGCGATG GCAGGATCAA TGAGAAAAAT TGATGGTAAG GTTGAAGTCA       2460

ACGGGGACTT ATTAATGTGT GGTTATCCAT GGATTCAAAA TGCATCTGTA AGAGATAACA       2520

TCATATTCGG TTCACCATTC AATAAAGAAA AGTATGATGA AGTAGTTCGT GTTTGCTCTT       2580

TGAAAGCTGA TCTGGATATT TTACCGGCAG GCGATATGAC CGAAATTGGG GAACGTGGTA       2640

TTACTTTATC TGGTGGTCAA AAGGCACGTA TCAATTTAGC CAGGTCTGTT TATAAGAAGA       2700

AGGATATTTA TGTATTCGAC GATGTCCTAA GTGCTGTCGA TTCTCGTGTT GGTAAACACA       2760

TCATGGATGA ATGTCTAACC GGAATGCTTG CTAATAAAAC CAGAATTTTA GCAACGCATC       2820

AGTTGTCACT GATTGAGAGA GCTTCTAGAG TCATCGTTTT AGGTACTGAT GGCCAAGTCG       2880

ATATTGGTAC TGTTGATGAG CTAAAAGCTC GTAATCAAAC TTTGATAAAT CTTTTACAAT       2940

TCTCTTCTCA AAATTCGGAG AAAGAGGATG AAGAACAGGA AGCGGTTGTT TCCGGTGAAT       3000

TGGGACAACT AAAATATGAA CCAGAGGTAA AGGAATTGAC TGAACTGAAG AAAAAGGCTA       3060

CAGAAATGTC ACAAACTGCA AATAGTGGTA AAATTGTAGC GGATGGTCAT ACTAGTAGTA       3120

AAGAAGAAAG AGCAGTCAAT AGTATCAGTC TGAAAATATA CCGTGAATAC ATTAAAGCTG       3180

CAGTAGGTAA GTGGGGTTTT ATCGCACTAC CGTTGTATGC AATTTTAGTC GTTGGAACCA       3240

CATTCTGCTC ACTTTTTTCT TCCGTTTGGT TATCTTACTG GACTGAGAAT AAATTCAAAA       3300

ACAGACCACC CAGTTTTTAT ATGGGTCTTT ACTCCTTCTT TGTGTTTGCT GCTTTCATAT       3360
```

```
TCATGAATGG CCAGTTCACC ATACTTTGCG CAATGGGTAT TATGGCATCG AAATGGTTAA    3420

ATTTGAGGGC TGTGAAAAGA ATTTTACACA CTCCAATGTC ATACATAGAT ACCACACCTT    3480

TGGGACGTAT TCTGAACAGA TTCACAAAAG ATACAGATAG CTTAGATAAT GAGTTAACCG    3540

AAAGTTTACG GTTGATGACA TCTCAATTTG CTAATATTGT AGGTGTTTGC GTCATGTGTA    3600

TTGTTTACTT GCCGTGGTTT GCTATCGCAA TTCCGTTTCT TTTGGTCATC TTTGTTCTGA    3660

TTGCTGATCA TTATCAGAGT TCTGGTAGAG AAATTAAAAG ACTTGAAGCT GTGCAACGGT    3720

CTTTTGTTTA CAATAATTTA AATGAAGTTT TGGGTGGGAT GGATACAATC AAAGCATACC    3780

GAAGTCAGGA ACGATTTTTG GCGAAATCAG ATTTTTTGAT CAACAAGATG AATGAGGCGG    3840

GATACCTTGT AGTTGTCCTG CAAAGATGGG TAGGTATTTT CCTTGATATG GTTGCTATCG    3900

CATTTGCACT AATTATTACG TTATTGTGTG TTACGAGAGC CTTTCCTATT TCCGCGGCTT    3960

CAGTTGGTGT TTTGTTGACT TATGTATTAC AATTGCCTGG TCTATTAAAT ACCATTTTAA    4020

GGGCAATGAC TCAAACAGAG AATGACATGA ATAGTGCCGA AGATTGGTA ACATATGCAA     4080

CTGAACTACC ACTAGAGGCA TCCTATAGAA AGCCCGAAAT GACACCTCCA GAGTCATGGC    4140

CCTCAATGGG CGAAATAATT TTTGAAAATG TTGATTTTGC CTATAGACCT GGTTTACCTA    4200

TAGTTTTAAA AAATCTTAAC TTGAATATCA AGAGTGGGGA AAAAATTGGT ATCTGTGGTC    4260

GTACAGGTGC TGGTAAGTCC ACTATTATGA GTGCCCTTTA CAGGTTGAAT GAATTGACCG    4320

CAGGTAAAAT TTTAATTGAC AATGTTGATA TAAGTCAGCT GGGACTTTTC GATTTAAGAA    4380

GAAAATTAGC CATCATTCCA CAAGATCCAG TATTATTTAG GGGTACGATT CGCAAGAACT    4440

TAGATCCATT TAATGAGCGT ACAGATGACG AATTATGGGA TGCATTGGTG AGAGGTGGTG    4500

CTATCGCCAA GGATGACTTG CCGGAAGTGA AATTGCAAAA ACCTGATGAA AATGGTACTC    4560

ATGGTAAAAT GCATAAGTTC CATTTAGATC AAGCAGTGGA AGAAGAGGGC TCCAATTTCT    4620

CCTTAGGTGA GAGACAACTA TTAGCATTAA CAAGGGCATT GGTCCGCCAA TCAAAAATAT    4680

TGATTTTGGA TGAGGCTACA TCCTCAGTGG ACTACGAAAC GGATGGCAAA ATCCAAACAC    4740

GTATTGTTGA GGAATTTGGA GATTGTACAA TTTTGTGTAT TGCTCACAGA CTGAAGACCA    4800

TTGTAAATTA TGATCGTATT CTTGTTTTAG AGAAGGGTGA AGTCGCAGAA TTCGATACAC    4860

CATGGACGTT GTTTAGTCAA GAAGATAGTA TTTTCAGAAG CATGTGTTCT AGATCTGGTA    4920

TTGTGGAAAA TGATTTCGAG AACAGAAGTT AATTTATATT ATTTGTTGCA TGATTTTTCT    4980

CTTTTATTTA TTTATATGTT GCCGATGGTA CAAATTAGTA CTAGAAAAGA AAACCCACTA    5040

CTATGACTTG CAGAAAAAGT TATGTGTGCC ATAGATAGAT ATAATTGCAT ACCCACATCG    5100

TATACTCAAA ATTCCGAAAA GAACATTTCA TTTTTTATGA GGCAAACTGA ACAACGCTTC    5160

GGTCCTTTTT TCATTCTAGA AATATATATT TATACATCAT TTTCAGAAGA TATTCAAAGA    5220

ACTTATTGGG ATGTCTATTT ACTGAATAAA GTATACACAA AAAACGAATT TAAAATGGAA    5280

GGCATAAATA GAAAACTTAG AAGTGAAAAT CCTAAAACCG AAGGATATTT CAAATACGTA    5340
```

(2) INFORMATION FOR SEQ ID NO:24:

(i) SEQUENCE CHARACTERISTICS:
        (A) LENGTH: 1477 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

-continued

```
Met Thr Ile Thr Val Gly Asp Ala Val Ser Glu Thr Glu Leu Glu
                  5                  10                  15
Asn Lys Ser Gln Asn Val Val Leu Ser Pro Lys Ala Ser Ala Ser
                 20                  25                  30
Ser Asp Ile Ser Thr Asp Val Asp Lys Asp Thr Ser Ser Ser Trp
                 35                  40                  45
Asp Asp Lys Ser Leu Leu Pro Thr Gly Glu Tyr Ile Val Asp Arg
                 50                  55                  60
Asn Lys Pro Gln Thr Tyr Leu Asn Ser Asp Asp Ile Glu Lys Val
                 65                  70                  75
Thr Glu Ser Asp Ile Phe Pro Gln Lys Arg Leu Phe Ser Phe Leu
                 80                  85                  90
His Ser Lys Lys Ile Pro Glu Val Pro Gln Thr Asp Asp Glu Arg
                 95                 100                 105
Lys Ile Tyr Pro Leu Phe His Thr Asn Ile Ile Ser Asn Met Phe
                110                 115                 120
Phe Trp Trp Val Leu Pro Ile Leu Arg Val Gly Tyr Lys Arg Thr
                125                 130                 135
Ile Gln Pro Asn Asp Leu Phe Lys Met Asp Pro Arg Met Ser Ile
                140                 145                 150
Glu Thr Leu Tyr Asp Asp Phe Glu Lys Asn Met Ile Tyr Tyr Phe
                155                 160                 165
Glu Lys Thr Arg Lys Lys Tyr Arg Lys Arg His Pro Glu Ala Thr
                170                 175                 180
Glu Glu Glu Val Met Glu Asn Ala Lys Leu Pro Lys His Thr Val
                185                 190                 195
Leu Arg Ala Leu Leu Phe Thr Phe Lys Lys Gln Tyr Phe Met Ser
                200                 205                 210
Ile Val Phe Ala Ile Leu Ala Asn Cys Thr Ser Gly Phe Asn Pro
                215                 220                 225
Met Ile Thr Lys Arg Leu Ile Glu Phe Val Glu Glu Lys Ala Ile
                230                 235                 240
Phe His Ser Met His Val Asn Lys Gly Ile Gly Tyr Ala Ile Gly
                245                 250                 255
Ala Cys Leu Met Met Phe Val Asn Gly Leu Thr Phe Asn His Phe
                260                 265                 270
Phe His Thr Ser Gln Leu Thr Gly Val Gln Ala Lys Ser Ile Leu
                275                 280                 285
Thr Lys Ala Ala Met Lys Lys Met Phe Asn Ala Ser Asn Tyr Ala
                290                 295                 300
Arg His Cys Phe Pro Asn Gly Lys Val Thr Ser Phe Val Thr Thr
                305                 310                 315
Asp Leu Ala Arg Ile Glu Phe Ala Leu Ser Phe Gln Pro Phe Leu
                320                 325                 330
Ala Gly Phe Pro Ala Ile Leu Ala Ile Cys Ile Val Leu Leu Ile
                335                 340                 345
Val Asn Leu Gly Pro Ile Ala Leu Val Gly Ile Gly Ile Phe Phe
                350                 355                 360
Gly Gly Phe Phe Ile Ser Leu Phe Ala Phe Lys Leu Ile Leu Gly
                365                 370                 375
Phe Arg Ile Ala Ala Asn Ile Phe Thr Asp Ala Arg Val Thr Met
                380                 385                 390
```

-continued

```
Met Arg Glu Val Leu Asn Asn Ile Lys Met Ile Lys Tyr Tyr Thr
            395                 400                 405

Trp Glu Asp Ala Tyr Glu Lys Asn Ile Gln Asp Ile Arg Thr Lys
            410                 415                 420

Glu Ile Ser Lys Val Arg Lys Met Gln Leu Ser Arg Asn Phe Leu
            425                 430                 435

Ile Ala Met Ala Met Ser Leu Pro Ser Ile Ala Ser Leu Val Thr
            440                 445                 450

Phe Leu Ala Met Tyr Lys Val Asn Lys Gly Gly Arg Gln Pro Gly
            455                 460                 465

Asn Ile Phe Ala Ser Leu Ser Leu Phe Gln Val Leu Ser Leu Gln
            470                 475                 480

Met Phe Phe Leu Pro Ile Ala Ile Gly Thr Gly Ile Asp Met Ile
            485                 490                 495

Ile Gly Leu Gly Arg Leu Gln Ser Leu Leu Glu Ala Pro Glu Asp
            500                 505                 510

Asp Pro Asn Gln Met Ile Glu Met Lys Pro Ser Pro Gly Phe Asp
            515                 520                 525

Pro Lys Leu Ala Leu Lys Met Thr His Cys Ser Phe Glu Trp Glu
            530                 535                 540

Asp Tyr Glu Leu Asn Asp Ala Ile Glu Glu Ala Lys Gly Glu Ala
            545                 550                 555

Lys Asp Glu Gly Lys Lys Asn Lys Lys Arg Lys Asp Thr Trp
            560                 565                 570

Gly Lys Pro Ser Ala Ser Thr Asn Lys Ala Lys Arg Leu Asp Asn
            575                 580                 585

Met Leu Lys Asp Arg Asp Gly Pro Glu Asp Leu Glu Lys Thr Ser
            590                 595                 600

Phe Arg Gly Phe Lys Asp Leu Asn Phe Asp Ile Lys Lys Gly Glu
            605                 610                 615

Phe Ile Met Ile Thr Gly Pro Ile Gly Thr Gly Lys Ser Ser Leu
            620                 625                 630

Leu Asn Ala Met Ala Gly Ser Met Arg Lys Ile Asp Gly Lys Val
            635                 640                 645

Glu Val Asn Gly Asp Leu Leu Met Cys Gly Tyr Pro Trp Ile Gln
            650                 655                 660

Asn Ala Ser Val Arg Asp Asn Ile Ile Phe Gly Ser Pro Phe Asn
            665                 670                 675

Lys Glu Lys Tyr Asp Glu Val Val Arg Val Cys Ser Leu Lys Ala
            680                 685                 690

Asp Leu Asp Ile Leu Pro Ala Gly Asp Met Thr Glu Ile Gly Glu
            695                 700                 705

Arg Gly Ile Thr Leu Ser Gly Gly Gln Lys Ala Arg Ile Asn Leu
            710                 715                 720

Ala Arg Ser Val Tyr Lys Lys Asp Ile Tyr Val Phe Asp Asp
            725                 730                 735

Val Leu Ser Ala Val Asp Ser Arg Val Gly Lys His Ile Met Asp
            740                 745                 750

Glu Cys Leu Thr Gly Met Leu Ala Asn Lys Thr Arg Ile Leu Ala
            755                 760                 765

Thr His Gln Leu Ser Leu Ile Glu Arg Ala Ser Arg Val Ile Val
            770                 775                 780

Leu Gly Thr Asp Gly Gln Val Asp Ile Gly Thr Val Asp Glu Leu
```

```
                    785                 790                 795
Lys Ala Arg Asn Gln Thr Leu Ile Asn Leu Leu Gln Phe Ser Ser
                800                 805                 810
Gln Asn Ser Glu Lys Glu Asp Glu Glu Gln Glu Ala Val Val Ser
                815                 820                 825
Gly Glu Leu Gly Gln Leu Lys Tyr Glu Pro Glu Val Lys Glu Leu
                830                 835                 840
Thr Glu Leu Lys Lys Lys Ala Thr Glu Met Ser Gln Thr Ala Asn
                845                 850                 855
Ser Gly Lys Ile Val Ala Asp Gly His Thr Ser Ser Lys Glu Glu
                860                 865                 870
Arg Ala Val Asn Ser Ile Ser Leu Lys Ile Tyr Arg Glu Tyr Ile
                875                 880                 885
Lys Ala Ala Val Gly Lys Trp Gly Phe Ile Ala Leu Pro Leu Tyr
                890                 895                 900
Ala Ile Leu Val Val Gly Thr Thr Phe Cys Ser Leu Phe Ser Ser
                905                 910                 915
Val Trp Leu Ser Tyr Trp Thr Glu Asn Lys Phe Lys Asn Arg Pro
                920                 925                 930
Pro Ser Phe Tyr Met Gly Leu Tyr Ser Phe Phe Val Phe Ala Ala
                935                 940                 945
Phe Ile Phe Met Asn Gly Gln Phe Thr Ile Leu Cys Ala Met Gly
                950                 955                 960
Ile Met Ala Ser Lys Trp Leu Asn Leu Arg Ala Val Lys Arg Ile
                965                 970                 975
Leu His Thr Pro Met Ser Tyr Ile Asp Thr Thr Pro Leu Gly Arg
                980                 985                 990
Ile Leu Asn Arg Phe Thr Lys Asp Thr Asp Ser Leu Asp Asn Glu
                995                 1000                1005
Leu Thr Glu Ser Leu Arg Leu Met Thr Ser Gln Phe Ala Asn Ile
                1010                1015                1020
Val Gly Val Cys Val Met Cys Ile Val Tyr Leu Pro Trp Phe Ala
                1025                1030                1035
Ile Ala Ile Pro Phe Leu Leu Val Ile Phe Val Leu Ile Ala Asp
                1040                1045                1050
His Tyr Gln Ser Ser Gly Arg Glu Ile Lys Arg Leu Glu Ala Val
                1055                1060                1065
Gln Arg Ser Phe Val Tyr Asn Asn Leu Asn Glu Val Leu Gly Gly
                1070                1075                1080
Met Asp Thr Ile Lys Ala Tyr Arg Ser Gln Glu Arg Phe Leu Ala
                1085                1090                1095
Lys Ser Asp Phe Leu Ile Asn Lys Met Asn Glu Ala Gly Tyr Leu
                1100                1105                1110
Val Val Val Leu Gln Arg Trp Val Gly Ile Phe Leu Asp Met Val
                1115                1120                1125
Ala Ile Ala Phe Ala Leu Ile Ile Thr Leu Leu Cys Val Thr Arg
                1130                1135                1140
Ala Phe Pro Ile Ser Ala Ala Ser Val Gly Val Leu Leu Thr Tyr
                1145                1150                1155
Val Leu Gln Leu Pro Gly Leu Leu Asn Thr Ile Leu Arg Ala Met
                1160                1165                1170
Thr Gln Thr Glu Asn Asp Met Asn Ser Ala Glu Arg Leu Val Thr
                1175                1180                1185
```

```
Tyr Ala Thr Glu Leu Pro Leu Glu Ala Ser Tyr Arg Lys Pro Glu
            1190                1195                1200

Met Thr Pro Pro Glu Ser Trp Pro Ser Met Gly Glu Ile Ile Phe
            1205                1210                1215

Glu Asn Val Asp Phe Ala Tyr Arg Pro Gly Leu Pro Ile Val Leu
            1220                1225                1230

Lys Asn Leu Asn Leu Asn Ile Lys Ser Gly Glu Lys Ile Gly Ile
            1235                1240                1245

Cys Gly Arg Thr Gly Ala Gly Lys Ser Thr Ile Met Ser Ala Leu
            1250                1255                1260

Tyr Arg Leu Asn Glu Leu Thr Ala Gly Lys Ile Leu Ile Asp Asn
            1265                1270                1275

Val Asp Ile Ser Gln Leu Gly Leu Phe Asp Leu Arg Arg Lys Leu
            1280                1285                1290

Ala Ile Ile Pro Gln Asp Pro Val Leu Phe Arg Gly Thr Ile Arg
            1295                1300                1305

Lys Asn Leu Asp Pro Phe Asn Glu Arg Thr Asp Asp Glu Leu Trp
            1310                1315                1320

Asp Ala Leu Val Arg Gly Gly Ala Ile Ala Lys Asp Asp Leu Pro
            1325                1330                1335

Glu Val Lys Leu Gln Lys Pro Asp Glu Asn Gly Thr His Gly Lys
            1340                1345                1350

Met His Lys Phe His Leu Asp Gln Ala Val Glu Glu Glu Gly Ser
            1355                1360                1365

Asn Phe Ser Leu Gly Glu Arg Gln Leu Leu Ala Leu Thr Arg Ala
            1370                1375                1380

Leu Val Arg Gln Ser Lys Ile Leu Ile Leu Asp Glu Ala Thr Ser
            1385                1390                1395

Ser Val Asp Tyr Glu Thr Asp Gly Lys Ile Gln Thr Arg Ile Val
            1400                1405                1410

Glu Glu Phe Gly Asp Cys Thr Ile Leu Cys Ile Ala His Arg Leu
            1415                1420                1425

Lys Thr Ile Val Asn Tyr Asp Arg Ile Leu Val Leu Glu Lys Gly
            1430                1435                1440

Glu Val Ala Glu Phe Asp Thr Pro Trp Thr Leu Phe Ser Gln Glu
            1445                1450                1455

Asp Ser Ile Phe Arg Ser Met Cys Ser Arg Ser Gly Ile Val Glu
            1460                1465                1470

Asn Asp Phe Glu Asn Arg Ser
            1475

(2) INFORMATION FOR SEQ ID NO:25:

(i) SEQUENCE CHARACTERISTICS:
        (A) LENGTH:  26 bases
        (B) TYPE:  nucleic acid
        (C) STRANDEDNESS:  single
        (D) TOPOLOGY:  linear (ii) MOLECULE TYPE: Other nucleic acid (synthetic DNA)

(xi) SEQUENCE DESCRIPTION: SEQ ID NO:25:

TTTGGTTAYA TGAAYYTNTT YGGNGT                                              26

(2) INFORMATION FOR SEQ ID NO:26:
```

(i) SEQUENCE CHARACTERISTICS:
    (A) LENGTH: 29 bases
    (B) TYPE: nucleic acid
    (C) STRANDEDNESS: single
    (D) TOPOLOGY: linear (ii) MOLECULE TYPE: Other nucleic acid (synthetic DNA)

(xi) SEQUENCE DESCRIPTION: SEQ ID NO:26:

TCTACAAART ARTGGTGNGT NARRTACAT    29

(2) INFORMATION FOR SEQ ID NO:27:

(i) SEQUENCE CHARACTERISTICS:
    (A) LENGTH: 2274 base pairs
    (B) TYPE: nucleic acid
    (C) STRANDEDNESS: double
    (D) TOPOLOGY: linear (ii) MOLECULE TYPE: genomic DNA (xi) SEQUENCE DESCRIPTION: SEQ ID NO:27:

```
TTATATATAT TATTGATTTG TTCCTGTTGT TATTTAGTTT AGAATCAGAC GACTACACCA      60
GAACCACAAT TCAACCAACA CTTATATAGA ACCTGGCTTG GAAAAAAGTA ACATTTATCA     120
TTCCTATACT TTTTTAGCAA ACATAATCCG TGTTTTACAT ATATTATTCA CCCAATATCA     180
TAACAAAAAC AAACTGAATA ATGGCGTCTT CTATTTTGCG TTCCAAAATA ATACAAAAAC     240
CGTACCAATT ATTCCACTAC TATTTTCTTC TGGAGAAGGC TCCTGGTTCT ACAGTTAGTG     300
ATTTGAATTT TGATACAAAC ATACAAACGA GTTTACGTAA ATTAAAGCAT CATCATTGGA     360
CGGTGGGAGA AATATTCCAT TATGGGTTTT TGGTTTCCAT ACTTTTTTTC GTGTTTGTGG     420
TTTTCCCAGC TTCATTTTTT ATAAAATTAC CAATAATCTT AGCATTTGCT ACTTGTTTTT     480
TAATACCCTT AACATCACAA TTTTTTCTTC CTGCCTTGCC CGTTTTCACT TGGTTGGCAT     540
TATATTTTAC GTGTGCTAAA ATACCTCAAG AATGGAAACC AGCTATCACA GTTAAAGTTT     600
TACCAGCTAT GGAAACAATT TTGTACGGCG ATAATTTATC AAATGTTTTG GCAACCATCA     660
CTACCGGAGT GTTAGATATA TTGGCATGGT TACCATATGG GATTATTCAT TTCAGTTTCC     720
CATTTGTACT TGCTGCTATT ATATTTTTAT TTGGGCCACC GACGGCATTA AGATCATTTG     780
GATTTGCCTT TGGTTATATG AACTTGCTTG GAGTCTTGAT TCAAATGGCA TTCCCAGCTG     840
CTCCTCCATG GTACAAAAAC TTGCACGGAT TAGAACCAGC TAATTATTCA ATGCACGGGT     900
CTCCTGGTGG ACTTGGAAGG ATAGATAAAT TGTTAGGTGT TGATATGTAT ACCACAGGGT     960
TTTCCAATTC ATCAATCATT TTTGGGGCAT TCCCATCGTT ACATTCAGGA TGTTGTATCA    1020
TGGAAGTGTT ATTTTTGTGT TGGTTGTTTC CACGATTCAA GTTTGTGTGG GTTACATACG    1080
CATCTTGGCT TTGGTGGAGC ACGATGTATT TGACCCATCA CTACTTTGTC GATTTGATTG    1140
GTGGAGCCAT GCTATCTTTG ACTGTTTTTG AGTTCACCAA ATATAAATAT TTGCCAAAAA    1200
ACAAAGAAGG CCTTTTCTGT CGTTGGTCAT ACACTGAAAT TGAAAAAATC GATATCCAAG    1260
AGATTGACCC TTTATCATAC AATTATATCC CTGTCAACAG CAATGATAAT GAAAGCAGAT    1320
TGTATACGAG AGTGTACCAA GAGTCTCAGG TTAGTCCCCC ACAGAGAGCT GAAACACCTG    1380
AAGCATTTGA GATGTCAAAT TTTTCTAGGT CTAGACAAAG CTCAAAGACT CAGGTTCCAT    1440
TGAGTAATCT TACTAACAAT GATCAAGTGT CTGGAATTAA CGAAGAGGAT GAAGAAGAAG    1500
AAGGCGATGA AATTTCATCG AGTACTCCTT CGGTGTTTGA AGACGAACCA CAGGGTAGCA    1560
CATATGCTGC ATCCTCAGCT ACATCAGTAG ATGATTTGGA TTCCAAAGAA AATTAGTAAA    1620
```

-continued

```
ATAACAGTTT CTATTAATTT CTTTATTTCC TCCTAATTAA TGATTTTATG CTCAATACCT    1680

ACACTATCTG TTTTTAATTT CCTACTTTTT TTTTATTATT GTTGAGTTCA TTTGCTGTTC    1740

ATTGAATATT TACAATTTTG CATTAATTAC CATCAATATA GAATGGGCAC AGTTTTTTA    1800

AGTTTTTTTG TTTTTGTGTT TGTCTTTCTT TTTTTACATT AATGTGTTTG GATTGTTTTA    1860

GGTTCCTTTA TCCCTTAGCC CCCTCAGAAT ACTATTTTAT CTAATTAATT TGTTTTTATT    1920

TTCTGATATT TACCAATTGC TTTTTCTTTT GGATATTTAT AATAGCATCC CCTAATAATT    1980

AATATACAAC TGTTTCATAT ATATACGTGT ATGTCCTGTA GTGGTGGAAA CTGGAGTCAA    2040

CATTTGTATT AATGTGTACA AGAAAGCAGT GTTAATGCTA CTATTATAAT TTTTGAGGTG    2100

CAAATCAAGA GGTTGGCAGC TTTCTTATGG CTATGACCGT GAATGAAGGC TTGTAAACCA    2160

CGTAATAAAC AAAAGCCAAC AAGTTTTTTT AGAGCCTTTA ACAACATACG CAATGAGAGT    2220

GATTGCAATA CTACAAGATA TAGCCCAAAA AATTGAATGC ATTTCAACAA CAAC          2274
```

(2) INFORMATION FOR SEQ ID NO:28:

(i) SEQUENCE CHARACTERISTICS:
        (A) LENGTH: 471 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Met Ala Ser Ser Ile Leu Arg Ser Lys Ile Ile Gln Lys Pro Tyr
                 5                  10                  15

Gln Leu Phe His Tyr Tyr Phe Leu Ser Glu Lys Ala Pro Gly Ser
                20                  25                  30

Thr Val Ser Asp Leu Asn Phe Asp Thr Asn Ile Gln Thr Ser Leu
                35                  40                  45

Arg Lys Leu Lys His His His Trp Thr Val Gly Glu Ile Phe His
                50                  55                  60

Tyr Gly Phe Leu Val Ser Ile Leu Phe Phe Val Phe Val Val Phe
                65                  70                  75

Pro Ala Ser Phe Phe Ile Lys Leu Pro Ile Ile Leu Ala Phe Ala
                80                  85                  90

Thr Cys Phe Leu Ile Pro Leu Thr Ser Gln Phe Phe Leu Pro Ala
                95                 100                 105

Leu Pro Val Phe Thr Trp Leu Ala Leu Tyr Phe Thr Cys Ala Lys
               110                 115                 120

Ile Pro Gln Glu Trp Lys Pro Ala Ile Thr Val Lys Val Leu Pro
               125                 130                 135

Ala Met Glu Thr Ile Leu Tyr Gly Asp Asn Leu Ser Asn Val Leu
               140                 145                 150

Ala Thr Ile Thr Thr Gly Val Leu Asp Ile Leu Ala Trp Leu Pro
               155                 160                 165

Tyr Gly Ile Ile His Phe Ser Phe Pro Phe Val Leu Ala Ala Ile
               170                 175                 180

Ile Phe Leu Phe Gly Pro Pro Thr Ala Leu Arg Ser Phe Gly Phe
               185                 190                 195

Ala Phe Gly Tyr Met Asn Leu Leu Gly Val Leu Ile Gln Met Ala
               200                 205                 210

Phe Pro Ala Ala Pro Pro Trp Tyr Lys Asn Leu His Gly Leu Glu
               215                 220                 225
```

```
Pro Ala Asn Tyr Ser Met His Gly Ser Pro Gly Gly Leu Gly Arg
            230                 235                 240

Ile Asp Lys Leu Leu Gly Val Asp Met Tyr Thr Thr Gly Phe Ser
            245                 250                 255

Asn Ser Ser Ile Ile Phe Gly Ala Phe Pro Ser Leu His Ser Gly
            260                 265                 270

Cys Cys Ile Met Glu Val Leu Phe Leu Cys Trp Leu Phe Pro Arg
            275                 280                 285

Phe Lys Phe Val Trp Val Thr Tyr Ala Ser Trp Leu Trp Trp Ser
            290                 295                 300

Thr Met Tyr Leu Thr His His Tyr Phe Val Asp Leu Ile Gly Gly
            305                 310                 315

Ala Met Leu Ser Leu Thr Val Phe Glu Phe Thr Lys Tyr Lys Tyr
            320                 325                 330

Leu Pro Lys Asn Lys Glu Gly Leu Phe Cys Arg Trp Ser Tyr Thr
            335                 340                 345

Glu Ile Glu Lys Ile Asp Ile Gln Glu Ile Asp Pro Leu Ser Tyr
            350                 355                 360

Asn Tyr Ile Pro Val Asn Ser Asn Asp Asn Glu Ser Arg Leu Tyr
            365                 370                 375

Thr Arg Val Tyr Gln Glu Ser Gln Val Ser Pro Pro Gln Arg Ala
            380                 385                 390

Glu Thr Pro Glu Ala Phe Glu Met Ser Asn Phe Ser Arg Ser Arg
            395                 400                 405

Gln Ser Ser Lys Thr Gln Val Pro Leu Ser Asn Leu Thr Asn Asn
            410                 415                 420

Asp Gln Val Ser Gly Ile Asn Glu Glu Asp Glu Glu Glu Glu Gly
            425                 430                 435

Asp Glu Ile Ser Ser Ser Thr Pro Ser Val Phe Glu Asp Glu Pro
            440                 445                 450

Gln Gly Ser Thr Tyr Ala Ala Ser Ser Ala Thr Ser Val Asp Asp
            455                 460                 465

Leu Asp Ser Lys Arg Asn
            470
```

(2) INFORMATION FOR SEQ ID NO:29:

(i) SEQUENCE CHARACTERISTICS:
        (A) LENGTH: 243 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:29:

```
TTTGAAAAAT TGAATTTTA AAATTAATCC AATGGAAAAA ATTGGTATTT GTGGAAGAAC    60

CGGTGCTGGT AAATCATCAA TTATGACAGC ATTATATCGA TTATCAGAAT TAGAACTGGG   120

GAAAATTATT ATTGATGATA TTGATATTTC AACTTTGGGT TTAAAAGATC TTCGATCAAA   180

ATTATCAATT ATTCCTCAAG ATCCAGTATT ATTCCGAGGT TCAATTCGGA AAAACTTGGA   240

TCC                                                                243
```

(2) INFORMATION FOR SEQ ID NO:30:

(i) SEQUENCE CHARACTERISTICS:

```
            (A) LENGTH:  80 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION: SEQ ID NO:30:

Leu Lys Asn Leu Asn Phe Lys Ile Asn Pro Met Glu Lys Ile Gly
            5                  10                  15

Ile Cys Gly Arg Thr Gly Ala Gly Lys Ser Ser Ile Met Thr Ala
        20                  25                  30

Leu Tyr Arg Leu Ser Glu Leu Glu Leu Gly Lys Ile Ile Ile Asp
        35                  40                  45

Asp Ile Asp Ile Ser Thr Leu Gly Leu Lys Asp Leu Arg Ser Lys
        50                  55                  60

Leu Ser Ile Ile Pro Gln Asp Pro Val Leu Phe Arg Gly Ser Ile
        65                  70                  75

Arg Lys Asn Leu Asp
        80

(2) INFORMATION FOR SEQ ID NO:31:

(i) SEQUENCE CHARACTERISTICS:
        (A) LENGTH:  1601 bases
        (B) TYPE:  nucleic acid
        (C) STRANDEDNESS:  double
        (D) TOPOLOGY:  linear (ii) MOLECULE TYPE:  genomic DNA (iv) ANTI-SENSE:  Yes (xi) SEQUENCE DESCRIPTION: SEQ ID NO:31:
```

| | | | | | |
|---|---|---|---|---|---|
| AGGAAGATGA | CTTGCATCAA | AGATGGAGGA | AGTGGTACTG | GCAGGACGAT | CAATCAAATC | 60 |
| AGCAGCAGGA | CTAGGTAACG | GCTCAGGTGA | TGATGAACCC | ACGGACCATT | CATGATCGGT | 120 |
| GTTAGCAAGT | TCCATATTGT | TAAGACCACT | CATGAAGGCT | ACTGCATTAG | GGTTTTGAGT | 180 |
| AAAAGAATCC | CTTCCAAGTA | AGTATGGGCT | GCCGGTACGA | GCCAAGGAGT | TGCTGGTTTT | 240 |
| TTCGGAAAGA | CCATGACCGT | GGATAACAAA | CTCGTATTCC | CAACGAAGGA | TTTTACCAGT | 300 |
| TTGCAACTGT | GGGAGGCGTA | GCTTTTGAGC | AAAAACGAAG | CATATAATAG | CTAAACACAT | 360 |
| ACCGCCGACC | AAATCTACAA | AGTAGTGGTG | GGTAAGGTAC | ATAGTACACC | AGCAAAGCCA | 420 |
| TAGAACATAT | CCATAAAAGC | AGAAGCGGTA | TCGAGGAAAC | ACATGCGAAA | GGAAAAGTGC | 480 |
| TTCCAGCATG | GCCCATCCAG | CGTGAAGAGA | TGGAAAGGCA | CCAAAAACAA | CCGGAGAGTT | 540 |
| AGAAAAACCA | TCAGTGTAAA | TGCTAGTGCC | GAAGAGAGCA | TCAATACGGG | CCAATCCACC | 600 |
| AGGAGAGCCA | CGTACTGCAT | ACGTGGCAGG | TTCTAAACCA | TACATATTTT | CATACCAAGG | 660 |
| AGGAGAACAG | GGGAAAGCCA | TTTGGATAAG | AACACCAAAT | AAATTCATAT | AACCAAAAGT | 720 |
| TCGAGCCCAA | ACTGGAAGAG | TTCCAGGAGG | TGCAAAGATG | AAAAGAATAA | ATGAAATGAT | 780 |
| AAAAGGAGCC | GAATAATGCA | TGACTCCATA | TGGAACCCAG | GCCAAAATAT | CAAGGATGCT | 840 |
| ATGCGTGGTT | TTCGAGAGAA | GACTAGAAAG | ATTAGAGCCA | TAAAGAATAT | TTTCAAGTGT | 900 |
| GGGTAAAACA | CGAACCCATA | TGGGTGGACG | CCAGCGTTCT | GGAATAAACC | TACAAGAGTA | 960 |
| AAATAAAATT | GCCCAGGTGA | TGATAACAAT | GGCAGGAAAA | AAAATTTGGC | GTGTTAAAGG | 1020 |
| AACGGTCAAC | GCAATGGCCA | AAAGACAGGC | AATGCCAAAT | TTCCCCCAGA | ATCCAGGAGA | 1080 |
| TTCAATGACA | ATACAAGCAA | AAATCAAATT | ACCTGCTAGA | AACACATATT | GCAAATGTGT | 1140 |

```
CCATGACCAT TTCGTATTGC GTAGCAAACG AAATGTAGGC ATAGGGTTTA AGCTTGTTTC    1200

CAACTTGTAT TGGGATGCTC GGTTACACGC AGCAAGGCGC TTTTTTAAGG TCGAAAGAGC    1260

AGACATTGCT TCAAAGAATT ATCAGAGTAA AAAAGGGAAG CGTACGAAAA AAATTTCGTA    1320

AGGAATTAAC CGGAAAACTA AGGAAAAAA AAGGAATTTT TATGAAGGAA AGAAAGTAGC    1380

TATTAAATGC AAGTGTCAAG CACTTAAAAG TAGCGATGTA AAATATTTAA AAAAAGATGG    1440

ACCGATTAAC CAATGTTCAG CTCACAGTTG CCAGCAATCA GGGCTATTTT TTTATTTTTT    1500

TTATAAAATT GCTAATTATA TATAATATAA TTAGTTTATT AACTTGCTTT TCCTCAAAAA    1560

ACCAATTCGA GAAAGGAACT TTTGCAGAGG CAAAAAAGCT T                        1601
```

(2) INFORMATION FOR SEQ ID NO:32:

(i) SEQUENCE CHARACTERISTICS:
        (A) LENGTH: 1601 bases
        (B) TYPE: nucleic acid
        (C) STRANDEDNESS: double
        (D) TOPOLOGY: linear (ii) MOLECULE TYPE: mRNA (iv) ANTI-SENSE: Yes (xi) SEQUENCE DESCRIPTION: SEQ ID NO:32:

```
AGGAAGAUGA CUUGCAUCAA AGAUGGAGGA AGUGGUACUG GCAGGACGAU CAAUCAAAUC      60

AGCAGCAGGA CUAGGUAACG GCUCAGGUGA UGAUGAACCC ACGGACCAUU CAUGAUCGGU     120

GUUAGCAAGU UCCAUAUUGU UAAGACCACU CAUGAAGGCU ACUGCAUUAG GGUUUUGAGU     180

AAAAGAAUCC CUUCCAAGUA AGUAUGGGCU GCCGGUACGA GCCAAGGAGU UGCUGGUUUU     240

UUCGGAAAGA CCAUGACCGU GGAUAACAAA CUCGUAUUCC AACGAAGGA UUUUACCAGU      300

UUGCAACUGU GGGAGGCGUA GCUUUUGAGC AAAAACGAAG CAUAUAAUAG CUAAACACAU     360

ACCGCCGACC AAAUCUACAA AGUAGUGGUG GGUAAGGUAC AUAGUACACC AGCAAAGCCA     420

UAGAACAUAU CCAUAAAAGC AGAAGCGGUA UCGAGGAAAC ACAUGCGAAA GGAAAAGUGC     480

UUCCAGCAUG GCCCAUCCAG CGUGAAGAGA UGGAAAGGCA CCAAAAACAA CCGGAGAGUU     540

AGAAAAACCA UCAGUGUAAA UGCUAGUGCC GAAGAGAGCA UCAAUACGGG CCAAUCCACC     600

AGGAGAGCCA CGUACUGCAU ACGUGGCAGG UUCUAAACCA UACAUAUUUU CAUACCAAGG     660

AGGAGAACAG GGGAAAGCCA UUUGGAUAAG AACACCAAAU AAAUUCAUAU AACCAAAAGU     720

UCGAGCCCAA ACUGGAAGAG UUCCAGGAGG UGCAAAGAUG AAAAGAAUAA AUGAAAUGAU     780

AAAAGGAGCC GAAUAAUGCA UGACUCCAUA UGGAACCCAG GCCAAAAUAU CAAGGAUGCU     840

AUGCGUGGUU UUCGAGAGAA GACUAGAAAG AUUAGAGCCA UAAAGAAUAU UUUCAAGUGU     900

GGGUAAAACA CGAACCCAUA UGGGUGGACG CCAGCGUUCU GGAAUAAACC UACAAGAGUA     960

AAAUAAAAUU GCCCAGGUGA UGAUAACAAU GGCAGGAAAA AAAAUUUGGC GUGUUAAAGG    1020

AACGGUCAAC GCAAUGGCCA AAAGACAGGC AAUGCCAAAU UCCCCCAGA UCCAGGAGA      1080

UUCAAUGACA AUACAAGCAA AAAUCAAAUU ACCUGCUAGA AACACAUAUU GCAAAUGUGU    1140

CCAUGACCAU UUCGUAUUGC GUAGCAAACG AAAUGUAGGC AUAGGGUUUA AGCUUGUUUC    1200

CAACUUGUAU UGGGAUGCUC GGUUACACGC AGCAAGGCGC UUUUUUAAGG UCGAAAGAGC    1260

AGACAUUGCU UCAAAGAAUU AUCAGAGUAA AAAAGGGAAG CGUACGAAAA AAAUUUCGUA    1320

AGGAAUUAAC CGGAAAACUA AGGAAAAAA AAGGAAUUUU UAUGAAGGAA AGAAAGUAGC    1380

UAUUAAAUGC AAGUGUCAAG CACUUAAAAG UAGCGAUGUA AAAUAUUUAA AAAAAGAUGG    1440
```

```
ACCGAUUAAC CAAUGUUCAG CUCACAGUUG CCAGCAAUCA GGGCUAUUUU UUUAUUUUUU    1500

UUAUAAAAUU GCUAAUUAUA UAUAAUAUAA UUAGUUUAUU AACUUGCUUU UCCUCAAAAA    1560

ACCAAUUCGA GAAAGGAACU UUUGCAGAGG CAAAAAAGCU U                        1601
```

(2) INFORMATION FOR SEQ ID NO:33:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Cys Phe Thr Ser Ser Tyr Phe Pro Asp Asp Arg Arg
              5                    10

(2) INFORMATION FOR SEQ ID NO:34:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Cys Tyr Thr Ser Ile Glu Lys Tyr Asp Ile Ser Lys Ser Asp Pro
              5                  10                15

Leu Ala Ala Asp (2) INFORMATION FOR SEQ ID NO:35:

(i) SEQUENCE CHARACTERISTICS:
        (A) LENGTH: 1553 bases
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:35:

```
TTTTACATAT ATTATTCACC CAATATCATA ACAAAAACAA ACTGAATGAT GGCATCTTCT     60

ATTTTGCGTT CCAAAATAAT ACAAAAACCG TACCAATTAT TCCACTACTA TTTTCTTCTG    120

GAGAAGGCTC CTGGTTCTAC AGTTAGTGAT TTGAATTTTG ATACAAACAT ACAAACGAGT    180

TTACGTAAAT TAAAGCATCA TCATTGGACG GTGGGAGAAA TATTCCATTA TGGGTTTTTG    240

GTTTCCATAC TTTTTTTCGT GTTTGTGGTT TTCCCAGCTT CATTTTTTAT AAAATTACCA    300

ATAATCTTAG CATTTGCTAC TTGTTTTTTA ATACCCTTAA CATCACAATT TTTTCTTCCT    360

GCCTTGCCCG TTTTCACTTG GTTGGCATTA TATTTTACGT GTGCTAAAAT ACCTCAAGAA    420

TGGAAACCAG CTATCACAGT TAAAGTTTTA CCAGCTATGG AAACAATTTT GTACGGCGAT    480

AATTTATCAA ATGTTTTGGC AACCATCACT ACCGGAGTGT TAGATATATT GGCATGGTTA    540

CCATATGGGA TTATTCATTT CAGTTTCCCA TTTGTACTTG CTGCTATTAT ATTTTTATTT    600

GGGCCACCGA CGGCATTAAG ATCATTTGGA TTTGCCTTTG GTTATATGAA CTTGCTTGGA    660

GTCTTGATTC AAATGGCATT CCCAGCTGCT CCTCCATGGT ACAAAAACTT GCACGGATTA    720

GAACCAGCTA ATTATTCAAT GCACGGGTCT CCTGGTGGAC TTGGAAGGAT AGATAAATTG    780
```

-continued

```
TTAGGTGTTG ATATGTATAC CACAGGGTTT TCCAATTCAT CAATCATTTT TGGGGCATTC      840

CCATCGTTAC ATTCAGGATG TTGTATCATG GAAGTGTTAT TTTTGTGTTG GTTGTTTCCA      900

CGATTCAAGT TTGTGTGGGT TACATACGCA TCTTGGCTTT GGTGGAGCAC GATGTATTTG      960

ACCCATCACT ACTTTGTCGA TTTGATTGGT GGAGCCATGC TATCTTTGAC TGTTTTTGAA     1020

TTCACCAAAT ATAAATATTT GCCAAAAAAC AAAGAAGGCC TTTTCTGTCG TTGGTCATAC     1080

ACTGAAATTG AAAAAATCGA TATCCAAGAG ATTGACCCTT TATCATACAA TTATATCCCT     1140

GTCAACAGCA ATGATAATGA AAGCAGATTG TATACGAGAG TGTACCAAGA GCCTCAGGTT     1200

AGTCCCCCAC AGAGAGCTGA ACACCTGAA GCATTTGAGA TGTCAAATTT TTCTAGGTCT      1260

AGACAAAGCT CAAAGACTCA GGTTCCATTG AGTAATCTTA CTAACAATGA TCAAGTGCCT     1320

GGAATTAACG AAGAGGATGA AGAAGAAGAA GGCGATGAAA TTTCGTCGAG TACTCCTTCG     1380

GTGTTTGAAG ACGAACCACA GGGTAGCACA TATGCTGCAT CCTCAGCTAC ATCAGTAGAT     1440

GATTTGGATT CCAAAAGAAA TTAGTAAAAC AGCAGTTTCT ATTAATTTCT TTATTTCCTC     1500

CTAATTAATG ATTTTATGTT CAATACCTAC ACTATCTGTT TTTAATTTCC TAC            1553
```

(2) INFORMATION FOR SEQ ID NO:36:

(i) SEQUENCE CHARACTERISTICS:
        (A) LENGTH: 472 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Met Met Ala Ser Ser Ile Leu Arg Ser Lys Ile Ile Gln Lys Pro
  1               5                  10                  15

Tyr Gln Leu Phe His Tyr Tyr Phe Leu Leu Glu Lys Ala Pro Gly
                 20                  25                  30

Ser Thr Val Ser Asp Leu Asn Phe Asp Thr Asn Ile Gln Thr Ser
                 35                  40                  45

Leu Arg Lys Leu Lys His His His Trp Thr Val Gly Glu Ile Phe
                 50                  55                  60

His Tyr Gly Phe Leu Val Ser Ile Leu Phe Phe Val Phe Val Val
                 65                  70                  75

Phe Pro Ala Ser Phe Phe Ile Lys Leu Pro Ile Ile Leu Ala Phe
                 80                  85                  90

Ala Thr Cys Phe Leu Ile Pro Leu Thr Ser Gln Phe Phe Leu Pro
                 95                 100                 105

Ala Leu Pro Val Phe Thr Trp Leu Ala Leu Tyr Phe Thr Cys Ala
                110                 115                 120

Lys Ile Pro Gln Glu Trp Lys Pro Ala Ile Thr Val Lys Val Leu
                125                 130                 135

Pro Ala Met Glu Thr Ile Leu Tyr Gly Asp Asn Leu Ser Asn Val
                140                 145                 150

Leu Ala Thr Ile Thr Thr Gly Val Leu Asp Ile Leu Ala Trp Leu
                155                 160                 165

Pro Tyr Gly Ile Ile His Phe Ser Phe Pro Phe Val Leu Ala Ala
                170                 175                 180

Ile Ile Phe Leu Phe Gly Pro Thr Ala Leu Arg Ser Phe Gly
                185                 190                 195
```

```
Phe Ala Phe Gly Tyr Met Asn Leu Leu Gly Val Leu Ile Gln Met
                200                 205                 210

Ala Phe Pro Ala Ala Pro Pro Trp Tyr Lys Asn Leu His Gly Leu
                215                 220                 225

Glu Pro Ala Asn Tyr Ser Met His Gly Ser Pro Gly Gly Leu Gly
                230                 235                 240

Arg Ile Asp Lys Leu Leu Gly Val Asp Met Tyr Thr Thr Gly Phe
                245                 250                 255

Ser Asn Ser Ser Ile Ile Phe Gly Ala Phe Pro Ser Leu His Ser
                260                 265                 270

Gly Cys Cys Ile Met Glu Val Leu Phe Leu Cys Trp Leu Phe Pro
                275                 280                 285

Arg Phe Lys Phe Val Trp Val Thr Tyr Ala Ser Trp Leu Trp Trp
                290                 295                 300

Ser Thr Met Tyr Leu Thr His His Tyr Phe Val Asp Leu Ile Gly
                305                 310                 315

Gly Ala Met Leu Ser Leu Thr Val Phe Glu Phe Thr Lys Tyr Lys
                320                 325                 330

Tyr Leu Pro Lys Asn Lys Glu Gly Leu Phe Cys Arg Trp Ser Tyr
                335                 340                 345

Thr Glu Ile Glu Lys Ile Asp Ile Gln Glu Ile Asp Pro Leu Ser
                350                 355                 360

Tyr Asn Tyr Ile Pro Val Asn Ser Asn Asp Asn Glu Ser Arg Leu
                365                 370                 375

Tyr Thr Arg Val Tyr Gln Glu Pro Gln Val Ser Pro Pro Gln Arg
                380                 385                 390

Ala Glu Thr Pro Glu Ala Phe Glu Met Ser Asn Phe Ser Arg Ser
                395                 400                 405

Arg Gln Ser Ser Lys Thr Gln Val Pro Leu Ser Asn Leu Thr Asn
                410                 415                 420

Asn Asp Gln Val Pro Gly Ile Asn Glu Glu Asp Glu Glu Glu Glu
                425                 430                 435

Gly Asp Glu Ile Ser Ser Ser Thr Pro Ser Val Phe Glu Asp Glu
                440                 445                 450

Pro Gln Gly Ser Thr Tyr Ala Ala Ser Ser Ala Thr Ser Val Asp
                455                 460                 465

Asp Leu Asp Ser Lys Arg Asn
                470

(2) INFORMATION FOR SEQ ID NO:37:

(i) SEQUENCE CHARACTERISTICS:
        (A) LENGTH:  22 bases
        (B) TYPE:  nucleic acid
        (C) STRANDEDNESS:  single
        (D) TOPOLOGY:  linear (ii) MOLECULE TYPE: Other nucleic acid (synthetic DNA)

(xi) SEQUENCE DESCRIPTION: SEQ ID NO:37:

GACTATTTCA TTATGGGGCC CC                                         22

(2) INFORMATION FOR SEQ ID NO:38:

(i) SEQUENCE CHARACTERISTICS:
        (A) LENGTH:  30 bases
        (B) TYPE:  nucleic acid
        (C) STRANDEDNESS:  single
```

(D) TOPOLOGY:  linear (ii) MOLECULE TYPE: Other nucleic acid (synthetic DNA)

(xi) SEQUENCE DESCRIPTION: SEQ ID NO:38:

GTTAACTCGA GAAAGTGCCC ATCAGTGTTC                                                30

(2) INFORMATION FOR SEQ ID NO:39:

(i) SEQUENCE CHARACTERISTICS:
        (A) LENGTH:  29 bases
        (B) TYPE:  nucleic acid
        (C) STRANDEDNESS:  single
        (D) TOPOLOGY:  linear (ii) MOLECULE TYPE: Other nucleic acid (synthetic DNA)

(xi) SEQUENCE DESCRIPTION: SEQ ID NO:39:

GTTAACGGTA CCTCATCGTT ACACCGTTC                                                 29

(2) INFORMATION FOR SEQ ID NO:40:

(i) SEQUENCE CHARACTERISTICS:
        (A) LENGTH:  19 bases
        (B) TYPE:  nucleic acid
        (C) STRANDEDNESS:  single
        (D) TOPOLOGY:  linear (ii) MOLECULE TYPE: Other nucleic acid (synthetic DNA)

(xi) SEQUENCE DESCRIPTION: SEQ ID NO:40:

GCTAAACGAC AATCCTGAC                                                            19

(2) INFORMATION FOR SEQ ID NO:41:

(i) SEQUENCE CHARACTERISTICS:
        (A) LENGTH:  21 bases
        (B) TYPE:  nucleic acid
        (C) STRANDEDNESS:  single
        (D) TOPOLOGY:  linear (ii) MOLECULE TYPE: Other nucleic acid (synthetic DNA)

(xi) SEQUENCE DESCRIPTION: SEQ ID NO:41:

CGTTGGCCGA TTCATTAATG C                                                         21

(2) INFORMATION FOR SEQ ID NO:42:

(i) SEQUENCE CHARACTERISTICS:
        (A) LENGTH:  401 amino acids
        (B) TYPE:  amino acid
        (C) STRANDEDNESS:  single
        (D) TOPOLOGY:  linear (ii) MOLECULE TYPE: peptide (xi) SEQUENCE DESCRIPTION: SEQ ID NO:42:

Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe

```
                    65                    70                    75
Leu Gly Thr Leu Phe Ile Ile Pro Ala Thr Ser Gln Phe Phe
                    80                    85                    90
Asn Ala Leu Pro Ile Leu Thr Trp Val Ala Leu Tyr Phe Thr Ser
                    95                   100                   105
Ser Tyr Phe Pro Asp Asp Arg Arg Pro Ile Thr Val Lys Val
                   110                   115                   120
Leu Pro Ala Val Glu Thr Ile Leu Tyr Gly Asp Asn Leu Ser Asp
                   125                   130                   135
Ile Leu Ala Thr Ser Thr Asn Ser Phe Leu Asp Ile Leu Ala Trp
                   140                   145                   150
Leu Pro Tyr Gly Leu Phe His Phe Gly Ala Pro Phe Val Val Ala
                   155                   160                   165
Ala Ile Leu Phe Val Phe Gly Pro Pro Thr Val Leu Gln Gly Tyr
                   170                   175                   180
Ala Phe Ala Phe Gly Tyr Met Asn Leu Phe Gly Val Ile Met Gln
                   185                   190                   195
Asn Val Phe Pro Ala Ala Pro Pro Trp Tyr Lys Ile Leu Tyr Gly
                   200                   205                   210
Leu Gln Ser Ala Asn Tyr Asp Met His Gly Ser Pro Gly Gly Leu
                   215                   220                   225
Ala Arg Ile Asp Lys Leu Leu Gly Ile Asn Met Tyr Thr Thr Cys
                   230                   235                   240
Phe Ser Asn Ser Ser Val Ile Phe Gly Ala Phe Pro Ser Leu His
                   245                   250                   255
Ser Gly Cys Ala Thr Met Glu Ala Leu Phe Phe Cys Tyr Cys Phe
                   260                   265                   270
Pro Lys Leu Lys Pro Leu Phe Ile Ala Tyr Val Cys Trp Leu Trp
                   275                   280                   285
Trp Ser Thr Met Tyr Leu Thr His His Tyr Phe Val Asp Leu Met
                   290                   295                   300
Ala Gly Ser Val Leu Ser Tyr Val Ile Phe Gln Tyr Thr Lys Tyr
                   305                   310                   315
Thr His Leu Pro Ile Val Asp Thr Ser Leu Phe Cys Arg Trp Ser
                   320                   325                   330
Tyr Thr Ser Ile Glu Lys Tyr Asp Ile Ser Lys Ser Asp Pro Leu
                   335                   340                   345
Ala Ala Asp Ser Asn Asp Ile Glu Ser Val Pro Leu Ser Asn Leu
                   350                   355                   360
Glu Leu Asp Phe Asp Leu Asn Met Thr Asp Glu Pro Ser Val Ser
                   365                   370                   375
Pro Ser Leu Phe Asp Gly Ser Thr Ser Val Ser Arg Ser Ser Ala
                   380                   385                   390
Thr Ser Ile Thr Ser Leu Gly Val Lys Arg Ala
                   395                   400

(2) INFORMATION FOR SEQ ID NO:43:

(i) SEQUENCE CHARACTERISTICS:
        (A) LENGTH:  401 amino acids
        (B) TYPE:  amino acid
        (C) STRANDEDNESS:  single
        (D) TOPOLOGY:  linear (ii) MOLECULE TYPE: peptide
```

(xi) SEQUENCE DESCRIPTION: SEQ ID NO:43:

```
Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                 100                 105

Ser Tyr Phe Pro Asp Asp Arg Arg Pro Pro Ile Thr Val Lys Val
               110                 115                 120

Leu Pro Ala Val Glu Thr Ile Leu Tyr Gly Asp Asn Leu Ser Asp
               125                 130                 135

Ile Leu Ala Thr Ser Thr Asn Ser Phe Leu Asp Ile Leu Ala Trp
               140                 145                 150

Leu Pro Tyr Gly Leu Phe His Tyr Gly Ala Pro Phe Val Val Ala
               155                 160                 165

Ala Ile Leu Phe Val Phe Gly Pro Pro Thr Val Leu Gln Gly Tyr
               170                 175                 180

Ala Phe Ala Phe Gly Tyr Met Asn Leu Phe Gly Val Ile Met Gln
               185                 190                 195

Asn Val Phe Pro Ala Ala Pro Pro Trp Tyr Lys Ile Leu Tyr Gly
               200                 205                 210

Leu Gln Ser Ala Asn Tyr Asp Met His Gly Ser Pro Gly Gly Leu
               215                 220                 225

Ala Arg Ile Asp Lys Leu Leu Gly Ile Asn Met Tyr Thr Thr Cys
               230                 235                 240

Phe Ser Asn Ser Ser Val Ile Phe Gly Ala Phe Pro Ser Leu His
               245                 250                 255

Ser Gly Cys Ala Thr Met Glu Ala Leu Phe Phe Cys Tyr Cys Phe
               260                 265                 270

Pro Lys Leu Lys Pro Leu Phe Ile Ala Tyr Val Cys Trp Leu Trp
               275                 280                 285

Trp Ser Thr Met Tyr Leu Thr His His Tyr Phe Val Asp Leu Met
               290                 295                 300

Ala Gly Ser Val Leu Ser Tyr Val Ile Phe Gln Tyr Thr Lys Tyr
               305                 310                 315

Thr His Leu Pro Ile Val Asp Thr Ser Leu Phe Cys Arg Trp Ser
               320                 325                 330

Tyr Thr Ser Ile Glu Lys Tyr Asp Ile Ser Lys Ser Asp Pro Leu
               335                 340                 345

Ala Ala Asp Ser Asn Asp Ile Glu Ser Val Pro Leu Ser Asn Leu
               350                 355                 360

Glu Leu Asp Phe Asp Leu Asn Met Thr Asp Glu Pro Ser Val Ser
               365                 370                 375

Pro Ser Leu Phe Asp Gly Ser Thr Ser Val Ser Arg Ser Ser Ala
               380                 385                 390
```

```
Thr Ser Ile Thr Ser Leu Gly Val Lys Arg Ala
              395                 400

(2) INFORMATION FOR SEQ ID NO:44:

(i) SEQUENCE CHARACTERISTICS:
        (A) LENGTH:  1206 base pairs
        (B) TYPE:  nucleic acid
        (C) STRANDEDNESS:  double
        (D) TOPOLOGY:  linear (ii) MOLECULE TYPE: Genomic DNA (xi) SEQUENCE DESCRIPTION: SEQ ID NO:44:

ATGGCAAACC CTTTTTCGAG ATGGTTTCTA TCAGAGAGAC CTCCAAACTG CCATGTAGCC      60

GATTTAGAAA CAAGTTTAGA TCCCCATCAA ACGTTGTTGA AGGTGCAAAA ATACAAACCC     120

GCTTTAAGCG ACTGGGTGCA TTACATCTTC TTGGGATCCA TCATGCTGTT TGTGTTCATT     180

ACTAATCCCG CACCTTGGAT CTTCAAGATC CTTTTTTATT GTTTCTTGGG CACTTTATTC     240

ATCATTCCAG CTACGTCACA GTTTTTCTTC AATGCCTTGC CCATCCTAAC ATGGGTGGCG     300

CTGTATTTCA CTTCATCGTA CTTTCCAGAT GACCGCAGGC CTCCTATTAC TGTCAAAGTG     360

TTACCAGCGG TGGAAACAAT TTTATACGGC GACAATTTAA GTGATATTCT TGCAACATCG     420

ACGAATTCCT TTTTGGACAT TTTAGCATGG TTACCGTACG GACTATTTCA TTTTGGGGCC     480

CCATTTGTCG TTGCTGCCAT CTTATTCGTA TTTGGTCCAC CAACTGTTTT GCAAGGTTAT     540

GCTTTTGCAT TTGGTTATAT GAACCTGTTT GGTGTTATCA TGCAAAATGT CTTTCCAGCC     600

GCTCCCCCAT GGTATAAAAT TCTCTATGGA TTGCAATCAG CCAACTATGA TATGCATGGC     660

TCGCCTGGTG GATTAGCTAG AATTGATAAG CTACTCGGTA TTAATATGTA TACTACATGT     720

TTTTCAAATT CCTCCGTCAT TTTCGGTGCT TTTCCTTCAC TGCATTCCGG GTGTGCTACT     780

ATGGAAGCCC TGTTTTTCTG TTATTGTTTT CCAAAATTGA AGCCCTTGTT TATTGCTTAT     840

GTTTGCTGGT TATGGTGGTC AACTATGTAT CTGACACACC ATTATTTTGT AGACCTTATG     900

GCAGGTTCTG TGCTGTCATA CGTTATTTTC CAGTACACAA AGTACACACA TTTACCAATT     960

GTAGATACAT CTCTTTTTTG CAGATGGTCA TACACTTCAA TTGAGAAATA CGATATATCA    1020

AAGAGTGATC CATTGGCTGC AGATTCAAAC GATATCGAAA GTGTCCCTTT GTCCAACTTG    1080

GAACTTGACT TTGATCTTAA TATGACTGAT GAACCCAGTG TAAGCCCTTC GTTATTTGAT    1140

GGATCTACTT CTGTTTCTCG TTCGTCCGCC ACGTCTATAA CGTCACTAGG TGTAAAGAGG    1200

GCTTAA                                                               1206

(2) INFORMATION FOR SEQ ID NO:45:

(i) SEQUENCE CHARACTERISTICS:
        (A) LENGTH:  1206 base pairs
        (B) TYPE:  nucleic acid
        (C) STRANDEDNESS:  double
        (D) TOPOLOGY:  linear (ii) MOLECULE TYPE: Genomic DNA (xi) SEQUENCE DESCRIPTION: SEQ ID NO:45:

ATGGCAAACC CTTTTTCGAG ATGGTTTCTA TCAGAGAGAC CTCCAAACTG CCATGTAGCC      60

GATTTAGAAA CAAGTTTAGA TCCCCATCAA ACGTTGTTGA AGGTGCAAAA ATACAAACCC     120

GCTTTAAGCG ACTGGGTGCA TTACATCTTC TTGGGATCCA TCATGCTGTT TGTGTTCATT     180

ACTAATCCCG CACCTTGGAT CTTCAAGATC CTTTTTTATT GTTTCTTGGG CACTTTATTC     240
```

```
ATCATTCCAG CTACGTCACA GTTTTTCTTC AATGCCTTGC CCATCCTAAC ATGGGTGGCG        300

CTGTATTTCA CTTCATCGTA CTTTCCAGAT GACCGCAGGC CTCCTATTAC TGTCAAAGTG        360

TTACCAGCGG TGGAAACAAT TTTATACGGC GACAATTTAA GTGATATTCT TGCAACATCG        420

ACGAATTCCT TTTTGGACAT TTTAGCATGG TTACCGTACG GACTATTTCA TTATGGGGCC        480

CCATTTGTCG TTGCTGCCAT CTTATTCGTA TTTGGTCCAC CAACTGTTTT GCAAGGTTAT        540

GCTTTTGCAT TTGGTTATAT GAACCTGTTT GGTGTTATCA TGCAAAATGT CTTTCCAGCC        600

GCTCCCCCAT GGTATAAAAT TCTCTATGGA TTGCAATCAG CCAACTATGA TATGCATGGC        660

TCGCCTGGTG GATTAGCTAG AATTGATAAG CTACTCGGTA TTAATATGTA TACTACATGT        720

TTTTCAAATT CCTCCGTCAT TTTCGGTGCT TTTCCTTCAC TGCATTCCGG GTGTGCTACT        780

ATGGAAGCCC TGTTTTTCTG TTATTGTTTT CCAAAATTGA AGCCCTTGTT TATTGCTTAT        840

GTTTGCTGGT TATGGTGGTC AACTATGTAT CTGACACACC ATTATTTTGT AGACCTTATG        900

GCAGGTTCTG TGCTGTCATA CGTTATTTTC CAGTACACAA AGTACACACA TTTACCAATT        960

GTAGATACAT CTCTTTTTTG CAGATGGTCA TACACTTCAA TTGAGAAATA CGATATATCA       1020

AAGAGTGATC CATTGGCTGC AGATTCAAAC GATATCGAAA GTGTCCCTTT GTCCAACTTG       1080

GAACTTGACT TTGATCTTAA TATGACTGAT GAACCCAGTG TAAGCCCTTC GTTATTTGAT       1140

GGATCTACTT CTGTTTCTCG TTCGTCCGCC ACGTCTATAA CGTCACTAGG TGTAAAGAGG       1200

GCTTAA                                                                  1206

(2) INFORMATION FOR SEQ ID NO:46:

(i) SEQUENCE CHARACTERISTICS:
        (A) LENGTH:  1206 base pairs
        (B) TYPE:  nucleic acid
        (C) STRANDEDNESS:  double
        (D) TOPOLOGY:  linear (ii) MOLECULE TYPE: Genomic DNA (xi) SEQUENCE DESCRIPTION: SEQ ID NO:46:

ATGGCAAACC CTTTTTCGAG ATGGTTTCTA TCAGAGAGAC CTCCAAACTG CCATGTAGCC         60

GATTTAGAAA CAAGTTTAGA TCCCCATCAA ACGTTGTTGA AGGTGCAAAA ATACAAACCC        120

GCTTTAAGCG ACTGGGTGCA TTACATCTTC TTGGGATCCA TCATGCTGTT TGTGTTCATT        180

ACTAATCCCG CACCTTGGAT CTTCAAGATC CTTTTTTATT GTTTCTTGGG CACTTTATTC        240

ATCATTCCAG CTACGTCACA GTTTTTCTTC AATGCCTTGC CCATCCTAAC ATGGGTGGCG        300

CTGTATTTCA CTTCATCGTA CTTTCCAGAT GACCGCAGGC CTCCTATTAC TGTCAAAGTG        360

TTACCAGCGG TGGAAACAAT TTTATACGGC GACAATTTAA GTGATATTCT TGCAACATCG        420

ACGAATTCCT TTTTGGACAT TTTAGCATGG TTACCGTACG GACTATTTCA TTATGGGGCC        480

CCATTTGTCG TTGCTGCCAT CTTATTCGTA TTTGGTCCAC CAACTGTTTT GCAAGGTTAT        540

GCTTTTGCAT TTGGTTATAT GAACCTGTTT GGTGTTATCA TGCAAAATGT CTTTCCAGCC        600

GCTCCCCCAT GGTATAAAAT TCTCTATGGA TTGCAATCAG CCAACTATGA TATGCATGGC        660

TCGCCTGGTG GATTAGCTAG AATTGATAAG CTACTCGGTA TTAATATGTA TACTACAGCT        720

TTTTCAAATT CCTCCGTCAT TTTCGGTGCT TTTCCTTCAC TGCATTCCGG GTGTGCTACT        780

ATGGAAGCCC TGTTTTTCTG TTATTGTTTT CCAAAATTGA AGCCCTTGTT TATTGCTTAT        840

GTTTGCTGGT TATGGTGGTC AACTATGTAT CTGACACACC ATTATTTTGT AGACCTTATG        900

GCAGGTTCTG TGCTGTCATA CGTTATTTTC CAGTACACAA AGTACACACA TTTACCAATT        960
```

```
GTAGATACAT CTCTTTTTTG CAGATGGTCA TACACTTCAA TTGAGAAATA CGATATATCA    1020

AAGAGTGATC CATTGGCTGC AGATTCAAAC GATATCGAAA GTGTCCCTTT GTCCAACTTG    1080

GAACTTGACT TTGATCTTAA TATGACTGAT GAACCCAGTG TAAGCCCTTC GTTATTTGAT    1140

GGATCTACTT CTGTTTCTCG TTCGTCCGCC ACGTCTATAA CGTCACTAGG TGTAAAGAGG    1200

GCTTAA                                                               1206
```

(2) INFORMATION FOR SEQ ID NO:47:

(i) SEQUENCE CHARACTERISTICS:
        (A) LENGTH: 1206 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:47:

```
ATGGCAAACC CTTTTTCGAG ATGGTTTCTA TCAGAGAGAC CTCCAAACTG CCATGTAGCC      60

GATTTAGAAA CAAGTTTAGA TCCCCATCAA ACGTTGTTGA AGGTGCAAAA ATACAAACCC     120

GCTTTAAGCG ACTGGGTGCA TTACATCTTC TTGGGATCCA TCATGCTGTT TGTGTTCATT     180

ACTAATCCCG CACCTTGGAT CTTCAAGATC CTTTTTTATT GTTTCTTGGG CACTTTATTC     240

ATCATTCCAG CTACGTCACA GTTTTTCTTC AATGCCTTGC CCATCCTAAC ATGGGTGGCG     300

CTGTATTTCA CTTCATCGTA CTTTCCAGAT GACCGCAGGC CTCCTATTAC TGTCAAAGTG     360

TTACCAGCGG TGGAAACAAT TTTATACGGC GACAATTTAA GTGATATTCT TGCAACATCG     420

ACGAATTCCT TTTTGGACAT TTTAGCATGG TTACCGTACG GACTATTTCA TTTTGGGGCC     480

CCATTTGTCG TTGCTGCCAT CTTATTCGTA TTTGGTCCAC CAACTGTTTT GCAAGGTTAT     540

GCTTTTGCAT TTGGTTATAT GAACCTGTTT GGTGTTATCA TGCAAAATGT CTTTCCAGCC     600

GCTCCCCCAT GGTATAAAAT TCTCTATGGA TTGCAATCAG CCAACTATGA TATGCATGGC     660

TCGCCTGGTG GATTAGCTAG AATTGATAAG CTACTCGGTA TTAATATGTA TACTACAGCT     720

TTTTCAAATT CCTCCGTCAT TTTCGGTGCT TTTCCTTCAC TGCATTCCGG GTGTGCTACT     780

ATGGAAGCCC TGTTTTTCTG TTATTGTTTT CCAAAATTGA AGCCCTTGTT TATTGCTTAT     840

GTTTGCTGGT TATGGTGGTC AACTATGTAT CTGACACACC ATTATTTTGT AGACCTTATG     900

GCAGGTTCTG TGCTGTCATA CGTTATTTTC CAGTACACAA AGTACACACA TTTACCAATT     960

GTAGATACAT CTCTTTTTTG CAGATGGTCA TACACTTCAA TTGAGAAATA CGATATATCA    1020

AAGAGTGATC CATTGGCTGC AGATTCAAAC GATATCGAAA GTGTCCCTTT GTCCAACTTG    1080

GAACTTGACT TTGATCTTAA TATGACTGAT GAACCCAGTG TAAGCCCTTC GTTATTTGAT    1140

GGATCTACTT CTGTTTCTCG TTCGTCCGCC ACGTCTATAA CGTCACTAGG TGTAAAGAGG    1200

GCTTAA                                                               1206
```

(2) INFORMATION FOR SEQ ID NO:48:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:48:

-continued

```
AATATGTATA CTACATGTTT TTCAAATTCC                                         30

(2) INFORMATION FOR SEQ ID NO:49:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:49:

GTTAACTCGA GAAAGTGCCC ATCAGTGTTC                                         30

(2) INFORMATION FOR SEQ ID NO:50:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:50:

GTTAACGGTA CCAGAGGAAA GAATAACGC                                          29
```